United States Patent
Carson et al.

(10) Patent No.: US 8,414,748 B2
(45) Date of Patent: *Apr. 9, 2013

(54) APPARATUS AND PROCESS FOR MEDIATED ELECTROCHEMICAL OXIDATION OF MATERIALS

(75) Inventors: Roger W. Carson, Vienna, VA (US); Bruce W. Bremer, Franklin, MA (US); Michael L. Mastracci, Rockville, MD (US); Kent E. Maggard, Springfield, VA (US)

(73) Assignee: Scimist, Inc., Vienna, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/560,576

(22) PCT Filed: Jun. 10, 2004

(86) PCT No.: PCT/US2004/018447

§ 371 (c)(1), (2), (4) Date: Dec. 30, 2005

(87) PCT Pub. No.: WO2005/028372

PCT Pub. Date: Mar. 31, 2005

(65) Prior Publication Data

US 2006/0144700 A1      Jul. 6, 2006

Related U.S. Application Data

(60) Provisional application No. 60/477,162, filed on Jun. 10, 2003.

(51) Int. Cl.
*C02F 1/461* (2006.01)
*C25B 9/00* (2006.01)
*C25B 9/08* (2006.01)

(52) U.S. Cl. ......... 204/252; 204/253; 204/257; 205/746

(58) Field of Classification Search ............ 204/263; 205/746

See application file for complete search history.

(56) References Cited

U.S. PATENT DOCUMENTS

| | | | |
|---|---|---|---|
| 4,013,552 | A | 3/1977 | Kreuter |
| 4,069,371 | A | 1/1978 | Zito |
| 4,749,519 | A | 6/1988 | Koehly et al. |
| 4,752,364 | A | 6/1988 | Dhooge |

(Continued)

FOREIGN PATENT DOCUMENTS

| | | |
|---|---|---|
| DE | 4113817 | 11/1991 |
| DE | 4205739 | 8/1993 |
| WO | WO97/15354 | 5/1997 |
| WO | WO 03/031343 A1 * | 4/2003 |

OTHER PUBLICATIONS

Chiba et al.; *Mediated Electrochemical Oxidation as an Alternative to Incineration for Mixed Wastes*; Lawrence Livermore National Laboratory Paper (UCRL-JC-119133) prepared for WM95 Synposia, Tucson, AZ, Mar. 1, 1995 (dated Feb. 1995) (12 pages).

(Continued)

*Primary Examiner* — Harry D Wilkins, III
(74) *Attorney, Agent, or Firm* — James Creighton Wray

(57) ABSTRACT

A cell design for systems of mediated electrochemical oxidation (MEO) of materials includes inactive surface coatings, such as polyvinylidene fluoride, polypropylene, ethylene-chlorotrifluoroethylene and polytetrafluoroethylene polymers or a glass glaze or metallic oxide, on all interior surfaces of the electrochemical cell to prevent . A further cell design for systems of mediated electrochemical oxidation (MEO) included conduits for connecting plural catholyte chambers or for connecting plural anolyte chambers which are embedded within walls of a molded unibody constructed box and slots for parallel arrangement of membranes and porous electrodes.

36 Claims, 23 Drawing Sheets

U.S. PATENT DOCUMENTS

| | | | |
|---|---|---|---|
| 4,874,485 | A | 10/1989 | Steele |
| 4,925,643 | A | 5/1990 | Steele |
| 4,967,673 | A | 11/1990 | Gunn |
| 5,047,224 | A | 9/1991 | Dhooge |
| 5,261,336 | A | 11/1993 | Williams |
| 5,380,445 | A | 1/1995 | Rivard et al. |
| 5,516,972 | A | 5/1996 | Farmer |
| 5,707,508 | A | 1/1998 | Surma et al. |
| 5,756,874 | A | 5/1998 | Steward |
| 5,810,995 | A | 9/1998 | Soilleux et al. |
| 5,855,763 | A | 1/1999 | Conlin et al. |
| 5,911,868 | A | 6/1999 | Balazs et al. |
| 5,919,350 | A | 7/1999 | Balazs et al. |
| 5,952,542 | A | 9/1999 | Steele |
| 5,968,337 | A | 10/1999 | Surma |
| 6,402,932 | B1 | 6/2002 | Bremer et al. |

OTHER PUBLICATIONS

Davidson, L. et al.; *Ruthenium-Mediated Electrochemical Destruction of Organic Wastes*; Platinum Metal Reviews; 1998; vol. 42, No. 3; pp. 90-98 (Ruthenium).

Morrison, R. & Boyd, R. (Editors); *Organic Chemistry*; New York University; Allen & Bacon, Inc.; 1973; (Third Edition); Chapter 1—Structure & Properties; pp. 1-2 (Organic).

Pletcher, D. & Walsh, F.; *Industrial Electrochemistry*; 1990; Chapman & Hall; Chapters 1 & 2; pp. 1-172.

Surma et al.; *Catalyzed Electrochemical Oxidation (CEO) of Rocky Flats Contaminated Combustible Materials*; Mar. 1996; Report prepared for U.S. Department of Energy, Pacific Northwest National Laboratory, Richland, WA; 25 pages.

Steward Tony; *Electrochemical Oxidation of Hazardous Organics*; Sep. 20, 1996; EO Systems, Inc.; 2 pages.

Whaley, S.; *UNR Attacks Hazardous Waste Riddle*; Las Vegas Review-Journal Oct. 21, 1997; 3 pages.

Lewis, R.; *Hawley's Condensed Chemical Dictionary*; Twelfth Edition; 1993; Van Nostrand—Reinhold; 4 pages.

Anonymous; *Chemical Storage Tank Systems—Good Practice Guide (Summary Guidance Document)*; CIRIA Publication W002; Classic House, 174-180 Old Street, London, EC1V-9BP, England. 43 pages.

* cited by examiner

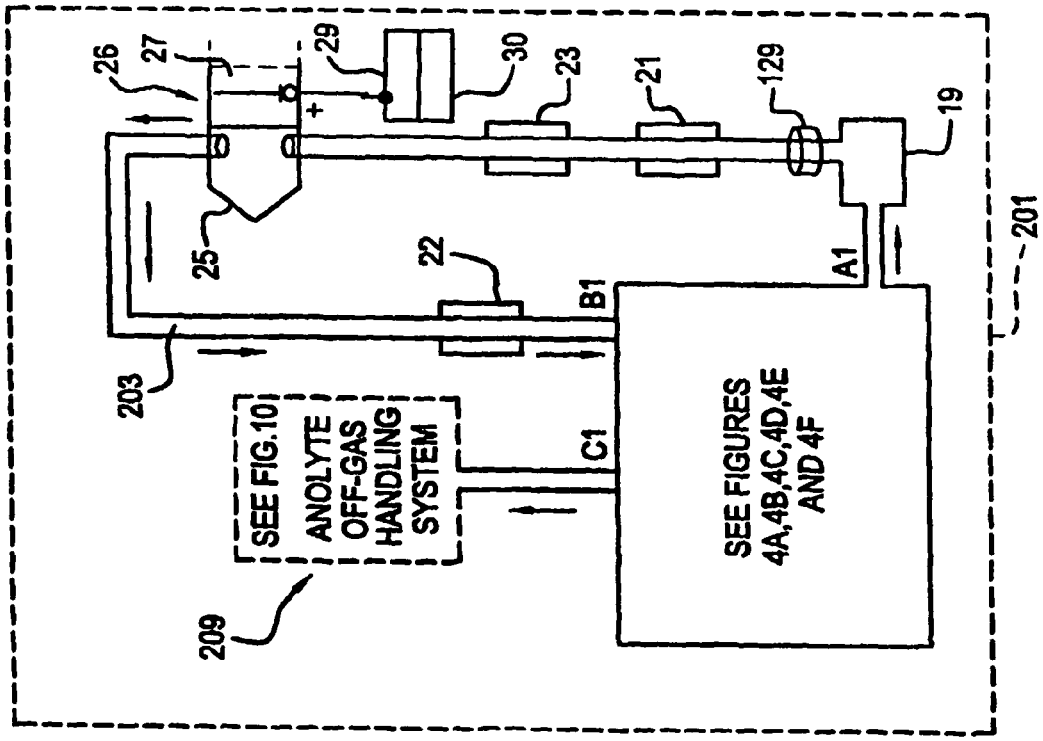

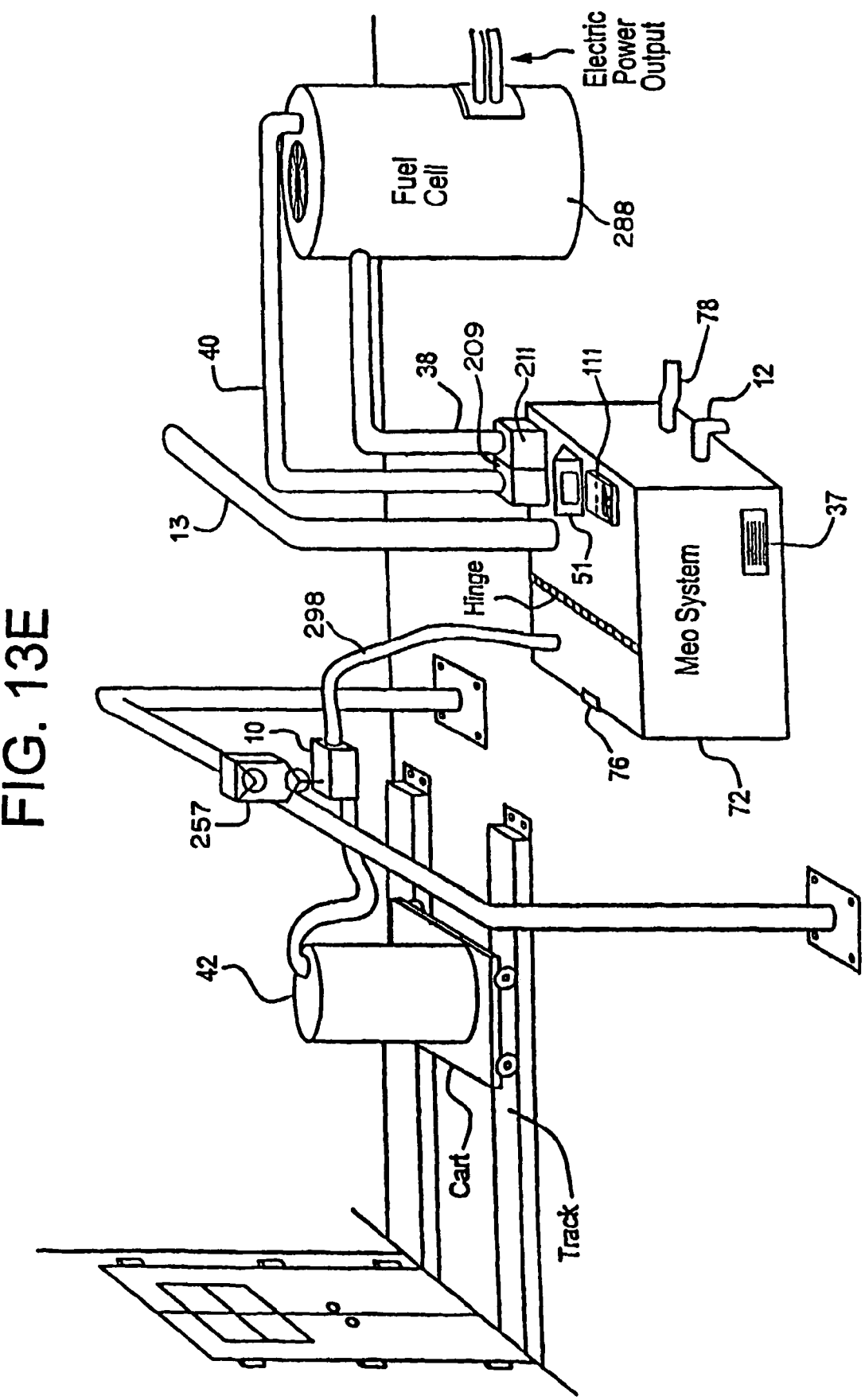

APPARATUS AND PROCESS FOR MEDIATED
ELECTROCHEMICAL OXIDATION OF
MATERIALS

This application claims the benefit of U.S. Provisional Application No. 60/477,162 filed Jun. 10, 2003 and PCT/US2004/018447 filed Jun. 10, 2004, which are hereby incorporated by reference in their entirety.

FIELD OF THE INVENTION

This invention relates generally to a unique apparatus and process that uses mediated electrochemical oxidation (MEO) for:

(1) Destruction of: a) nearly all organic solid, liquid, and gases materials, except fluorinated hydrocarbons; b) all biological solid, liquid, and gases materials; c) and/or dissolution and decontamination (such as cleaning equipment and containers, etc.) of nearly all inorganic solid, liquid, or gas where higher oxidation states exist which includes, but is not limited to, halogenated inorganic compounds (except fluorinated), inorganic pesticides and herbicides, inorganic fertilizers, carbon residues, inorganic carbon compounds, mineral formations, mining tailings, inorganic salts, metals and metal compounds, etc.); and d) combined materials (e.g. a mixture of any of the foregoing with each other); henceforth collectively referred to as materials.
(2) Sterilization/disinfection of equipment, glassware, etc., by destroying all existing infectious materials.
(3) Dissolution of transuranic/actinide materials and/or destruction of the oxidizable components in the hazardous waste portion of mixed waste.
(4) Generation of hydrogen from the cathodic reduction of hydrogen and/or hydronium ions.
(5) Alteration of organic, biological, and inorganic materials by MEO to produce other compounds from these materials.

BACKGROUND OF THE INVENTION

The varieties of materials being used in society are creating a growing problem for today's technological world. The problem is the disposal of those materials that are no longer needed or wanted (hereinafter referred to as materials). These materials are generated by a large segment of our public, private, and industrial sectors, and are an increasing burden on these sectors as well as the whole country in general. Considerable researches in the fields of public health safety and environmental protection have raised the level of concern relative to the impact of these materials on our society. This has lead to an expanded definition of those materials that must be handled in a controlled manner.

The cost of disposing of materials in the U.S. is a multibillion dollar per year industry. The capital cost of the equipment required to dispose of these materials is in the hundreds of millions of dollars. Furthermore, the handling, transporting, and management of the disposal process have continued to increase in cost.

In recent years there has been increasing concern over the disposal of materials. All businesses, industrial companies, and institutions that generate and handle these categories of materials must provide safe effective and inexpensive disposal of the materials. Also the number of materials that need to be controlled has continued to increase.

The liability for the disposal of these materials is a major concern. The liability of the users does not end with the transfer of control of these materials to disposal companies; the user is still liable after transfer of control for all future problems that may be caused by the materials. The concern over the control and safety standards for the handling of materials has lead to a whole family of regulatory Federal Acts and State regulations.

The dominant methodologies used today generally can be categorized as thermal decomposition, long-term storage, or landfills methods. The most frequently used thermal destruction techniques are various forms of incineration. All of these thermal techniques have the potential to produce volatile organics that have serious health and environmental consequences. The thermal process converts solids and liquids to gas products at some point in their destruction of the materials. Gases are much harder to control and contain which makes this process undesirable and a potential threat to society and the environment. Typical of these toxic substances are dioxins and furans which are controlled materials. Dioxins and furans are formed in off gas streams that are cooled through the temperature range from 350° C. to approximately 250° C. The use of long-term storage and landfills just delay the potential problem the materials poses for society to a later time. In the case of long-term storage, this method is viewed as delaying the solving of the problem and in fact actually increases the degree of the problem in the future.

SUMMARY OF THE INVENTION

The inventors of this patent have developed an MEO apparatus and process(s) that offer an alternative technology that does not create these conditions. The current position argued by EPA is to move in the direction of avoiding the use of the materials by using alternatives solutions in lieu of containment. The dumping in landfills has considerable risk for the users of these materials. Therefore, the user community has an immediate need to develop and incorporate improved methods for the handling of all types and form of materials.

The MEO apparatus and processes developed by the inventors in this patent provides for the immediate destruction of materials which eliminates materials handling and storage problems. The MEO destruction technology developed by the inventors in this patent converts the materials into benign natural components. Using this methodology, nearly all organic solid, liquid or gaseous materials are decomposed into carbon dioxide, water, and trace amounts of inorganic salts.

The apparatus covered under this patent represent numerous unique design configurations throughout the apparatus and unique choices of materials for their construction. The apparatus in this patent cover the full range of designs for liquids, solids, gases, and combinations of all three states.

The invention in this patent relates to apparatus for the use of a mediated electrochemical oxidation (MEO) processes for: (1) destruction of: a) nearly all organic solid, liquid, and gaseous materials, except fluorinated hydrocarbons; b) all biological solid, liquid, and gaseous materials; c) and/or dissolution of inorganic solid, liquid, and gaseous materials, where higher oxidation states exist for at least one element in those compounds; and d) combined materials (e.g. a mixture of any of the foregoing with each other); henceforth collectively referred to as materials; (2) sterilization/disinfection: a) by destroying all infectious materials; b) by sterilizing of equipment, glassware, etc of infectious materials; (3) dissolution of transuranic/actinide material and/or destruction of the oxidizable components in the hazardous waste portion of mixed waste; (4) generation of hydrogen from the cathodic reduction of hydrogen and/or hydronium ions; and (5) alteration of organic, biological, and inorganic materials by MEO to produce other compounds. The apparatus and the methodology used in this patent have the flexibility to deal with all of the forms of the materials as identified. In the following sections, the MEO process will be summarized first, followed by an explanation of the unique apparatus.

MEO Process

The mediated electrochemical oxidation (MEO) process involves an electrolyte containing one or more redox couples, wherein the oxidized form of at least one redox couple is produced by anodic oxidation at the anode of an electrochemical cell. The oxidized forms of any other redox couples present are produced either by similar anodic oxidation or reaction with the oxidized form of other redox couples that are present and capable of affecting the required redox reaction. The anodic oxidation in the electrochemical cell is driven by an externally induced electrical potential induced between the anode(s) and cathode(s) of the cell. The oxidized species of the redox couples oxidize the molecules of the materials and are themselves converted to their reduced form, whereupon they are reoxidized by either of the aforementioned mechanisms. The redox cycle continues until all oxidizable material species, including intermediate reaction products, have undergone the desired degree of oxidation. The redox species ions are thus seen to "mediate" the transfer of electrons from the materials molecules to the anode, (i.e., oxidation of the materials).

A membrane in the electrochemical cell separates the anolyte and catholyte, thereby preventing parasitic reduction of the oxidizing species at the cathode. The membrane is ion-selective or semi-permeable (i.e., micro porous plastic, ceramic, sintered glass frit, etc.). The preferred MEO process uses the mediator species described in Table I (simple anions redox couple mediators); the Type I isopolyanions (IPA) formed by Mo, W, V, Nb, and Ta, and mixtures thereof; the Type I heteropolyanions (HPA) formed by incorporation into the aforementioned isopolyanions of any of the elements listed in Table II (heteroatoms) either singly or in combinations thereof; any type heteropolyanion containing at least one heteropolyatom (i.e. element) contained in both Table I and Table II; or combinations of mediator species from any or all of these generic groups.

Some redox couples may have short life times (i.e., seconds to minutes) while other redox couples may remain in the electrolyte for hours and days. A unique electrochemical discharger has been invented and disclosed in this patent. The purpose of the discharger is to electrochemically reduce the oxidized form of the redox couple to the reduced form. This electrochemical reduction process is used to suppress the population of the strong oxidizers in the MEO apparatus when they are no longer needed or desired. The discharger is composed of a box with at least two electrodes without a membrane separator. A direct current and/or alternating electric potential, usually less then the potential in the electrochemical cell used to generate the oxidizers, is applied between adjacent two electrodes. The anolyte is pumped through the discharger whereby the oxidizers contact the cathode(s) and gains electrons. This reduction of the oxidizer species converts it back to its initial state in the anolyte. During the discharge process the MEO electrochemical cell is turned off.

Simple Anion Redox Couple Mediators

Table I show the simple anion redox couple mediators used in the preferred MEO process wherein, "species" defines the specific ions for each chemical element that have applicability to the MEO process as either the reduced (e.g., $Fe^{+3}$) or oxidizer (e.g., $FeO_4^{-2}$) form of the mediator characteristic element (e.g., Fe); and, the "specific redox couple" defines the specific associations of the reduced and oxidized forms of these species (e.g., $Fe^{+3}/FeO_4^{-2}$) that are described for the MEO process. Species soluble in the anolyte are shown in Table I in normal print while those that are insoluble are shown in bold underlined print. Some characteristics of the MEO processes described in this patent are specified in the following paragraphs.

The anolyte contains one or more redox couples which in their oxidized form consist of either single multivalent element anions (e.g., $Ag^{+2}$, $Ce^{+4}$, $Co^{+3}$, $Pb^{+4}$, etc.); insoluble oxides of multivalent elements (e.g., $PbO_2$, $CeO_2$, $PrO_2$, etc.); or simple oxoanions (also called oxyanions) of multivalent elements (e.g., $FeO_4^{-2}$, $NiO_4^{-2}$, $BiO_3^-$, etc.). The redox couples in their oxidized form are called the mediator species. The nonoxygen multivalent element component of the mediator is called the characteristic element of the mediator species. We have chosen to group the simple oxoanions with the simple anion redox couple mediators rather than with the complex (i.e., polyoxometallate (POM)) anion redox couple mediators discussed in the next section, and refer to them collectively as simple anion redox couple mediators.

In one embodiment of this process both the oxidized and reduced forms of the redox couple are soluble in the anolyte. The reduced form of the couple is anodically oxidized to the oxidized form at the cell anode(s) whereupon it oxidizes the molecules of the materials either dissolved in or located on materials particle surfaces wetted by the anolyte. After the concomitant reduction of the oxidizing agent to its reduced form, the MEO process begins again with the reoxidation of this species at the cell anode(s). If other less powerful redox couples of this type (i.e., reduced and oxidized forms soluble in anolyte) are present, they too may undergo direct anodic oxidation or the anodically oxidized more powerful oxidizing agent may oxidize them rather than a materials molecule. The weaker redox couples are selected such that their oxidation potential is sufficient to affect the desired reaction with the materials molecules. The oxidized species of all the redox couples oxidize the materials molecules and are themselves converted to their reduced form, whereupon they are reoxidized by either of the aforementioned mechanisms and the redox cycle continues until all oxidizable materials species, including intermediate reaction products, have undergone the desired degree of oxidation.

The preferred mode for the MEO process as described in the preceding section is for the redox couple species to be soluble in the anolyte in both the oxidized and reduced form; however this is not the only mode of operation claimed herein. If the reduced form of the redox couple is soluble in the anolyte (e.g., $Pb^{+2}$) but the oxidized form is not (e.g., $PbO_2$), the following process are operative. The insoluble oxidizing agent is produced either as a surface layer on the anode by anodic oxidation, or throughout the bulk of the anolyte by reacting with the oxidized form of other redox couples present capable of affecting the required redox reaction, at least one of which is formed by anodic oxidation. The oxidizable materials are either soluble in the anolyte or dispersed therein at a fine particle size, (e.g., emulsion, colloid, etc.) thereby affecting intimate contact with the surface of the insoluble oxidizing agent (e.g., $PbO_2$) particles. Upon reaction of the materials with the oxidizing agent particles, the materials are oxidized, and the insoluble oxidizing agent molecules on the anolyte wetted surfaces of the oxidizing agent particles reacting with the materials are reduced to their soluble form and are returned to the bulk anolyte, available for continuing the MEO process by being reoxidized.

In another variant of the MEO process, if the reduced form of the redox couple is insoluble in the anolyte (e.g., $TiO_2$) but the oxidized form is soluble (e.g., $TiO_2^{+2}$), the following process are operative. The soluble (i.e., oxidized) form of the redox couple is produced by the reaction of the insoluble (i.e., reduced form) redox couple molecules on the anolyte wetted surfaces of the oxidizing agent particles with the soluble oxidized form of other redox couples present capable of affecting the required redox reaction, at least one of which is formed by anodic oxidation and soluble in the anolyte in both the reduced and oxidized forms. The soluble oxidized species so formed are released into the anolyte, whereupon they oxidize materials molecules in the manner previously described and are themselves converted to the insoluble form of the redox couple, thereupon returning to the starting point of the redox MEO cycle.

In this invention, when an alkaline anolyte is used, the $CO_2$ resulting from oxidation of the materials reacts with the anolyte to form alkali metal bicarbonates/carbonates. The bicarbonate/carbonate ions circulate within the anolyte where they are reversibly oxidized to percarbonate ions either by anodic oxidation within the electrochemical cell or alternately by reacting with the oxidized form of a more powerful redox couple mediator, when present in the anolyte. The carbonate thus functions exactly as a simple anion redox couple mediator, thereby producing an oxidizing species from the materials oxidation products that is capable of destroying additional materials.

The electrolytes used in this patent are from a family of acids, alkali, and neutral salt aqueous solutions (e.g. sulfuric acid, potassium hydroxide, sodium sulfate aqueous solutions, etc.).

A given redox couple or mixture of redox couples (i.e. mediator species) are to be used with different electrolytes.

The electrolyte composition is selected based on demonstrated adequate solubility of the compound containing at least one of the mediator species present in the reduced form (e.g., sulfuric acid may be used with ferric sulfate, etc.). The concentration of the mediator species containing compounds in the anolyte may range from 0.0005 molar (M) up to the saturation point.

The concentration of electrolyte in the anolyte is governed by its effect upon the solubility of the mediator species containing compounds and by the conductivity of the anolyte solution desired in the electrochemical cell for the given mediator species being used to allow the desired cell current at the desired cell voltage.

The temperature over which the MEO process may be operated ranges from approximately 0° C. too slightly below the boiling point of the electrolytic solution.

The operational temperature of the most frequently used thermal techniques, such as incineration, exceed this temperature range and thus, unlike the MEO process, have the potential to produce volatile organics that have serious health and environmental consequences. Typically, these volatile organic substances are dioxins and furans, which are controlled materials. The MEO process is operated at atmospheric pressure.

The mediator species are differentiated on the basis of whether they are capable of reacting with the electrolyte to produce free radicals (e.g., $.O_2H$ (perhydroxyl), $.OH$ (hydroxyl), $.SO_4$ (sulfate), $.NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the electrodes in the electrochemical cell is based upon the oxidation potential of the most reactive redox couple presents in the anolyte that is serving as a mediator species and the ohmic losses within the cell. Within the current density range of interest the electrical potential may be approximately 2.5 to 3.5 volts.

In the case of certain electrolyte compositions, a low level AC voltage is impressed across the electrodes in the electrochemical cell. The AC voltage is used to retard the formation of surface films on the electrodes that would have a performance limiting effect within the current density range of interest, the electrical potential may be approximately 2.5 to 3.5 volts.

Complex Anion Redox Couple Mediators

The preferred characteristic of the oxidizing species in the MEO process is that it be soluble in the aqueous anolyte in both the oxidized and reduced states. The majorities of metal oxides and oxoanion (oxyanion) salts are insoluble, or have poorly defined or limited solution chemistry. The early transition elements, however, are capable of spontaneously forming a class of discrete polymeric structures called polyoxometallates (POMs) which are highly soluble in aqueous solutions over a wide pH range. The polymerization of simple tetrahedral oxoanions of interest herein involves an expansion of the metal, M, coordination number to 6, and the edge and corner linkage of $MO_6$ octahedra. Chromium is limited to a coordination number of 4, restricting the POMs based on $CrO_4$ tetrahedra to the dichromate ion $[Cr_2O_7]^{-2}$ which is included in Table I. Based upon their chemical composition POMs are divided into the two subclasses isopolyanions (IPAs) and heteropolyanions (IPAs), as shown by the following general formulas:

Isopolyanions (IPAS)–$[M_mO_y]^{p-}$ and,

Heteropolyanions (HPAs)–$[X_xM_mO_y]^{q-}$ (m>x)

where the addenda atom, M, is usually Molybdenum (Mo) or Tungsten (W), and less frequently Vanadium (V), Niobium (Nb), or Tantalum (Ta), or mixtures of these elements in their highest ($d^0$) oxidation state. The elements that can function as addenda atoms in IPAs and HPAs appear to be limited to those with both a favorable combination of ionic radius and charge, and the ability to form $d\pi$-$p\pi$ M-O bonds. However, the heteroatoms, X, have no such limitations and can be any of the elements listed in Table II.

There is a vast chemistry of POMs that involves the oxidation/reduction of the addenda atoms and those heteroatoms listed in Table II, which exhibit multiple oxidation states. The partial reduction of the addenda, M, atoms in some POMs strictures (i.e., both IPAs and HPAs) produces intensely colored species, generically referred to as "heteropoly blues". Based on structural differences, POMs can be divided into two groups, Type I and Type II. Type I POMs consist of $MO_6$ octahedra each having one terminal oxo oxygen atom while Type II has 2 terminal oxo oxygen atoms. Type II POMs can only accommodate addenda atoms with $d^0$ electronic configurations, whereas Type I; e.g., Keggin ($XM_{12}O_{40}$), Dawson ($X_2M_{18}O_{62}$), hexametalate ($M_6O_{19}$), decatungstate ($W_{10}O_{32}$), etc., can accommodate addenda atoms with $d^0$, $d^1$, and $d^2$ electronic configurations. Therefore, while Type I structures can easily undergo reversible redox reactions, structural limitations preclude this ability in Type II structures. Oxidizing species applicable for the MEO process are therefore Type I POMs (i.e., IPAs and HPAs) where the addenda, M, atoms are W, Mo, V, Nb, Ta, or combinations thereof.

The high negative charges of polyanions often stabilize heteroatoms in unusually high oxidation states, thereby creating a second category of MEO oxidizers in addition to the aforementioned Type I POMs. Any Type I or Type II HPA containing any of the heteroatom elements, X, listed in Table II, that also are listed in Table I as simple anion redox couple mediators, can also function as an oxidizing species in the MEO process.

The anolyte contains one or more complex anion redox couples, each consisting of either the afore mentioned Type I POMs containing W, Mo, V, Nb, Ta or combinations thereof as the addenda atoms, or HPAs having as heteroatoms (X) any elements contained in both Tables I and II, and which are soluble in the electrolyte (e.g. sulfuric acid, etc.).

The electrolytes used in the apparatus are from a family of acids, alkali, and neutral salt aqueous solutions (e.g. sulfuric acid, potassium hydroxide, sodium sulfate aqueous solutions, etc.).

A given POM redox couple or mixture of POM redox couples (i.e., mediator species) may be used with different electrolytes.

The electrolyte composition is selected based on demonstrating adequate solubility of at least one of the compounds containing the POM mediator species in the reduced form and being part of a redox couple of sufficient oxidation potential to affect oxidation of the other mediator species present.

The concentration of the POM mediator species containing compounds in the anolyte may range from 0.0005M (molar) up to the saturation point.

The concentration of electrolyte in the anolyte may be governed by its effect upon the solubility of the POM mediator species containing compounds and by the conductivity of the anolyte solution desired in the electrochemical cell for the given POM mediator species being used to allow the desired cell current at the desired cell voltage.

The temperature over which the electrochemical cell may be operated ranges from approximately 0° C. to slightly below the boiling point of the electrolytic solution. The operational temperatures of the most frequently used thermal techniques, such as incineration, exceed this temperature range and thus, unlike the MEO process. All of those thermal techniques have the potential to produce volatile organics that have serious health and environmental consequences. Typical of those volatile organic substances are dioxins and furans, which are, controlled materials.

The MEO process is operated at atmospheric pressure.

The POM mediator species are differentiated on the basis of whether they are capable of reacting with the electrolyte to produce free radicals (e.g., $.O_2H$ (perhydroxyl), $.OH$ (hydroxyl), $.SO_4$ (sulfate), $.NO_3$ (nitrate), etc.). Such mediator species are classified herein as "super oxidizers" (SO) and typically exhibit oxidation potentials at least equal to that of the $Ce^{+3}/Ce^{+4}$ redox couple (i.e., 1.7 volts at 1 molar, 25° C. and pH 1).

The electrical potential between the anode(s) and cathode(s) in the electrochemical cell is based on the oxidation potential of the most reactive POM redox couples present in the anolyte and serving as a mediator species, and the ohmic losses within the cell.

In the case of certain electrolyte compositions, an AC voltage is impressed upon the DC voltage across the electrodes in the electrochemical cell, or the AC voltage may be applied between the electrodes without the presence of a DC voltage. The AC voltage is used to retard or prevent the formation of surface films on the electrodes that would have a performance limiting effect within the voltage range of interest (i.e., approximately 2.5 to 3.5 volts).

Mixed Simple and Complex Anion Redox Couple Mediators

The preferred MEO process for a combination of simple anion redox couple mediators (A) and complex anion redox couple mediators (B) may be mixed together to form the system anolyte. The characteristics of the resulting MEO process are similar to the previous discussions.

The use of multiple oxidizer species in the MEO process has the following potential advantages:

1) If a second mediator "B" is added to the anolyte containing mediator "A", there is a potential for increasing the destruction through a three step reaction process. The overall materials destruction rate is increased if the three step reaction kinetics (i.e., first, mediator "A" is anodically oxidized; second, mediator "B" is oxidized by mediator "A"; and third, mediator "B" oxidizes the materials), are sufficiently rapid such that the combined speed of the three step reaction train is faster than a two step reaction train. The two step reaction train is composed of; first, either mediator "A" or "B" is anodically oxidized; and second, either oxidized mediators "A" or "B" oxidizes the materials directly.

2) If the cost of mediator "B" is sufficiently less than that of mediator "A", the use of the above three step reaction train results in lowering the cost of materials destruction due to the reduced cost associated with the smaller required inventory and process losses of the more expensive mediator "A".

3) An example of this is the use of the silver (II)-peroxysulfate mediator system. The cost associated with the silver (I/II) only MEO process, coupled with the slow anodic oxidation kinetics of a sulfate/peroxysulfate only, are overcome in the combined MEO process.

The MEO process is "desensitized" to changes in the types of molecular bonds present in the materials as the use of multiple mediators, each selectively attacking different type of chemical bonds, results in a highly "nonselective" oxidizing system.

Additional MEO Electrolyte Features

In one preferred embodiment of this invention, the catholyte and anolyte are discrete entities separated by a membrane, thus they are not constrained to share any common properties such as electrolyte concentration, composition, or pH (i.e., acid, alkali, or neutral). The process operates over the temperature range from approximately 0° C. to slightly below the boiling point of the electrolyte used during the destruction of the materials. However, it is not necessary to operate the electrochemical cell and anolyte reaction chamber at the same temperature within this range as the optimum temperatures for oxidizer formation and material oxidation may be different.

Each of the following patent(s)/co-pending applications are incorporated herein by reference in their entireties:
U.S. Pat. No. 6,402,932 issued Jun. 11, 2002.
U.S. application Ser. No. 10/263,810 filed Oct. 4, 2002.
U.S. application Ser. No. 10/127,604 filed Apr. 23, 2002.
U.S. Provisional Application Ser. No. 60/409,202 filed Sep. 10, 2002.
U.S. Provisional Application Ser. No. 60/398,808 filed Jul. 29, 2002.

PCT/US02/03249 filed Feb. 6, 2002.
PCT/US03/02151 based on U.S. Provisional Application Ser. No. 60/350,352 filed Jan. 24, 2002.
PCT/US03/02152 based on U.S. Provisional Application Ser. No. 60/350,377 filed Jan. 24, 2002.
PCT/US03/02153 based on U.S. Provisional Application Ser. No. 60/350,378 filed Jan. 24, 2002.
PCT/US03/13051 based on U.S. Provisional Application Ser. No. 60/375,430 filed Apr. 26, 2002.
PCT/US03/04065 filed Feb. 12, 2003.
PCT/US02/33732 based on U.S. Provisional Application Ser. No. 60/330,436 filed Oct. 22, 2001.
PCT/US02/32040 based on U.S. Provisional Application Ser. No. 60/327,306 filed Oct. 9, 2001.

These and further and other objects and features of the invention are apparent in the disclosure, which includes the above and ongoing written specification, with the drawings and the claims.

MEO Apparatus

BRIEF DESCRIPTION OF THE DRAWINGS

FIG. 1 is a representation of a general embodiment of the present invention with the understanding that not all of the components shown therein must necessarily be employed in all situations and others may be added as needed for a particular application.

FIG. 2 Anolyte System is a representation of an anolyte system that supports and supplies the anolyte from the electrochemical cell to the anolyte reaction chamber and back to the electrochemical cell.

FIG. 3 Catholyte System is a representation of a catholyte system that supports and supplies the catholyte from the electrochemical cell to the catholyte reservoir and back to the electrochemical cell.

FIG. 13E Fuel Cell Unit 297 is a schematic representation of a MEO system producing fuel for a Fuel Cell.

DETAILED DESCRIPTION OF PREFERRED EMBODIMENTS

General MEO System

The embodiments described in this patent use a MEO process in a unique MEO apparatus to process materials that may be liquids, solids, gases, or mixtures. The MEO apparatus is composed of the following systems: anolyte, catholyte, electrochemical cell, oxidizer suppression, dewatering, controller, off-gas, sensor and instrumentation, hydrogen, and safety. Each system is discussed in detail in the following sections, and figures are included to graphically depict the systems. For clarity, Table 3 Numbered Figure Components is included to identify each item in the figures.

Figure 1:
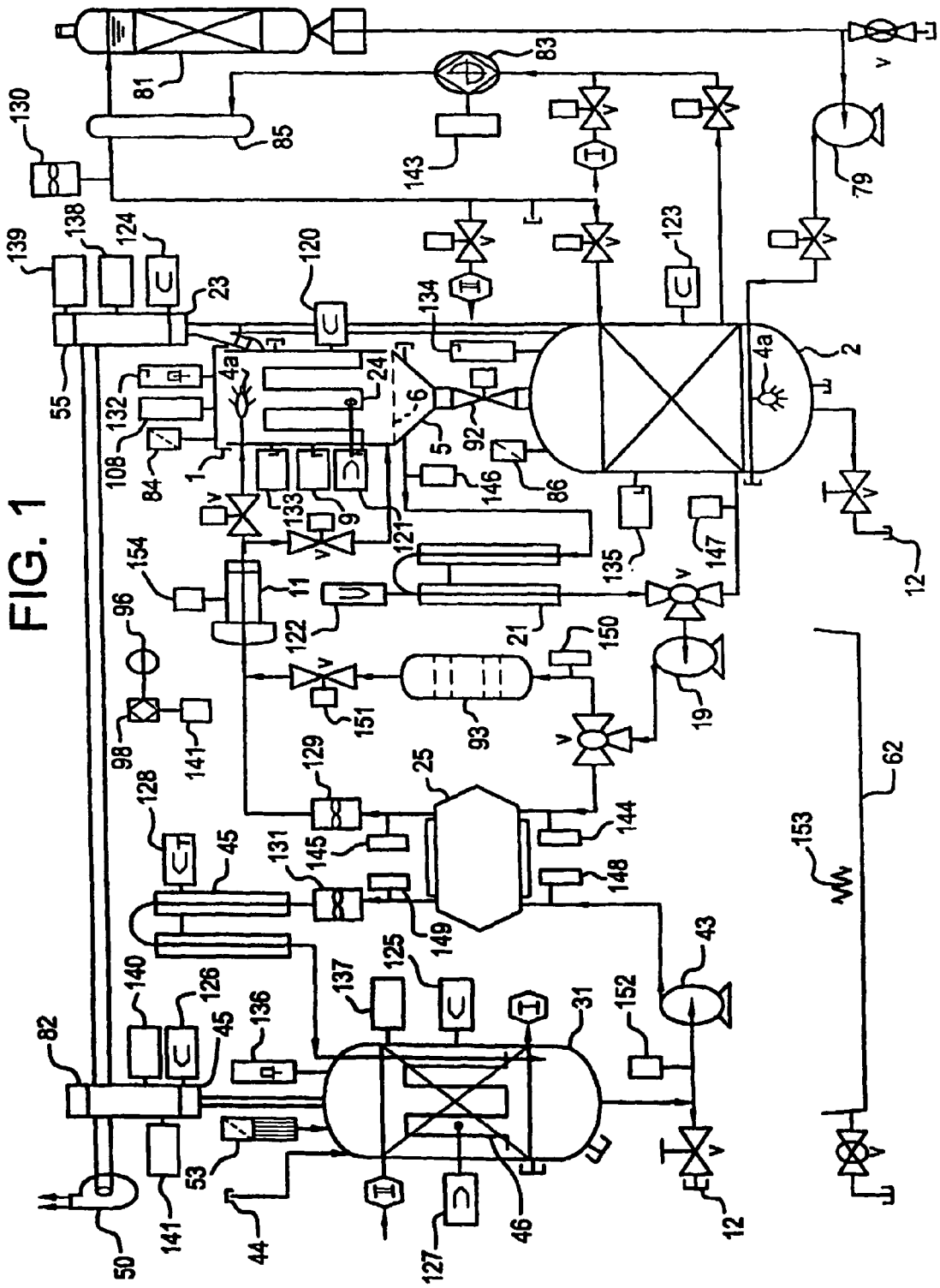
FIG. 1 MEO Apparatus Diagram 200 is a schematic representation of a system for oxidizing materials.

One detailed embodiment of a MEO apparatus is presented in FIG. 1 MEO Apparatus Diagram. This embodiment is not intended to be a comprehensive MEO apparatus but rather an illustration of an embodiment that includes a representative MEO apparatus with components from each of the various systems discussed in the later sections. The systems in FIG. 1 are integrated into the MEO apparatus and no attempt is made to group them as systems. The following sections will discuss each system and figures are referenced in those sections to illustrate the components in a system grouped together to facilitate the explanation of the operation of the systems.

The general characteristics of the MEO apparatus will be discussed in this section to lay the ground work for the more detailed discussions to follow. Unless otherwise stated, the components called out in this write-up are shown in FIG. 1.

The MEO apparatus contains two separate closed-loop systems, one containing an anolyte solution, and the other a catholyte solutions. These electrolyte solutions are circulated by pumps 19 and 43 in each of the two systems. The anolyte solution 203 and catholyte solution 207 are separated by a membrane 27 in the electrochemical cell 25, as illustrated in FIGS. 2 and 3, respectively. The basic design of the MEO apparatus permits the user to change the type of electrolyte without having to alter the equipment in the apparatus. The changing of the anolyte and catholyte solutions is accomplished by using the drains 12 to remove the electrolytes from the MEO apparatus. The replacement electrolytes are introduced usually directly into the anolyte reaction chamber 5 and the catholyte reservoir 31. The anolyte reaction chamber 5 is illustrated in FIG. 1 with a lid 1 without including the mechanical opening and closing mechanism. The anolyte reaction chamber 5 has many embodiments which are discussed and illustrated in a following section. The anolyte reaction chamber 5 may have a video camera 108 used to view the progress of the MEO process in the anolyte reaction chamber 5. The ability to change the type of electrolyte allows the user to tailor the MEO process to differing materials and properties. The anolyte and catholyte may be heated respectively by heaters 24 and 46. They may also be cooled by chillers 23 and 45 respectively.

The off-gas processing system handles the off-gases from the anolyte reaction chamber 5 (which is basically carbon dioxide and some oxygen) and the catholyte reservoir 31 (which is hydrogen for some catholytes).

The dewatering system removes the water generated from the destruction of the materials or associated with its introduction into the units, and stores it in the water storage tank 81 for disposal or reconstitution of the electrolytes. The clean water stored in the water storage tank 81 may be pumped by the clean water pump 79 either into the anolyte system 201 or the catholyte system 205 to restore anolyte solution 203 or catholyte solution 207 levels. The controller system 49 shown in FIG. 9A manages the operational cycles used in the MEO process (e.g., destruction cycle, cleaning cycle, etc.). Sensors are integrated throughout the MEO apparatus to provide information used to monitor and control the MEO process. See Table 4 for a listing of sensors and instrumentation. Typical of the components in the safety system is the containment pan 62 shown in FIG. 12.

Anolyte System

The anolyte system 201 shown in FIG. 2 contains the anolyte portion of the electrolyte and circulates the anolyte by pumps 19 through the electrochemical cell 25 on the anode 26 side of the membrane 27. The membrane 27 in the electrochemical cell 25 separates the anolyte portion and catholyte portion of the electrolyte. The anolyte solution 203 exits the electrochemical cell 25 and flows into the anolyte reaction chamber 5.

FIG. 2 does not illustrate an embodiment of the anolyte reaction chamber 5 but rather shows the interfaces into and out of the anolyte reaction chamber 5. Illustrations of the various embodiments of the anolyte reaction chamber are included in the section on anolyte reaction chambers.

The anolyte exits the anolyte reaction chamber 5 by pump 19 for recirculation to the electrochemical cell 25. The anolyte solution 203 flow to the electrochemical cell 25 is measured by flow meter 129. The output of the flow meter 129 is used to monitor and assess the status of the anolyte solution 203 circulation. The anolyte system contains ultrasonic 9 and ultraviolet 11 energy sources shown in FIG. 1 and in the section on anolyte reaction chambers.

Materials are introduced into the anolyte system 201 through the anolyte reaction chamber 5. Several embodiments of the anolyte reaction chamber are illustrated in the anolyte reaction chamber section.

The MEO system apparatus incorporates two methods that may control the rate of destruction of materials and/or the order in which specific molecular bonds are broken. In the first method the anolyte temperature is initially at or below the operating temperature and subsequently increased by the thermal controls 21 and 22 (shown in FIG. 2) until the desired operating temperature for the specific materials stream is obtained. In the second method the materials are introduced into the apparatus, at the operating temperature, with the electrochemical cell electric current limited to a value where in the concentration of electrochemically generated oxidizing species in the anolyte is limited to some predetermined value between zero and the maximum desired operating concentration for the materials stream. Subsequently, the electric current in the electrochemical cell 25 is increased using the DC power supply 29 (shown in FIGS. 2 and 3) and raising the current to the desired operating concentration. The AC power supply 30 uses external electrical power (i.e., 220v or 120v AC power) to provide the electrical energy to drive the DC power supply 29. The AC power supply 30 may also provide low voltage AC to the electrochemical cell 25.

The anolyte solution is composed of an aqueous solution of mediator species and electrolytes appropriate for the species selected. The MEO apparatus is operated within the temperature range from approximately slightly above 0° C. to slightly below the boiling point of the anolyte solution, (usually less then 100° C.). The anolyte reaction chamber can be operated at a temperature or temperature profile most conducive to the desired materials destruction rate (e.g., most rapid, most economical, etc.) while the electrochemical cell may be operated at temperature most conducive to oxidizer formation. The choice of acid, alkaline, or neutral salt electrolyte used in the anolyte solution is determined by the conditions in which the species may exist.

Considerable attention has been paid to halogens, especially chlorine and their deleterious interactions with silver mediator ions; however this is of much less concern or importance to this invention. The wide range of properties (e.g., oxidation potential, solubility of compounds, cost, etc.) of the mediator species claimed in this patent allows selection of a single or mixture of mediators which avoids this problem. This flexibility provides for selecting mediators and electrolytes that; a) avoid formation of insoluble compounds, b) allows easy recovery of the mediator from precipitated materials, and c) are sufficiently inexpensive so as to allow the simple disposal of the insoluble compounds as waste, while still maintaining the capability to oxidize (i.e., destroy) the materials economically.

The materials destruction process may be monitored by several electrochemical and physical methods. First, various cell voltages (e.g., open circuit, anode vs. reference electrode, ion specific electrode, oxidation reduction potential electrodes, etc.) yield information about the ratio of oxidized to reduced mediator ion concentrations which may be correlated with the amount of reducing agent (i.e., oxidizable materials) either dissolved in or wetted by the anolyte. FIG. 1 illustrates the use of ORP (oxidation reduction potential) sensors 144, 145, 146, 147, 148, 149, 150, and 151 to monitor the concentration of mediator ions. Second, if a color change accompanies the transition of the mediator species between it's oxidized and reduced states (e.g., heteropoly blues, etc.), the rate of decay of the color associated with the oxidized state, under zero current conditions, could be used as a gross indication of the amount of reducing agent (i.e., oxidizable materials) present. If no color change occurs in the mediator, it may be possible to select another mediator to simply serve as the oxidization potential equivalent of a pH indicator 152. Such an oxidation indicator is required to have an oxidation potential between that of the working mediator and the organic species, and a color change associated with the oxidization state transition. The ultraviolet light sensor 154 indicates that the ultraviolet source 11 is functioning properly.

Thermal control units 21 and 22 (shown in FIG. 2) are connected to the flow stream to heat or cool the anolyte to the selected temperature range. If warranted, an anolyte chiller 23 may be located upstream from the electrochemical cell 25 to lower the anolyte temperature within the cell to the desired level. Another anolyte heater 24 (shown in FIG. 1) may be located in or around the outside of the anolyte reaction chamber 5 inlet to control the anolyte temperature in the anolyte reaction chamber 5 to within the desired temperature range to affect the desired chemical reactions at the desired rates.

The oxidizer species population produced by electrochemical generation (i.e., anodic oxidation) of the oxidized form of the redox couples referenced herein can be enhanced by conducting the process at lower temperatures, thereby reducing the rate at which thermally activated parasitic reactions consume the oxidizer.

The MEO process proceeds until complete destruction of the materials has been affected or is modified to stop the process at a point where the destruction of the materials is incomplete. The reason for stopping the process is that: a) the materials are benign and do not need further treatment, or b) the materials may be used in the form they have been converted to and thus would be recovered for that purpose.

One embodiment of the MEO apparatus may use a liquefier 18. The liquefier 18 (the liquefier 18 is not shown in the Figures) emulsifies the materials introduced into the anolyte reaction chamber 5. The emulsification results in greatly increasing the area of contact between the materials and the MEO oxidizers during the MEO process and thus the materials destruction rate.

One embodiment of the MEO apparatus may use an anolyte make-up tank 91 (the anolyte make-up tank is not shown in the Figures). In the case where anolyte mediators pass through the membrane 27 to the catholyte side of the system, new anolyte may be injected into the anolyte system. The injection operation is initiated by an operator and is controlled through the controller system 49 shown in FIG. 9A (see the section on MEO Controller).

All surfaces of the apparatus in contact with the anolyte are composed of one or more of the following types of materials; a) nonreactive polymers (e.g., polytetrafluoroethylene (PTFE), etc), b) stainless steel coated with nonreactive polymers (e.g., PTFE, etc)) glass, or PTFE coated metallic tubing, d) glazed ceramics, e) glazed metallics, and f) glazed composites. These materials provide an anolyte containment boundary to protect the components of the MEO apparatus from being oxidized by the electrolyte.

Catholyte System

FIG. 3 Catholyte System 205 is representative of the catholyte portion of the MEO apparatus. The catholyte solution is circulated by pump 43 through the electrochemical cell 25 on the cathode 28 side of the membrane 27. The AC power supply 30 uses external electrical power (i.e., 220v or 120v AC power) to provide the electrical energy to drive the DC power supply 29. The catholyte solution flows into a catholyte reservoir 31 from the electrochemical cell 25. The catholyte chiller 45 and the catholyte heater 46 are connected to the catholyte flow stream to cool or heat the catholyte to the selected temperature range.

External air is introduced through an air sparge 37 into the catholyte reservoir 31 below the surface of the catholyte. Sensor 155 measures the air flow. Sensor 155 detects the air flow through the air sparge. In the case where nitrogen compounds (e.g., nitrates, etc.) are used in the catholyte, the oxygen contained in the air oxidizes any nitrites or nitrous acid produced by the cathodic reduction, preventing formation of nitrogen oxides (NO). Contact of the oxidizing gas with the reduced nitrogen compounds (nitrous acid) may be enhanced by using conventional techniques for promoting gas/liquid contact such as ultrasonic vibration 48, mechanical mixing 35, etc.

Figure 10:
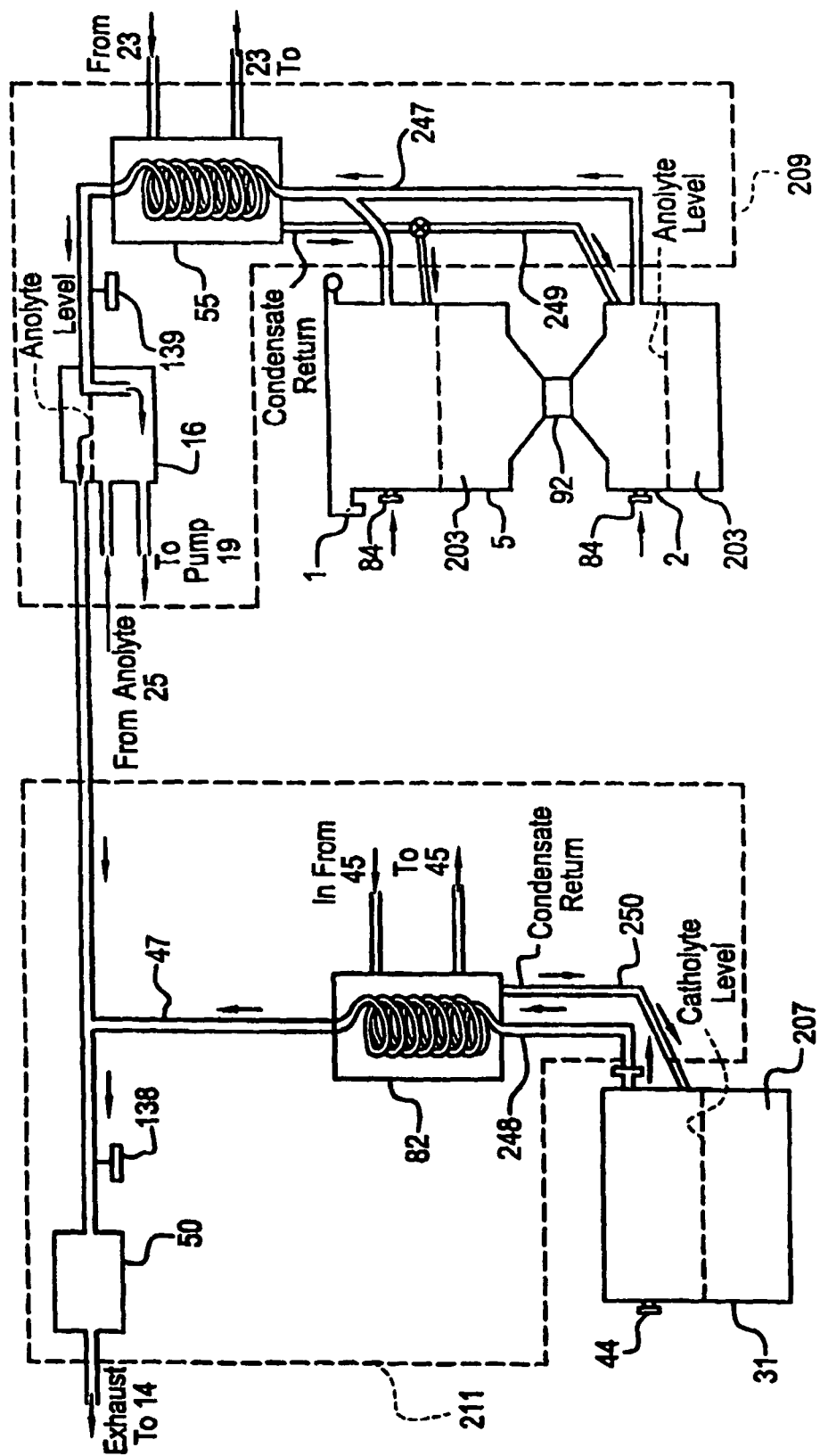
FIG. 10 Off-gas Processing System is a representation of the off-gas processing system for the anolyte and catholyte off-gases.

Systems using non-nitrate catholytes may also require air sparging to dilute and remove off-gas such as hydrogen. Room air enters the catholyte reservoir 31 through the catholyte air intake/filter 44 and exits the catholyte reservoir 31 to the catholyte off-gas handling system 211 (see FIG. 10). A catholyte off-gas handling system 211, shown in FIG. 10, is used to remove any unwanted gas products (e.g. $NO_2$, etc.). The cleaned gas stream, combined with the unreacted components of the air introduced into the system is discharged through the catholyte vent 47 shown in FIGS. 1, 10, 13B and 13C.

The anolyte recovery system 41 may be positioned on the catholyte side. Some mediator oxidizer ions may cross the membrane 27, and this option is available if it is necessary to remove them through the anolyte recovery system 41 to maintain process efficiency, or cell operability or their economic worth necessitates their recovery. Operating the electrochemical cell 25 at higher than normal membrane 27 current densities (i.e., above about 0.5 amps/cm$^2$ for Nafion™) increases the rate of materials destruction, but may result in increased mediator ion transport through the membrane 27 into the catholyte. It may be economically advantageous for the electrochemical cell 25 to be operated in this mode. It is advantageous whenever the replacement cost of the mediator species or removal/recovery costs are less than the cost benefits of increasing the materials throughput (i.e., oxidation rate) of the electrochemical cell 25. Increasing the capitol cost of expanding the size of the electrochemical cell 25 can be avoided by using this operational option.

All surfaces of the apparatus in contact with the catholyte are composed of acid and alkaline resistant materials. The anolyte solution 203 and the catholyte solution 207 may be removed from the MEO apparatus 200 by draining the solutions through drain 12. The catholyte reservoir 31 has a removable lid 33 that provides access to the interior of the catholyte reservoir 31.

Anolyte Reaction Chamber

The anolyte reaction chamber 5(s) referred to in FIGS. 1, 2, 4A, 4B, 4C, 4D, 4E, and 4F, is the central part of the anolyte system. The anolyte reaction chamber 5 is a flexible part of the overall MEO apparatus. The anolyte reaction chambers have different embodiments that are functions of the type and form of materials being processed. The following paragraphs present numerous forms of the embodiments of the anolyte reaction chambers 5.

Figure 4A:
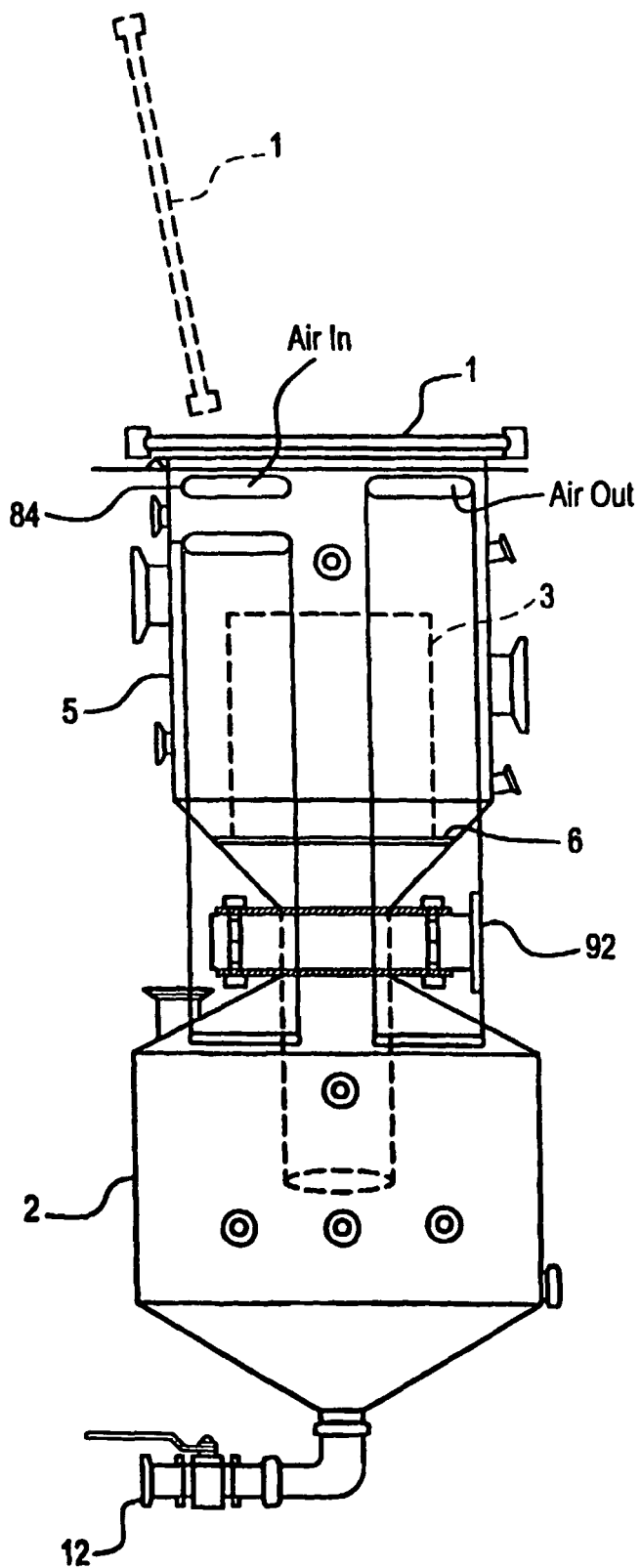
FIG. 4A Anolyte Reaction Chamber with Anolyte Reservoir is a representation of an anolyte reaction chamber with an anolyte reservoir attached. The reservoir holds the anolyte whenever the anolyte reaction chamber is accessed by an operator, maintenance is being performed, or the MEO apparatus is being cleaned.

In some embodiments the anolyte reaction chambers 5 have an anolyte reservoir 2 attached to the anolyte reaction chamber 5. FIGS. 1 and 4A depict this configuration. The anolyte reservoir 2 is connected to the anolyte reaction chamber 5 through a dump valve 92 (FIGS. 1 and 4A). Anytime the lid 1 to the anolyte reaction chamber 5 is opened for access, the dump valve 92 is opened prior to opening lid 1. The liquid contents of the anolyte reaction chamber 5 drops into the anolyte reservoir 2. The removal of the anolyte solution 203 from the anolyte reaction chamber 5 avoids the potential for the operator coming in to contact with the anolyte solution 203 during loading of the materials into the anolyte reaction chamber 5. The anolyte solution 203 in the anolyte reservoir 2 may be drained through the drain 12. The anolyte reaction chamber 5 may contain a waste basket 3 shown in FIGS. 4A, 4C and 4D to hold solids. Air may be drawn into the anolyte reaction chamber 5 through air intake filter 84 and air purged off gases through the anolyte off-gas handling system 209 (see FIG. 10).

FIG. 1 illustrates the use of an ultrasonic anolyte reaction chamber level sensor 132 to measure the amount of anolyte solution 203 in the anolyte reaction chamber 5. The anolyte reaction chamber 5 may have sensors 133 to detect overfill. The anolyte reservoir 2 may have an ultrasonic sensor 134 to measure the amount of anolyte solution 203 in the anolyte reservoir 2. Sensor 135 is used to measure whether the anolyte reservoir 2 is being filled beyond a recommended level (e.g., overfilled).

Figure 4B:
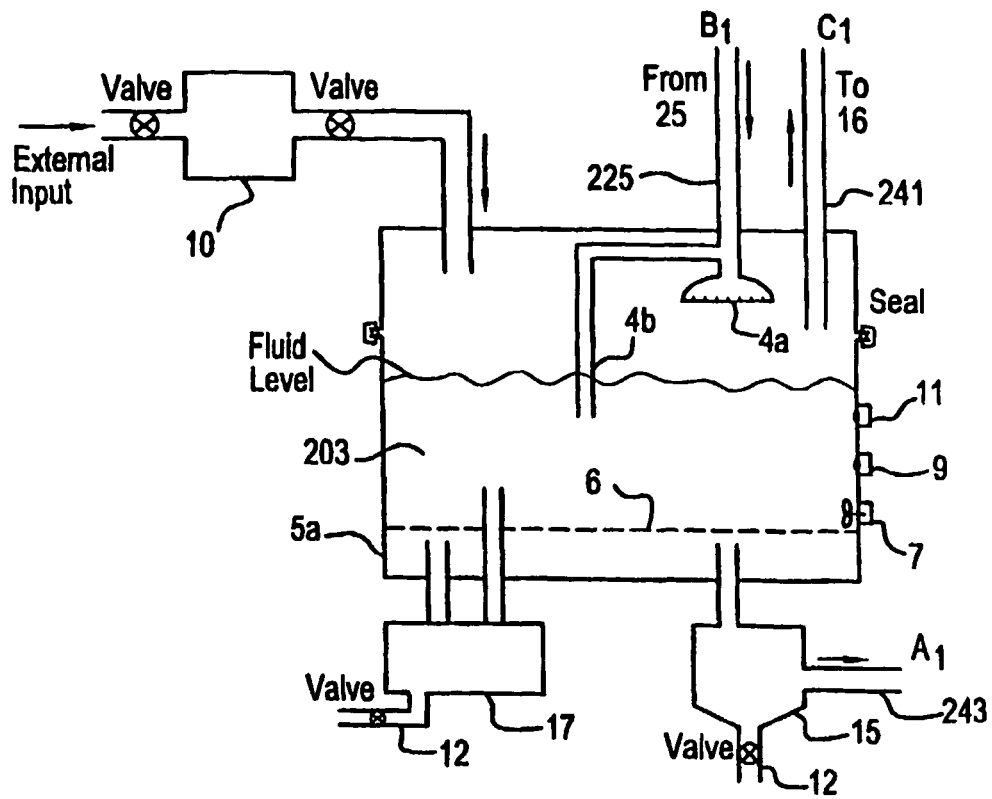
FIG. 4B Anolyte Reaction Chamber for Liquids, Mixtures, Small Particulate and with Continuous Feed is a schematic representation of an anolyte reaction chamber used for fluids, and mixtures which include small particulate matter. This chamber accommodates a continuous feed of these materials into the chamber.

The embodiment of the anolyte reaction chamber 5a in FIG. 4B is designed for liquids, small particulate matter and continuous feed operations. The materials are introduced into the anolyte reaction chamber 5a through the input pump 10 connected to the source of the materials to be destroyed. The materials are pumped into the chamber 5a, which contains the anolyte used to destroy these materials. The apparatus continuously circulates the anolyte solution 203 directly from the electrochemical cell 25 through inlet tube 225 into the anolyte reaction chamber 5a to maximize the concentration of oxidizing species contacting the materials. The anolyte is introduced into the anolyte reaction chamber 5a through the spray head(s) 4a and stream head(s) 4b. For simplicity we only show one of each type head, while in some applications multiple heads may be used. The two heads are designed to increase the exposure of the materials to the anolyte by enhancing the mixing in the anolyte reaction chamber 5a Introducing the anolyte solution 203 into the anolyte reaction chamber 5a as a spray onto the anolyte solution 203 surface promotes contact with (i.e., oxidation of) any immiscible materials present in surface layers. A filter 6 is located at the base of the anolyte reaction chamber 5a to limit the size of the solid particles flowing from anolyte reaction chamber 5a to approximately 1 mm in diameter (i.e., smaller that the minimum dimension of the anolyte flow path in the electrochemical cell 25), thereby preventing solid particles large enough to interfere with the flow in the electrochemical cell 25 from exiting the anolyte reaction chamber 5a.

Contact of the oxidizing species with solid or liquid immiscible liquid materials, or incomplete oxidation products that are solid, immiscible liquid, or gaseous at the conditions within the anolyte reaction chamber 5a may be further enhanced by using conventional techniques for promoting such contact (e.g., ultrasonic vibration 9, mechanical mixing 7). An ultraviolet source 11 is introduced into the anolyte reaction chamber 5a to decompose the hydrogen peroxide formed by the MEO process into free hydroxyl radicals. Gaseous products resulting from the MEO process in the anolyte solution 203 may exit the anolyte reaction chamber 5a through the tube to anolyte off-gas system 241. The anolyte off-gas is processed in the gas cleaning system 16. The anolyte solution 203 returns to the anolyte pump 19 in the anolyte system 201 through tube 243.

The anolyte solution 203 may be removed from the anolyte system 201 by draining the solutions through drain 12. An inorganic removal system 15 (e.g., filter, centrifuge, hydrocyclone, etc,) is shown in FIGS. 4B, 4C, 4D, and 4E. The inorganic removal system 15 is used to remove any oxidized insoluble compounds that form as a result of mediator or electrolyte ions reacting with anions of or containing halogens, sulfur, phosphorous, nitrogen, etc. that may be present in the materials stream thus preventing formation of unstable compounds (e.g., perchlorates, etc.). The residue of the oxidized insoluble compounds is removed out of the inorganic removal system 15 during periodic maintenance if necessary. If warranted, the oxidized insoluble compounds are converted to water-soluble compounds using any one of several chemical or electrochemical processes. The anolyte is then returned to the electrochemical cell 25, where the oxidizing species are regenerated, which completes the circulation in the anolyte system.

The organic compounds removal system 17 (shown in FIGS. 4B, 4C, 4D, and 4E) is used to perform the removal of organic compounds in a process similar to that discussed for the inorganic compounds removal system 15.

Figure 4C:
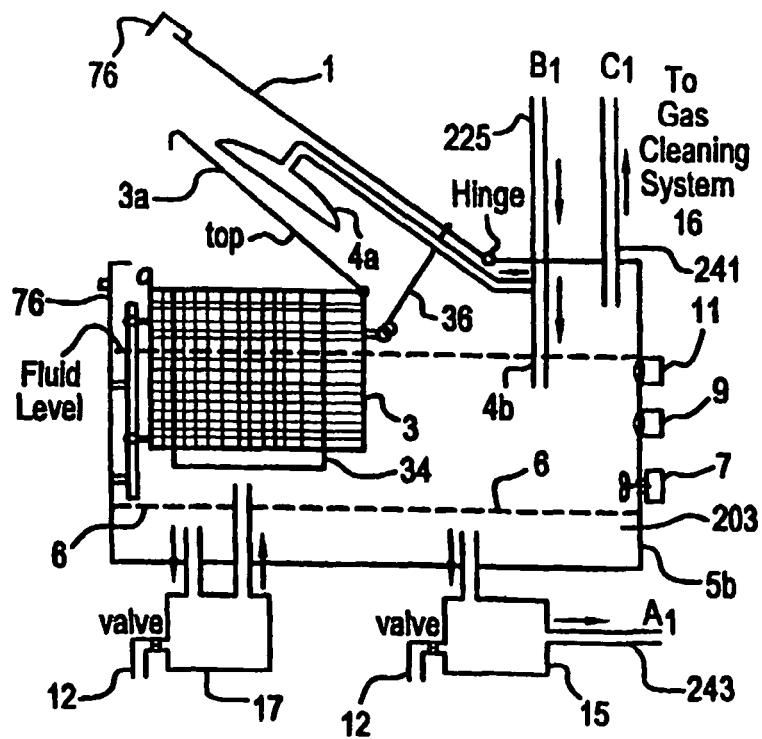
FIG. 4C Anolyte Reaction Chamber for Solids, Mixtures, and Larger Particulate and with Batch Operation is a schematic representation of an anolyte reaction chamber used for solids, and mixtures that include large particulate. This chamber may be used for batch mode processing of materials.

The embodiment of the anolyte reaction chamber 5b in FIG. 4C is designed for solids, mixtures and batch operations. The hinged lid 1 is lifted, and the top 3a of the basket 3 is opened. The materials are introduced into the basket 3 in the anolyte reaction chamber 5b where the solid materials remain while the liquid portion of the materials flows into the anolyte solution 203. The basket top 3a is closed, and as lid 1 is closed the basket 3 is lowered by a lever 36 connected to the lid 1 into the anolyte solution 203 such that all its contents are held submerged in the anolyte solution 203 throughout the oxidization process. Lid 1 has a seal around the opening and it is locked by locking latch 76 before operation begins.

A mechanical device (penetrator 34) incorporated into the basket 3 create multiple perforations in the outer layers of the solid materials so that the anolyte solution 203 can penetrate into the materials. This penetration speeds up the oxidation of the solid materials by increasing the surface area exposed to the anolyte oxidizer, and allowing said oxidizer immediate access to portions of the aforementioned materials that are encased in (i.e., protected by) more difficult to oxidize surrounding outer layers.

The apparatus continuously circulates the anolyte solution 203 directly from the electrochemical cell 25 through the anolyte reaction chamber 5b to maximize the concentration of oxidizing species contacting the materials. The anolyte solution 203 enters the anolyte reaction chamber 5b through inlet tube 225 and is injected through two types of nozzles. The first, a spray head 4a distributes the anolyte solution 203 throughout the anolyte reaction chamber 5b and on the surface. The second is a stream head 4b located below the surface of the anolyte solution 203 to promote circulation and turbulence in the anolyte reaction chamber 5b. For simplicity we only show one of each type head, while in some applications multiple heads may be used. Introducing the anolyte into the anolyte reaction chamber 5b as a spray onto the anolyte surface promotes contact with (i.e., oxidation of) any immiscible material surface layers present. Anolyte off-gas exits the anolyte reaction chamber through tube to anolyte off-gas system 241 to the gas cleaning system 16.

The filter 6 is located at the base of the anolyte reaction chamber 5b to limit the size of the solid particles to approximately 1 mm in diameter (i.e., smaller that the minimum dimension of the anolyte flow path in the electrochemical cell 25) thereby preventing solid particles large enough to interfere with the flow in the electrochemical cell 25 from exiting the anolyte reaction chamber 5b. Contact of the oxidizing species with solid or liquid immiscible liquid materials, or incomplete oxidation products that are solid, immiscible liquid, or gaseous at the conditions within the anolyte reaction chamber 5b may be further enhanced by using conventional techniques for promoting such contact (e.g., ultrasonic vibration 9, mechanical mixing 7). An ultraviolet source 11 is introduced into the anolyte reaction chamber 5b to decompose the hydrogen peroxide formed by the MEO process into free hydroxyl radicals. The anolyte solution 203 returns to the anolyte pump 19 in the anolyte system 201 through tube 243.

The anolyte solution 203 may be removed from the anolyte system 201 by draining the solutions through drain 12. Inorganic and organic materials may be removed from the anolyte solution 203 by the inorganic removal system 15 and organic removal system 17 which were discussed in previous section relative to FIG. 4B.

Figure 4D:
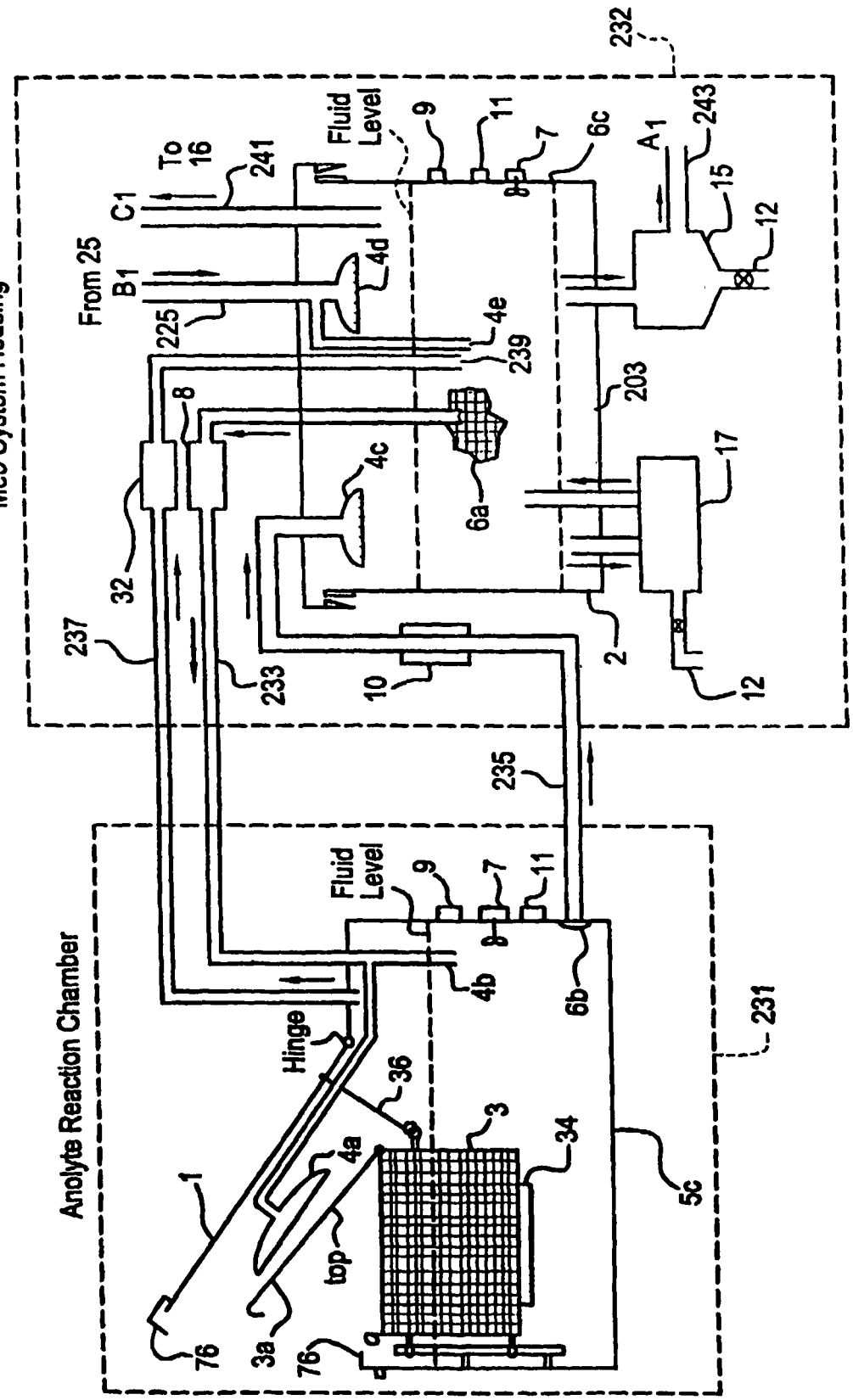
FIG. 4D Remote Anolyte Reaction Chamber is a schematic representation of the anolyte reaction chamber used for separating the anolyte reaction chamber from the basic MEO system housing. This configuration allows the chamber to be a part of a production line or similar use.

The embodiment of the anolyte reaction chamber 5c in FIG. 4D is designed to use an anolyte reaction chamber 5c in a separate housing 231 that is exterior to the basic MEO apparatus in MEO system housing 232. Typical of this configuration is an apparatus that is similar to an ultrasonic bath. The chamber may be integrated into a production process to be used to destroy materials as a part of the industrial process. The chamber may be connected to the basic MEO system housing 232 through tubing 233, 235, 237 and pumps 8, 10, 32. The anolyte solution 203 enters the anolyte reservoir 2 from the electrochemical cell 25 through tube 225 into spray head 4d and stream head 4e. The anolyte solution 203 returns from the anolyte reservoir 2 through tube 243 to the anolyte pump 19. The anolyte solution 203 is pumped from the anolyte reservoir 2 in the basic MEO system housing 232 by the pump 8 through tubing 233 where it is introduced into the anolyte reaction chamber 5c through both the spray head(s) 4a and stream head(s) 4b. The spray head 4a sprays anolyte solution 203 onto the anolyte surface thereby promoting contact with (i.e., oxidation of) any immiscible materials surface layers present in addition to reacting with (i.e., oxidizing) the materials dissolved, suspended or submerged within the anolyte in the anolyte reaction chamber 5c.

In anolyte reservoir 2 the inlet to pump 8 is protected by an in-line screen filter 6a which prevents solid particles large enough to interfere with the both the flow in the spray head(s) 4a and stream head(s) 4b from exiting the anolyte reservoir 2 through anolyte input tube 233 to anolyte reaction chamber 5c.

Contact of the oxidizing species with solid or liquid immiscible liquid materials, or incomplete oxidation products that are solid, immiscible liquid, or gaseous at the conditions within the anolyte reaction chamber 5c may be further enhanced by using conventional techniques for promoting such contact (e.g., ultrasonic vibration 9, mechanical mixing 7). an ultraviolet source 11 is introduced into anolyte reaction chamber 5c and anolyte reservoir 2, to decompose the hydrogen peroxide formed by the MEO process into free hydroxyl radicals. The input pump 10 pumps the anolyte solution 203 and liquid materials in the anolyte reaction chamber 5c back to the anolyte reservoir 2 in the basic MEO apparatus through the anolyte exit tube 235 from the anolyte reaction chamber 5c protected by an in-line screen filter 6b in anolyte reaction chamber 5c which prevents solid particles large enough to interfere with the flow in the spray head(s) 4c from exiting the anolyte reaction chamber 5c. A third tube is connected to the anolyte reaction chamber 5c to pump out any gas that is present from the original contents or from the MEO process. The gas is pumped by the air pump 32 through the anolyte off-gas exit tube 237. The return gas tube outlet 239 is submerged in the anolyte reservoir 2 in the basic MEO system so as to oxidize any volatile organic compounds in the gas to $CO_2$ before release of the gas in anolyte reservoir 2 through tube to anolyte off-gas system 241 to the gas cleaning system 16. The apparatus continuously circulates the anolyte solution 203 directly from the electrochemical cell 25 and through the anolyte reservoir 2 and through tubes 233 and 235 to anolyte reaction chamber 5c to maximize the concentration of oxidizing species contacting the materials.

The hinged lid 1 on anolyte reaction chamber 5c is lifted, and the basket top 3a of the basket 3 is opened. The materials are introduced into the materials basket 3 in the anolyte reaction chamber 5c where the solid materials remains while the liquid portion of the materials flows into the anolyte. The basket top 3a and the lid 1 are closed. Lid 1 has a seal around the opening, and it is locked by lock 76 before operation begins. With basket lid 3a closed, the basket 3 is lowered by a lever 36 into the anolyte so that all its contents are held submerged in the anolyte throughout the oxidization process.

A mechanical device penetrator 34 may be incorporated into the basket 3 in the anolyte reaction chamber 5c that create multiple perforations in the outer portion of the solid materials so that the anolyte can rapidly penetrate into the interior of the materials. The penetrator 34 serves the same purpose it does in the anolyte reaction chamber 5b described in the foregoing section. A filter 6c is located at the base of the anolyte reservoir 2 to limit the size of the solid particles to approximately 1 mm in diameter (i.e., smaller that the minimum dimension of the anolyte flow path in the electrochemical cell 25) thereby preventing solid particles large enough to interfere with the flow in the electrochemical cell 25 from exiting the anolyte reservoir 2 through tube 243.

The anolyte from the electrochemical cell 25 is introduced into the anolyte reservoir 2 through tube 225, spray head 4d and stream head 4e. For simplicity we only show one of each type head while in some applications multiple heads may be used. The two heads are designed to increase the exposure of the materials to the anolyte solution 203 by enhancing the mixing in the anolyte reservoir 2. Introducing the anolyte solution 203 into the anolyte reservoir 2 as a spray onto the anolyte surface promotes contact with (i.e., oxidation of) any immiscible surface layers present. Anolyte off-gas exits the anolyte reaction chamber through tube to anolyte off-gas system 241 to the gas cleaning system 16.

The MEO apparatus in the MEO system housing 232 continuously circulates the anolyte portion of the electrolyte directly from the electrochemical cell 25 into the anolyte reservoir 2 to maximize the concentration of oxidizing species contacting the materials in anolyte reaction chamber 5 and anolyte reservoir 2. A filter 6c is located at the base of the anolyte reservoir 2 to limit the size of the solid particles to approximately 1 mm in diameter (i.e., smaller than the minimum dimension of the anolyte flow path in the electrochemical cell 25). The anolyte solution 203 returns to the anolyte pump 19 in the anolyte system 201 through tube 243.

The anolyte solution 203 may be removed from the anolyte system 201 by draining the solutions through drain 12. Inorganic and organic materials may be removed from the anolyte solution 203 by the inorganic removal system 15 and organic removal system 17 which were discussed in previous section relative to FIG. 4B.

Figure 4E:
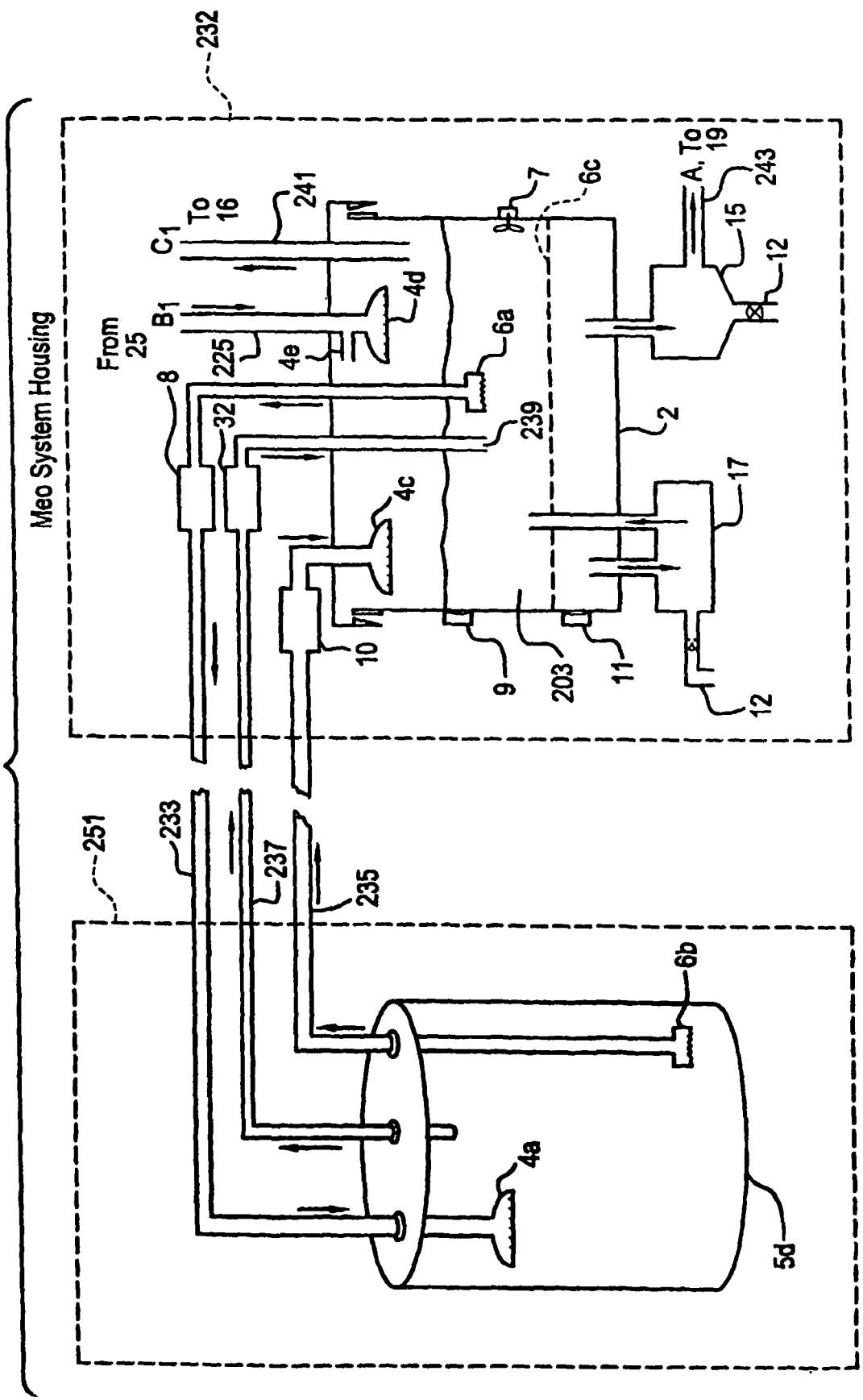
FIG. 4E Contaminated Equipment Used as the Anolyte Reaction Chamber Exterior is a schematic representation of a contaminated container serving the role of the anolyte reaction chamber that is not a part of the MEO system housing. Typical examples of contaminated containers are a) storage tanks for liquids, and b) metallurgical plating baths. This configuration is used to decontaminate items and clean them for future use or disposal.

The embodiment of the anolyte reaction chamber 5d in FIG. 4E is designed to use as a closed container 5d in an exterior housing 251 to the basic apparatus in the MEO system housing 232. The container is the anolyte reaction chamber 5d. FIG. 4E illustrates one example of an exterior container, which in this case is a metal vessel such as a 55-gallon steel drum containing materials. The drum may be connected to the basic MEO apparatus through tubing 233, 235, 237, and pumps 8, 10, 32. The anolyte solution 203 is pumped by the pump 8 from the anolyte reservoir 2 in the basic MEO system housing 232 through tube 233 into the anolyte reaction chamber 5d where it reacts with the contents and oxidizes the materials. The tube 233 through which anolyte solution 203 is pumped by pump 8 is protected by an in-line screen filter 6a which prevents solid particles large enough to interfere with the flow in spray head 4a from exiting the anolyte reservoir 2. The anolyte stream is oscillated within the anolyte reaction chamber 5d to thoroughly wash down/clean all interior surfaces and promote thorough mixing of any waste with the anolyte solution 203. The input pump 10 pumps the anolyte solution 203 and liquid materials in the anolyte reaction chamber 5d back to the anolyte reservoir 2 in the basic MEO system housing 232 through a anolyte exit tube 235 protected by an in-line screen filter 6b which prevents solid particles large enough to interfere with the flow in the spray head 4c from exiting the anolyte reaction chamber 5d. The anolyte off-gas exit tube 237 is connected to the anolyte reaction chamber 5d through the air pump 32 to pump out any gas that is present in anolyte reaction chamber 5d from the original contents or from the MEO process. The return gas tube outlet 239 is submerged below the anolyte solution 203 level in the anolyte reservoir 2 in the basic MEO system housing 232 so as to oxidize any volatile organic compounds in the gas to $CO_2$ before release through tube to anolyte off-gas system 241 to the gas cleaning system 16.

The anolyte solution 203 from the electrochemical cell 25 is introduced into the anolyte reservoir 2 through tube 225 the spray head 4d and stream head 4e. For simplicity we only show one of each type head while some applications multiple heads are used. The two heads are designed to increase the exposure of the materials to the anolyte by enhancing the mixing in the anolyte reservoir 2. Introducing the anolyte solution 203 into the anolyte reservoir 2 as a spray onto the anolyte surface promotes contact with (i.e., oxidation of) any immiscible surface layers present.

The MEO apparatus continuously circulates the anolyte portion of the electrolyte directly from the electrochemical cell 25 into the anolyte reservoir 2 to maximize the concentration of oxidizing species contacting the materials. A filter 6c is located at the base of the anolyte reservoir 2 to limit the size of the solid particles in tube 243 to approximately 1 mm in diameter (i.e., smaller than the minimum dimension of the anolyte flow path in the electrochemical cell 25). Contact of the oxidizing species with solid or liquid immiscible liquid materials, or incomplete oxidation products that are solid, immiscible liquid, or gaseous at the conditions within the anolyte reaction chamber 5d may be further enhanced by using conventional techniques for promoting such contact (e.g., ultrasonic vibration 9 and mechanical mixing 7). An ultraviolet source 11 is introduced into the anolyte reservoir 2 to decompose the hydrogen peroxide formed by the MEO process into free hydroxyl radicals. The anolyte solution 203 returns to the anolyte pump 19 in the anolyte system 201 through tube 243.

The anolyte solution 203 may be removed from the anolyte system 201 by draining the solutions through drain 12. Inorganic and organic materials may be removed from the anolyte solution 203 by the inorganic removal system 15 and organic removal system 17 which were discussed in previous section relative to FIG. 4B.

Figure 4F:
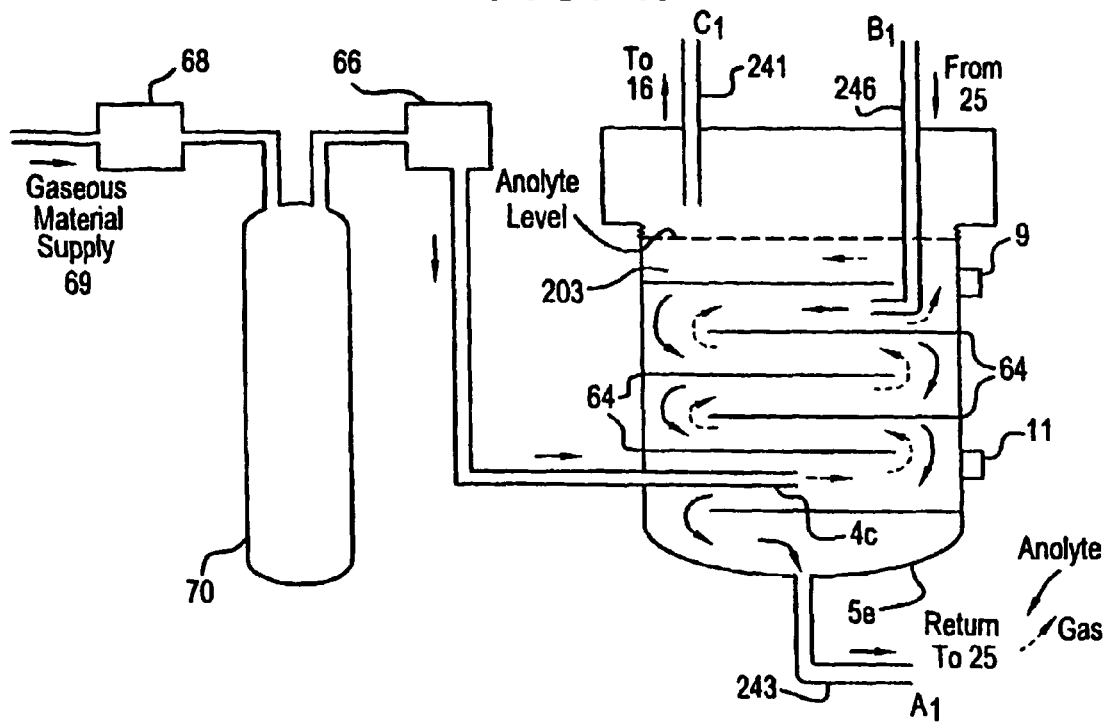
FIG. 4F Anolyte Reaction Chamber for Gaseous Materials is a schematic representation of a generic anolyte reaction chamber used for oxidizing gaseous materials. This chamber employs any practical methodology for promoting enhanced liquid gas contact (e.g., packed bed, etc.) and allows continuous introduction of waste and anolyte in a counter current flow pattern.

The embodiment of the anolyte reaction chamber 5e in FIG. 4F is designed for gaseous materials and continuous feed operations. The gaseous materials to be processed are introduced from the gaseous material supply 69 through the gaseous material supply system 299. The gaseous materials are pumped 68 into a pressure vessel 70. The regulator 66 on the pressure vessel 70 controls the release of the materials into anolyte reaction chamber 5e, which contains the anolyte solution 203 used to destroy these materials. The gaseous materials enter the anolyte reaction chamber 5e through a bubble heads 4c which assures the gas entering gas stream is in the form of small bubbles to create a large surface area on which the anolyte may act to oxidize the gaseous materials.

In one embodiment, the gaseous material contacts the anolyte solution 203 in a counter current flow. The gaseous materials are introduced into the lower portion of the anolyte reaction chamber 5e through a gaseous materials supply system 299 which contains a pressure vessel 70 and a pressure regulator 66. A stream of freshly oxidized anolyte solution 203 directly from the electrochemical cell 25 is introduced into the upper portion of the anolyte reaction chamber 5e through inlet tube 225. This results in the gaseous materials continuously reacting with the oxidizing mediator species in the anolyte solution 203 as the gas rises up the anolyte reaction chamber 5e past the downward flowing anolyte. Under these conditions the gaseous materials reaching the top of the anolyte reaction chamber 5e may have the lowest concentration of oxidizable species and may also be in contact with the anolyte solution 203 having the highest concentration of oxidizer species. The anolyte reaction chamber 5e contains a set of baffles 64 (schematically shown in FIG. 4F) that regulate the progress of the gaseous materials through the anolyte solution 203 in the anolyte reaction chamber 5e.

In other embodiments the gas-liquid contact within the anolyte reaction chamber 5e may be promoted by a number of well established methods {e.g., packed column (fiberglass, rotating discs, etc,} that will not result in any meaningful backpressure within the anolyte flow system. The basic purpose of the various methods used in the anolyte reaction chamber 5e is to lengthen the time the gaseous materials are within contact with the anolyte solution 203 and/or increase the area of contact between the waste and anolyte solution 203.

The apparatus continuously circulates the anolyte solution 203 directly from the electrochemical cell 25 through a tube from the electrochemical cell 246 to the anolyte reaction chamber 5e to maximize the concentration of oxidizing species contacting the materials. The anolyte solution 203 exits the anolyte reaction chamber 5e through a tube to anolyte pump 243 returning to the electrochemical cell 25. Gaseous products resulting from the MEO process in the anolyte solution 203 may exit the anolyte reaction chamber 5e through the tube to anolyte off-gas system 241. The anolyte off-gas is processed in the gas cleaning system 16.

Contact of the oxidizing species with incomplete oxidation products that are gaseous at the conditions within the anolyte reaction chamber 5e may be further enhanced by using conventional techniques for promoting gas/liquid contact (e.g., ultrasonic vibration 9). An ultraviolet source 11 is introduced into the anolyte reaction chamber 5e to decompose the hydrogen peroxide formed by the MEO process into free hydroxyl radicals.

In another embodiment, such methodologies could be used in series with the previously described system as a polishing process treating the gaseous discharge (using a gas cleaning system 16) from the countercurrent anolyte reaction chamber, or if advantageous, instead of it.

Catholyte Reservoir

Figure 5:
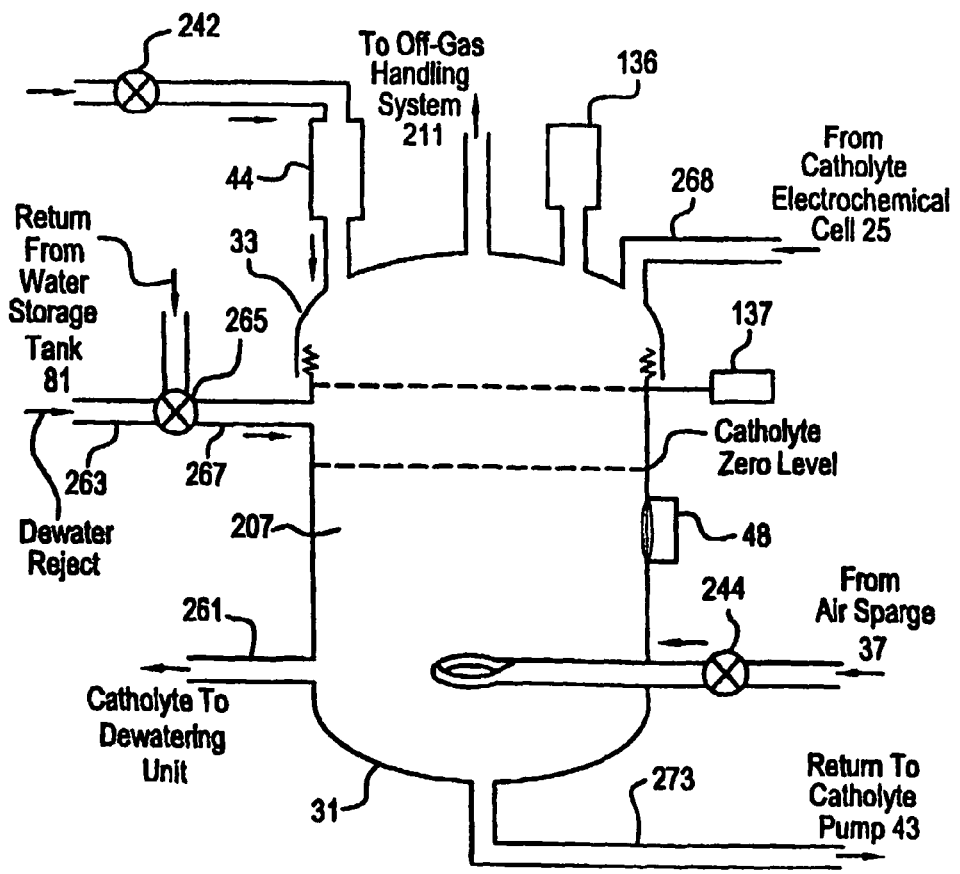
FIG. 5 Catholyte Reservoir is a representation of a catholyte reservoir used in the catholyte system.

FIG. 5 Catholyte Reservoir is representative of the design of a catholyte reservoir 31 in an MEO apparatus 200 (see FIG. 1). The bulk of the catholyte solution 207 is resident in the catholyte reservoir 31. The catholyte reservoir 31 interior can be accessed through the catholyte reservoir lid 33. The catholytes used in the MEO process are selected from acids, alkalines, and neutral solutions The catholyte reservoir 31 is made from such materials as metals, metal composites, fiberglass, glass, and ceramics. The surface of the catholyte reservoir 31 is coated with materials such as Teflon™, glass, metal oxides, and ceramic glazes.

The catholyte solution 207 enters the catholyte reservoir from the tube 268 from the electrochemical cell 25 to the catholyte reservoir. The catholyte solution 207 exits the catholyte reservoir through the tube 273 to the catholyte pump 43. Air is introduced into the catholyte reservoir 31 for several reasons. First, the air is used to dilute hydrogen gas that is formed at the cathode 28 for catholytes where production of hydrogen is thermodynamically favored. The air intake valve 242 is opened to provide air that flows through the air intake filter 44 into the catholyte reservoir 31. The air mixed with the catholyte off-gas exits out the tube to the catholyte off-gas handling system 211. The second, external air is introduced through an air sparge 37 into the catholyte reservoir 31 below the surface of the catholyte to prevent formation of hazardous off-gases (e.g., $NO_x$) by oxidation of their precursors (e.g., nitrous acid) back to the catholyte's stable composition (e.g., nitric acid). The air sparge valve 244 is opened to allow external air to enter through the air sparge 37.

The catholyte reservoir 31 may have an ultrasonic sensor 136 to measure catholyte solution 207 levels in the catholyte reservoir 31. The catholyte reservoir 31 may have sensors 137 to detect overfill due to water migration from the anolyte solution 203 through the electrochemical cell 25 to the catholyte solution 207.

The level of catholyte solution 207 is controlled by dewatering the catholyte solution 207 when it exceeds the level set in the sensor. The level of catholyte solution 207 is adjusted by flowing the catholyte solution 207 through catholyte dewatering tube 261 and the dewatered catholyte back through dewater reject tube 263. Valve 265 controls liquid flowing through tube 267 for the adding of returned catholyte or reject water makeup from the water storage tank 81. The catholyte reservoir 31 may have an ultrasonic source 48 to promote mixing and certain chemical reactions in the catholyte solution 207.

Electrical Power System

All embodiments of the MEO apparatus 200 have AC 30 and DC 29 power supplies to drive many of the components in the system, as shown in FIGS. 2 and 3. The power is provided by a power cord 78 (as seen in FIGS. 13A, 13B, 13C and 13E) connected to an external source of AC power 30 which may be 100v or 220v or higher depending the overall power usage of the MEO apparatus 200. An internal power supply converts the AC power 30 to DC power 29 for internal usage and/or may produce high current low voltage AC. The power supplies may be contained in a NEMA box that is pressurized with nitrogen gas. Other electrical components are also placed in the NEMA box. Using the NEMA box protects from a possible hydrogen leak causing problem resulting from a spark generated by the electrical equipment being used in the MEO apparatus 200. The flow regulating valves are pneumatically controlled for an additional level of reliability by avoiding any corrosion and safety issues when in the hydrogen generation mode.

In another embodiment, the electrical system components may be isolated from the anolyte system 201 and catholyte system 205 by using a bulkhead between the systems. In this configuration, the electrical system compartment contains an air intake and an exhaust port. The air is forced into of the compartment resulting in a slightly positive pressure. This positive pressure does not allow gases associated with the other systems to enter the compartment.

Electrochemical Cell

Typical electrochemical cells available on the market today are traditional plate and frame filter press type designs, where the electrodes are stacked together in a vertical plane sandwich like construction. The electrodes are separated by ion selective semi permeable membranes (e.g., Nafion™) and spacers (e.g., PTFE). The end plates held together by bolts that are torqued to the desired pressure to contain the electrolyte in its flow through the electrochemical cell. All surfaces in the electrochemical cell that come into contact with the electrolyte, are usually polyvinylidene fluoride (PVDF), polypropylene (PP), ethylene-chlorotrifluoroethylene (Halar), or polytetrafluoroethylene (PTFE). Typical of the current state-of-the-art is the configurations and materials covered in U.S. Pat. No. 6,368,740 and commercial cells made by ICI and ElectroCell ABB which are plate and frame designs. The plate and frame design has numerous potential maintenance problems. There is also an electrochemical cell defined in U.S. Pat. Nos. 5,707,508 and 5,756,874, similar to a sealed storage battery, specializing in processing liquids.

New unique designs for the electrochemical cells are introduced in this patent for various embodiments of the NEO apparatus 200, and any other appropriate application. The unique features presented in the following section include but are not limited to; design, materials, cost of construction, and maintenance. The embodiments of the electrochemical cell discussed in this section are used to present the basic design of the electrochemical cell. These embodiments are scalable and are depicted in the figures in their smaller configurations. The electrochemical cell embodiments may vary in size from a few hundred watts to over hundreds of kilowatts of electrical energy. These embodiments have the advantage of being designed to be fabricated in single units or assembled in banks of several electrochemical cells (multiple cells) operating in parallel. The MEO apparatus 200 embodiments that use the multiple cells provide for the MEO apparatus 200 to continue to operate while one or more of the multiple cells are taken off line and serviced. The MEO apparatus 200 are flexible in that more cells may be added to the MEO apparatus 200 in the field thus increasing its throughput without requiring a new MEO apparatus 200. These embodiments of the electrochemical cells also provide for the addition of more electrodes 26 and 28 and membranes 27 and 27a without having to replace or expand other components of the MEO apparatus 200.

Figure 6A:
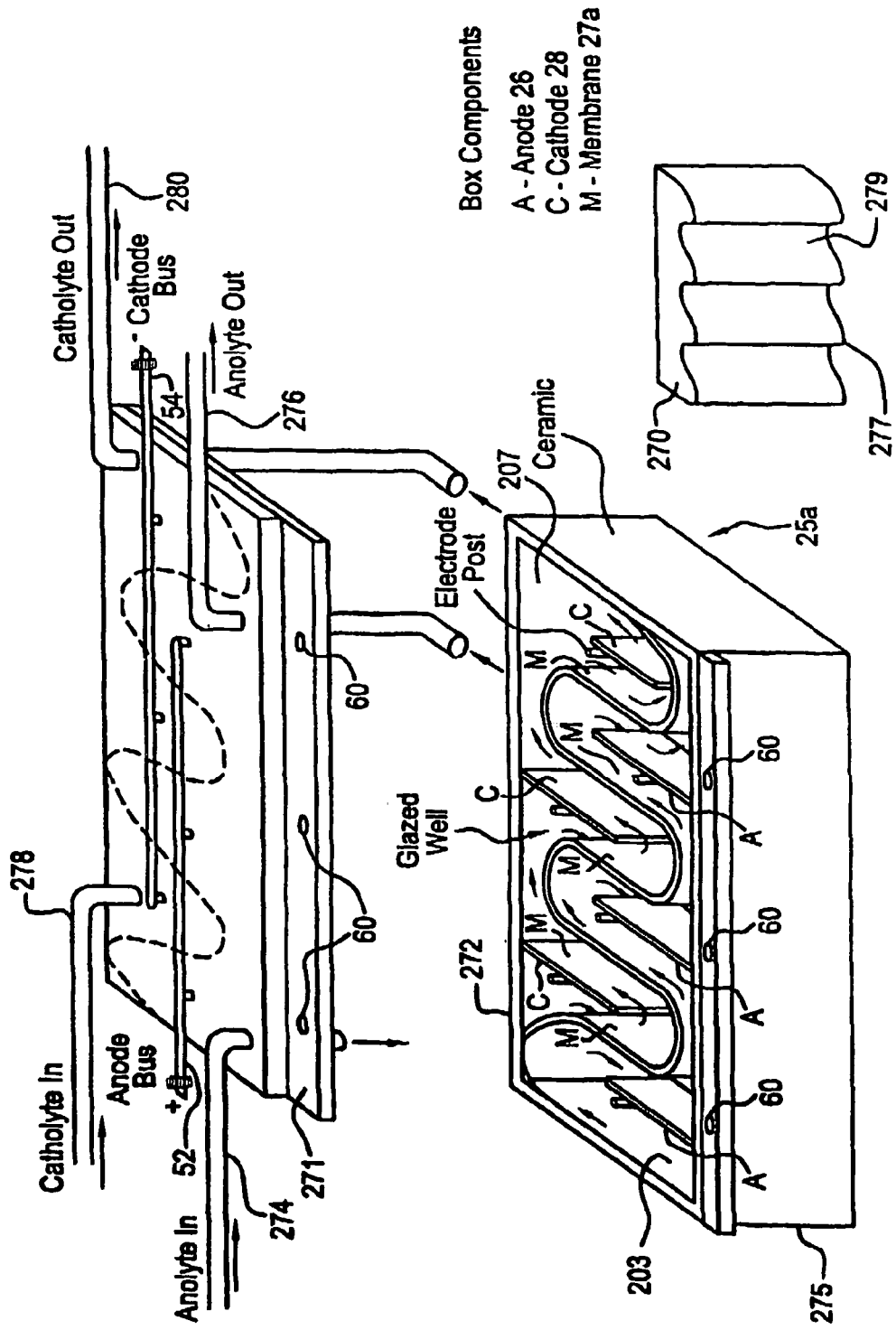
FIG. 6A Ceramic Box and Lid Electrochemical Cell is a representation of a ceramic box with ceramic lid style electrochemical cell.

The first embodiment of an electrochemical cell 25a is a ceramic box 270 and lid 271 styles, shown in FIG. 6A. Anolyte solution 203 enters the electrochemical cell 25a through the lid 271 by tubing 274, from the pump 19 and exits through tubing 276. Catholyte solution 207 enters the electrochemical cell 25a through input tubing 278 from pump 43 and exits through output tubing 280 in the lid. The entrance and exiting through the lid eliminates the source of leakage in the current designs. The box 270 is made of a molded ceramic as a unibody construction which is significantly less expensive to construct than the current state-of-the-art. The lid 271 is clamped to the box using nuts and bolts with the bolts passing through clamp holes 60. The lid 271 includes a gasket 272 thereby creating a liquid tight seal. The ease of access to the interior of the electrochemical cell 25a significantly improves the maintenance of the electrochemical cell 25a. The inside surfaces of the ceramic box 270 and the lid 271 are glazed to protect the ceramic walls from the oxidizer in the anolyte solution 203 and the acids or alkaline in the catholyte solution 207. The interior of the ceramic box 270 has walls that separate the anolyte solution 203 from the catholyte solution 207. Some of these interior walls separating the electrolytes serve as ion selective semi permeable membranes 27a The anodes 26 and cathodes 28 slide into slots 56 in the ceramic walls (shown in FIG. 6B). The electrical connection to the electrodes passing through the lid 271 to anode bus 52 and cathode bus 54. The walls of the box have ridges 277 and grooves 279 made into them to promote turbulent flow thereby reducing adverse boundary layer related phenomena at the anodes 26.

A second embodiment of this electrochemical cell 25a bonds oxidation resistant ion selective membranes 27a (e.g., Nafion™) over the interior walls that are serving as the ceramic membranes 27a The addition of these membranes 27a supplements the performance of these ceramic membranes 27a.

Figure 6B:
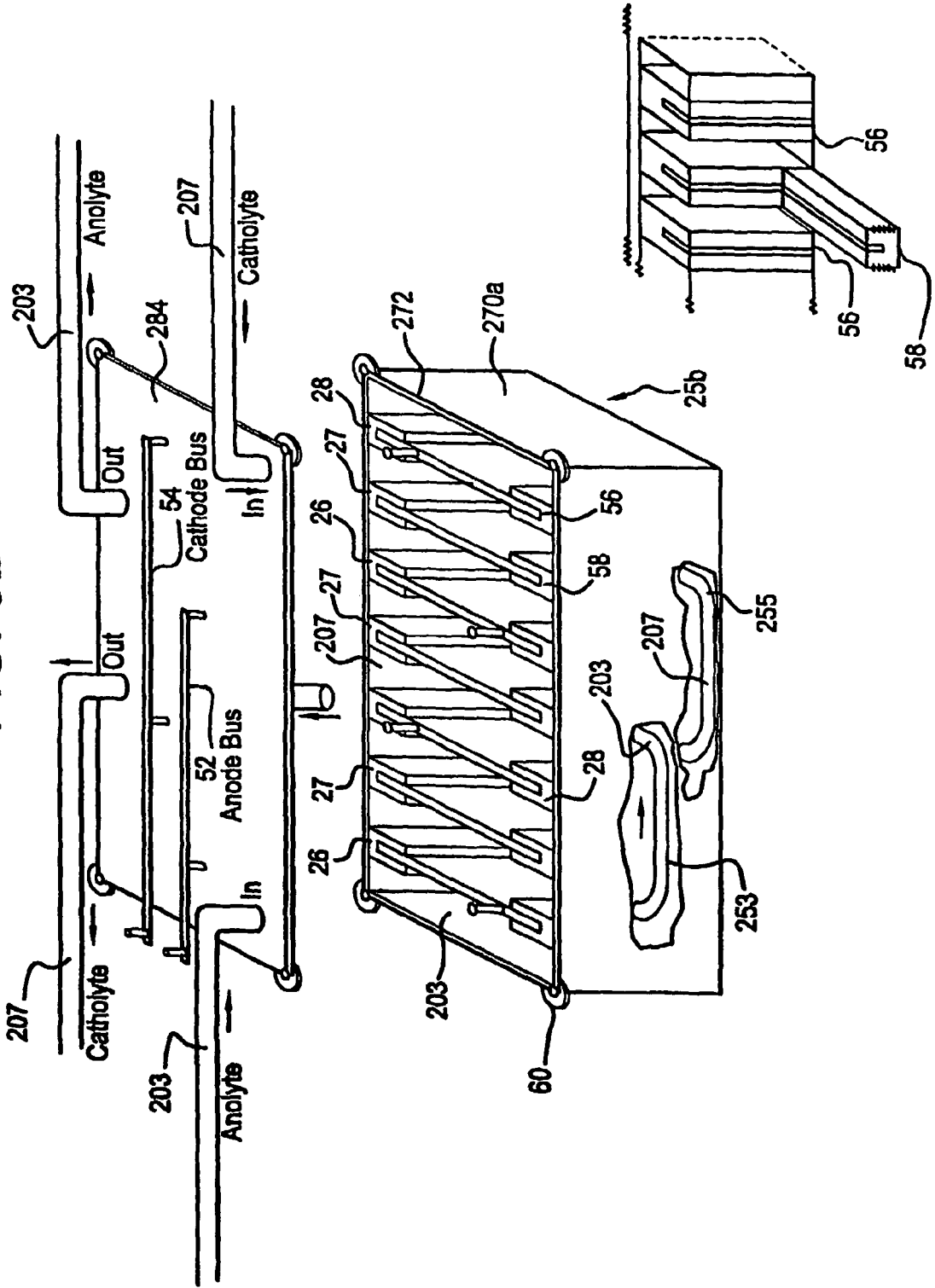
FIG. 6B Pier Design Electrochemical Cell is a representation of a box and lid design using materials such as metals, metal composites, fiberglass, and polypropylene.

A third embodiment uses a second electrochemical cell 25b, FIG. 6B, which has a pier box 270a and lid 284. The materials used for the FIG. 6B embodiment are selected from the following list of materials: fiberglass, polypropylene, metals and composite metals. The interior surfaces of this design will have PTFE coating to protect these surfaces from the oxidizer in the anolyte solution 203 and the acids or alkaline in the catholyte solution 207. The anodes 26 and cathodes 28 slide into electrode slots 56 in the electrochemical cell 25b walls with the electrical connection to them coming through the lid 284 to an anode bus 52 and cathode bus 54. The membrane 27 is held by membrane frame 58. The walls of the box have ridges 277 and grooves 279 (shown in FIG. 6A) made into them to promote turbulent flow thereby reducing adverse boundary layer related phenomena at the anodes 26. In another embodiment of this configuration the box 270a and lid 284 are composed of metal(s) and or metal composites and the surfaces in contact with the electrolytes are coated with a glass glaze or metallic oxides. The lid 284 is clamped using clamp holes 60 to the box 270a which includes a gasket 272 (shown in FIGS. 6A and 6B) thereby creating a liquid tight seal. The anolyte solution 203 and catholyte solution 207 flow through the box 270a in their respective channels. The anodes 26 and cathodes 28 are inserted in electrode slots 56 that are a part of the structure of the box 270a The anolyte solution 203 and catholyte solution 207 are separated by membranes 27 between them.

The membranes 27 are held in frames 58 that fit into slots 56 that are part of the structure of the box as shown in the FIG. 6B detail. The membranes 27 in their frames 58 are liquid tight to keep the anolyte solution 203 and catholyte solution 207 separated. The electrodes 26 and 28 are porous so that electrolyte flows through the electrodes 26 and 28 contacting both sides of the electrodes. The separated cells containing the anolyte solution 203 are connected by anolyte conduits 253 in the wall of the electrochemical cell 25b so that the anolyte solution 203 flows through the entire electrochemical cell 25b. The catholyte cells are connected in the same manner through catholyte conduits 255. This provides for easy of maintenance through ease of access to the interior of the box 270a and the membranes 27. Inserted through the lid 284 are platinum wires or miniature ORP electrodes in each chamber of the anolyte solution 203 and catholyte solution 207 positioned such that the electrical potential may be measured between the chambers. These electrical potentials provide information of the concentration of oxidizer in the anolyte chambers and also as an indicator of any leakage in the membrane 27.

Figure 6C:
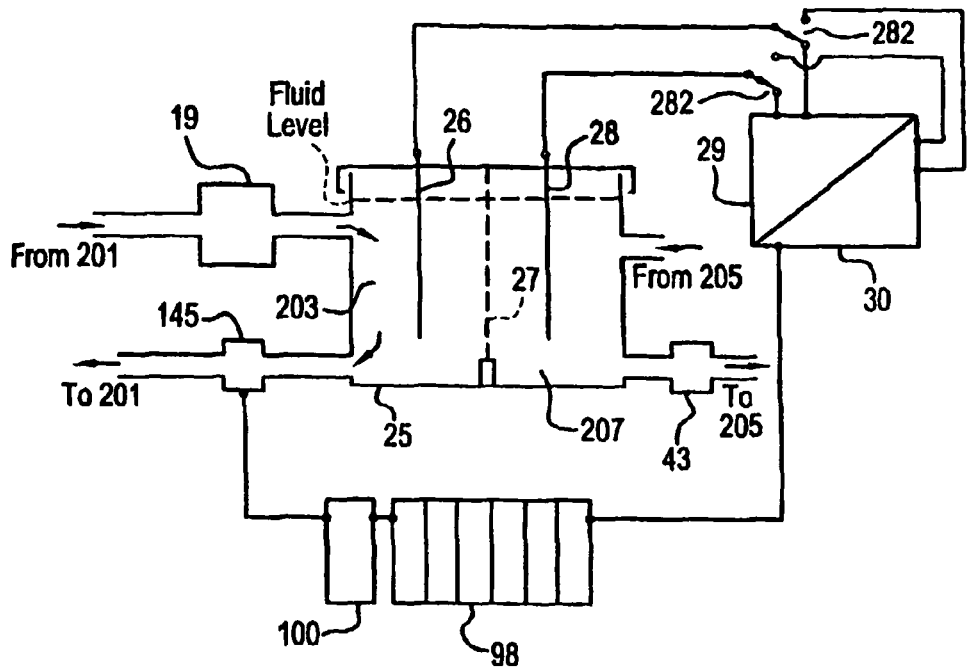
FIG. 6C Oxidizer Controlled Electrochemical Cell is a representation of an electrochemical cell that produces oxidizer under the control of an oxidation reduction potential (ORP).

A fourth embodiment of the electrochemical cell 25, FIG. 6C, which incorporates the use of an oxidation reduction potential (ORP) sensor 145 to control the level of oxidizer in the anolyte solution 203 during the operation of the MEO process. The anolyte solution 203 is pumped by anolyte pump 19 from the anolyte system 201 into the electrochemical cell 25. The ORP 145 detects the level of oxidizer being produced by the electrochemical cell 25 in the exit stream from the electrochemical cell 25. The ORP data is sent through the signal conditioner 100 to the PLC 98. The PLC 98 uses an algorithm to calculate desired oxidizer concentration in the anolyte solution 203. The PLC issues commands that regulate the DC power and AC (if used) current from the DC power supply 29. The DC power supply 29 provides the DC potential across the anodes 26 and cathodes 28 in the electrochemical cell 25. The AC power supply 30 provides the electrical power (i.e., 220v or 120v AC power) to the DC power supply 29. When the desired concentration level (as measured by the ORP 145) is reached the DC and AC (if used) current to the electrochemical cell 25 reduced or interrupted until the oxidizer level drops below the desired oxidizer level, at which point the DC and AC (if used) current from the DC power supply 29 is increased to the electrochemical cell 25. The PLC 98 algorithm controls the oxidizer level in the anolyte solution 203 by regulating the DC current to the electrochemical cell 25. The catholyte solution 207 is pumped from the catholyte system 205 by pump 43 into the electrochemical cell 25 and exits the electrochemical cell 25 back to the catholyte system 205. Membrane 27 separates the anolyte solution 203 and the catholyte solution 207 in the electrochemical cell 25.

Figure 7A:
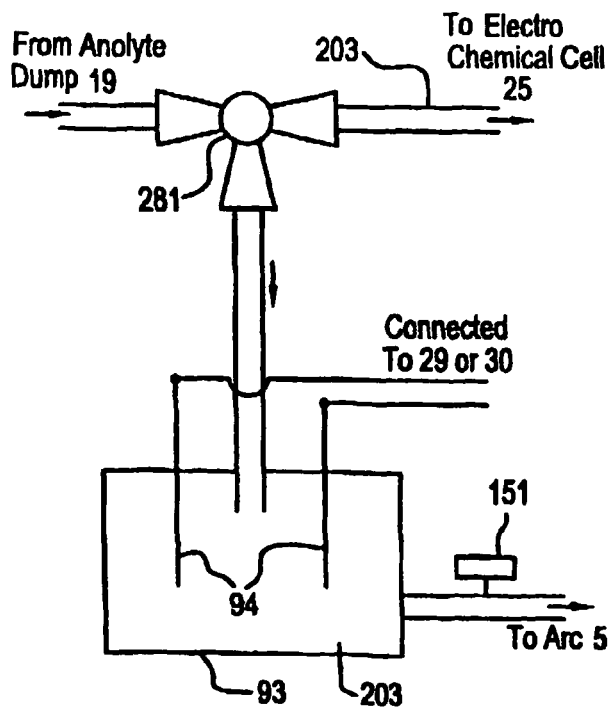
FIG. 7A Discharger is a representation of a discharger unit used to suppress the MEO oxidizers.

An advanced control system for regulating the oxidizer level uses the discharger 93 shown in FIGS. 1 and 7A to augment the algorithm as an additional control on the level of oxidizer in the anolyte solution 203. Electrodes 94 are connected to the DC output from power supply 29. In some cases the electrodes 94 my use low voltage high current AC. Discharger input valve 281 (see FIG. 7B) directs the anolyte solution 203 from pump 19 to the electrochemical cell 25 or to discharger 93. Sensor 151 senses the oxidation reduction potential (ORP) of the anolyte solution 203 flowing out of the discharger 93.

Oxidizer Suppression System

One embodiment of the MEO apparatus 200 has components that suppress electrochemically the oxidizers species population in the anolyte solution 203 when they are not needed or not wanted. FIG. 7A Discharger schematically depicts a discharger cell 93, consisting of two or more electrodes between which the anolyte flow is directed during the discharge process. The discharger 93 is introduced in the anolyte solution 203 flow stream by opening the discharger input valve 281. A low voltage DC and/or AC electro potential is applied between adjacent electrodes 94. The DC/AC switch 282 controls whether the voltage applied to the discharger 93 is DC or AC voltage. This voltage (typically below 3 volts) is selected so as to cathodically reduce the oxidizer species present in the anolyte solution 203 without causing their production via anodic oxidation. During the operation of the discharger 93 the DC voltage is not applied to the electrochemical cell 25. The DC power supply 29 may provide the voltage to the discharger 93 or two separate DC or AC power supplies by be used. The oxidizer species concentration may be measured both entering and leaving the discharger 93 by ORPs 150 and 151 as shown in FIGS. 1 and 7A, respectfully.

The anolyte solution 203 flows out of the discharger 93 and returns to the anolyte reaction chamber 5.

Figure 7B:
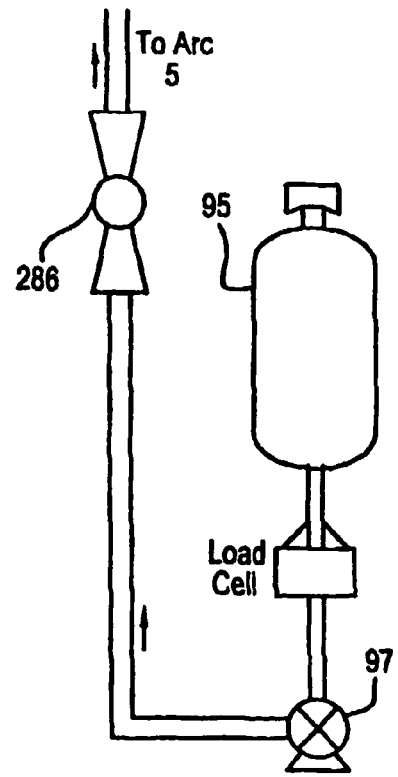
FIG. 7B Oxidizer Suppression Injection System is a representation of an injector unit used to suppress the MEO oxidizers.

In another embodiment, FIG. 7B, Oxidizer Suppression Injection System, the oxidizer species populations are suppressed by the introduction of a benign material to another (easily removable from the anolyte) benign material with the concomitants reduction of the oxidizer species to its reduced state. This material is stored in a suppressor tank 95. The suppressor material is injected into the anolyte solution 203 in the anolyte reaction chamber 5 through a suppression injector 97 up stream of the injection valve 286. The suppression injection operation is initiated by an operator and is controlled through the programmable logic controller (PLC) 98 (see the section on MEO Controller and FIGS. 9A and 9B). A variety of suppressors may be used, based on their ease of oxidation and removal from the combination of mediators and electrolytes used in the MEO apparatus 200 (e.g., formic acid).

In the case of an external power failure the suppressor material may be manually released.

Dewatering System

One of the end products of the MEO process in this patent is water formed by oxidation of hydrogen contained in the materials. In addition to the water by-product, the composition of the materials especially for biological and organic materials may contain large percentages of free water. The dewatering system may be required to operate on the anolyte solution 203 and/or the catholyte solution 207 to remove the excess water.

Both the anolyte solution 203 and catholyte solution 207 have significant amounts of water in their respective composition. The water content in the electrolytes (anolyte and catholyte) may change during the MEO process in the MEO apparatus 200 as a result of several phenomena. The free water being introduced with the materials being processed in the MEO apparatus 200 will accumulate in the anolyte. Water may cross the membrane 27 of the electrochemical cell 25 into the anolyte solution 203 or vice versa from the catholyte solution 207 due to osmotic pressure differences in the electrochemical cell 25. Furthermore oxidation of the hydrogen in the materials in the anolyte system 201 will add to the water in the anolyte solution 203. Water may also migrate from the anolyte solution 203 to the catholyte solution 207 via hydronium ion transport through the membrane 27. Dewatering is performed when a predetermined level has been reached in the anolyte reaction chamber 5. Referring to FIG. 1, the water removed from the anolyte solution 203 by a dewatering system is stored in a water storage tank 81. Water may cross the membrane 27 into the catholyte reservoir 31 from the anolyte system 201 via the aforementioned mechanisms. When the accumulation of water in the catholyte reservoir 31 reaches a predetermined level then the dewatering may be performed. The water removed from the catholyte solution 207 is stored in a water storage tank 81.

In the case when either the anolyte solution 203 or catholyte solution 207 has lost a significant amount of water, it will be restored by transfer from the water storage tank 81 into the anolyte reaction chamber 5 or the catholyte reservoir 31, respectively. Since water is a by-product of the MEO process, there may be a net accumulation when the MEO process has operated for a period of time. In this later case the water storage tank 81 may be drained into a waste line or used for other purposes since it is potable water.

The MEO process in this patent has a large number of simple/complex mediators using them singly, using them in combinations, using HPAs both singly and in combinations, and using mixtures of HPAs with simple/complex mediators. Furthermore, the MEO process may use acid, alkaline, and neutral electrolytes. Therefore the dewatering system may encounter a number of different mediator electrolyte combinations and materials.

The MEO apparatus 200 in this patent has a variety of dewatering systems available to select the one suitable for the mediator/electrolyte and materials to be processed. The following paragraphs characterize the different dewatering systems. This section explains how the water is transferred from the anolyte solution 203 and catholyte solution 207 into the water storage tank 81.

Reverse Osmosis

Embodiments of the MEO apparatus 200 that use reverse osmosis (RO) units are composed of several components. The different configurations of the RO units are shown in FIGS. 8A, 8B, 8C, 8D, and 8E. The wide variety of mediator/electrolyte combination in the MEO process in this patent may exceed the capability of the current art in (RO) units. The technical problems are the strong acidity and alkalinity, strong oxidizers, and cleaning residual materials from the RO membrane (especially if the materials are infectious). The following embodiments offer solutions to these technical problems.

Figure 8A:
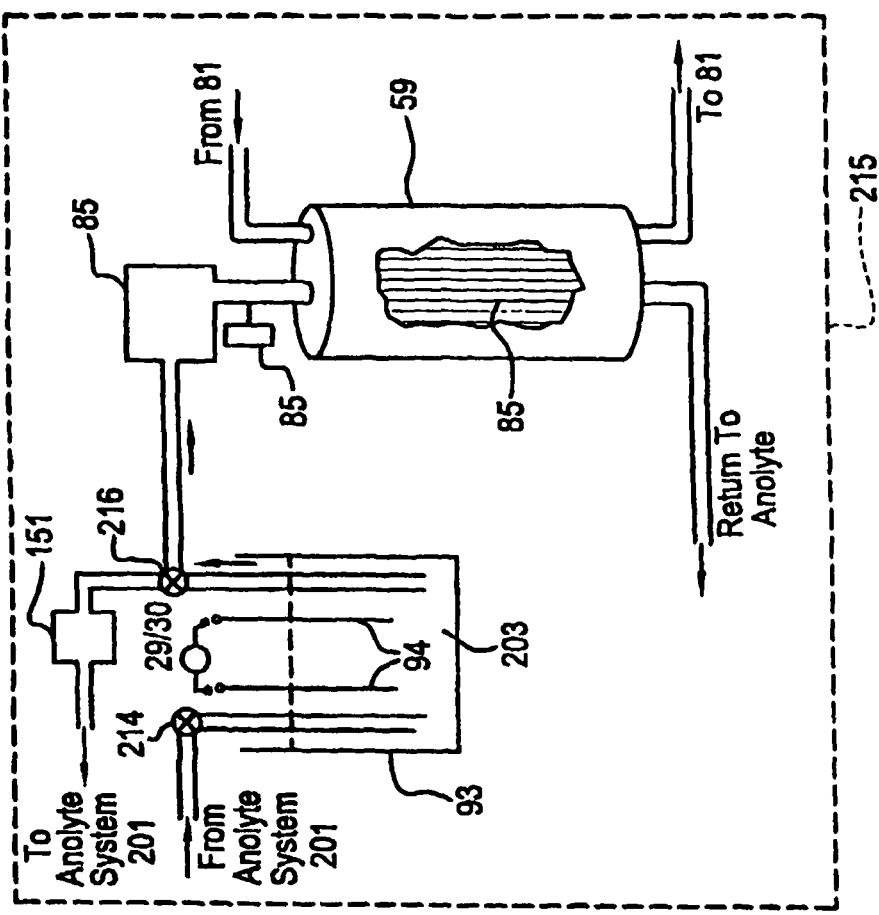
FIG. 8A Fluoropolymer/copolymer Based RO Unit 213 is a representation of Reverse Osmosis (RO) unit configuration for either or both the anolyte and the catholyte and using a fluoropolymer/copolymer (e.g., Nafion™) as the RO membrane.

In FIG. 8A Fluoropolymer/copolymer RO Unit 213 used in this MEO apparatus embodiment has a unique membrane 20 (for the anolyte), composed of a fluoropolymer/copolymer (e.g., DuPont's Nafion™). The name fluoropolymer/copolymer will be used to represent the class of membranes just discussed for ease of presentation. The fluoropolymer/copolymer membrane 20 tolerates all the mediator/electrolyte combinations in the MEO apparatus as has been the case in the electrochemical cell 25 discussed in the previous section. FIG. 8A represents the Fluoropolymer/copolymer RO Unit 213 configuration for the anolyte solution 203. The RO units used to dewater the anolyte solution 203 have pumps 83 to raise the pressure of the anolyte solution 203 as it enters the process side of the Fluoropolymer/copolymer RO membrane 20 in FIG. 8A. The reject water passes through the membrane 20 and is stored in the water storage tank 81.

The anolyte solution 203 is pumped into the RO membrane housing 59 by the RO pumps 83. The pressure of the anolyte solution 203 in the RO membrane housing 59 is sensed by pressure sensor (anolyte) 142.

The fluoropolymer/copolymer membrane 20 is used in the dewatering of the anolyte by an RO unit 213 when the oxidizer being used in the MEO apparatus would damage a membrane made from typical RO membrane materials. Cleaning of oxidizable material from the fluoropolymer/copolymer membrane 20 is accomplished by the action of the oxidizer in the anolyte solution 203 as it passes through the RO unit 213.

Figure 8B:
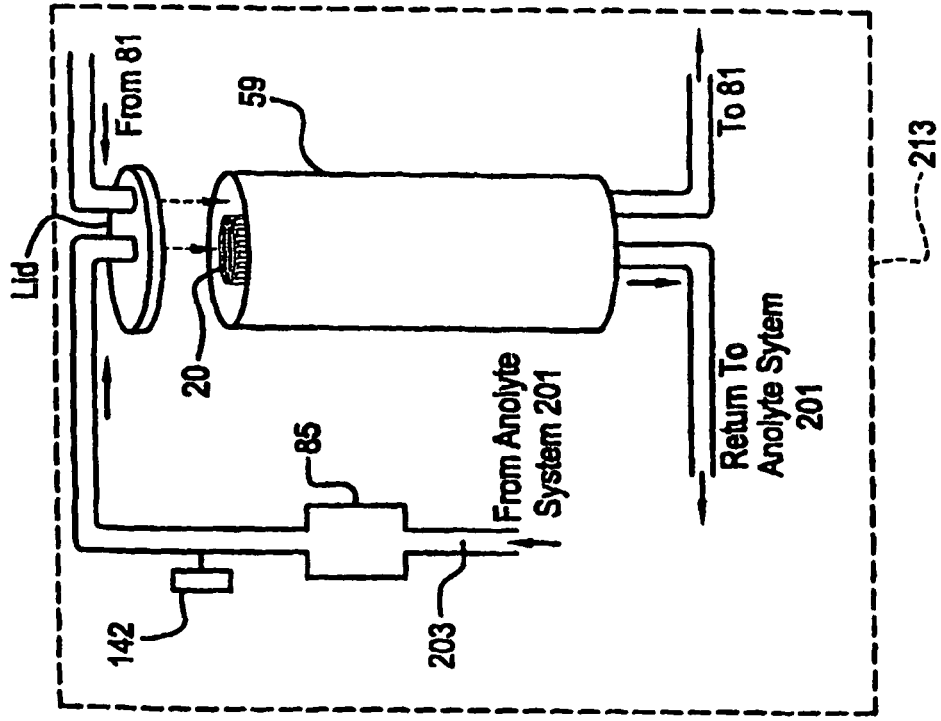
FIG. 8B RO Unit with Discharger 215 is a representation of a dewatering unit where the input to the RO unit is pretreated by passage (possibly repeated) through an oxidizer discharge unit.

FIG. 8B RO Unit with Discharger 215 is an embodiment of a dewatering unit where the anolyte and catholyte solutions acidity or alkalinity is not a problem for the RO unit. However, the oxidizer in the MEO process may damage the RO unit. A discharger 93, consisting of two or more electrode between which the anolyte solution 203 flow is directed during the discharge process as shown in FIGS. 7A and 8B, is introduced in the anolyte solution 203 flow stream. Discharger input valve 214 is opened to allow the anolyte solution 203 to enter the discharger 93. Discharger output valve 216 is opened to permit the flow of the anolyte solution 203 leaving the discharger 93 to flow through the sensor 151 back to the anolyte system 201. A low voltage AC or DC electro potential is applied between adjacent discharger electrodes 94. This voltage (typically below 3 volts) is selected so as to cathodically reduce the oxidizer species present in the anolyte solution 203 without causing their production via anodic oxidation. The low voltage discharges the oxidizers in the anolyte solution 203. The discharger 93 provides electrons to the oxidizers and they are returned to their reduced form. An oxidation reduction potential (ORP) sensor 151 senses the oxidized mediators in the anolyte solution 203. The anolyte solution 203 being discharged circulates through the discharger 93 until the mediator oxidation potential reaches a predetermined level. After the discharging process is complete the discharger output valve 216 opens to the RO pump 83 and the discharged anolyte solution 203 is processed through the RO membrane 85 which is enclosed in the RO membrane housing 59. The anolyte RO pressure is sensed by pressure sensor 142. The RO anolyte membrane 85 is a normal RO membrane not requiring the fluoropolymer/copolymer membrane 20.

Figure 8D:
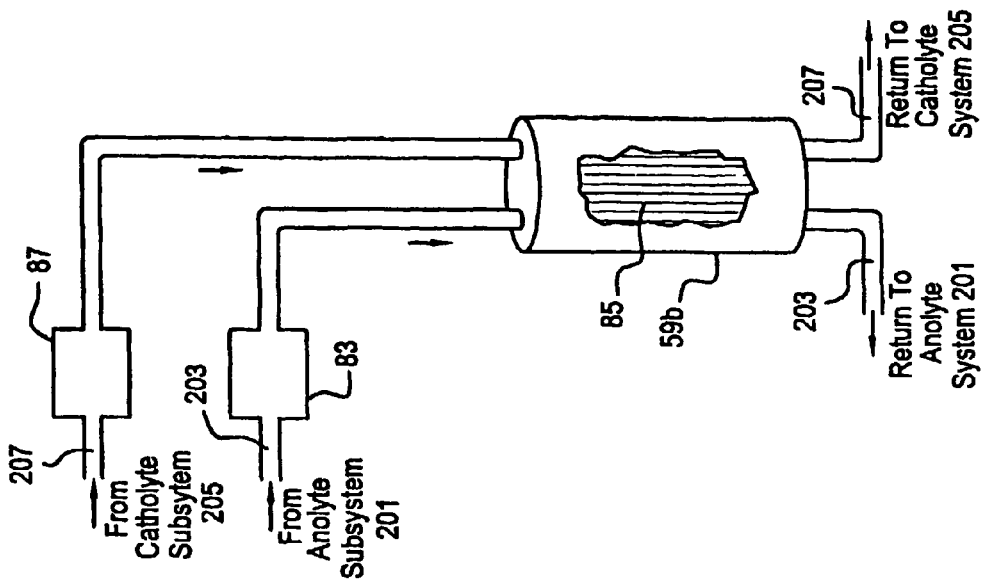
FIG. 8D RO Unit Reiecting to Catholyte 219 is a representation of a dewatering unit where the anolyte flows through the tube and catholyte flows through the shell of a RO unit.
Figure 8C:
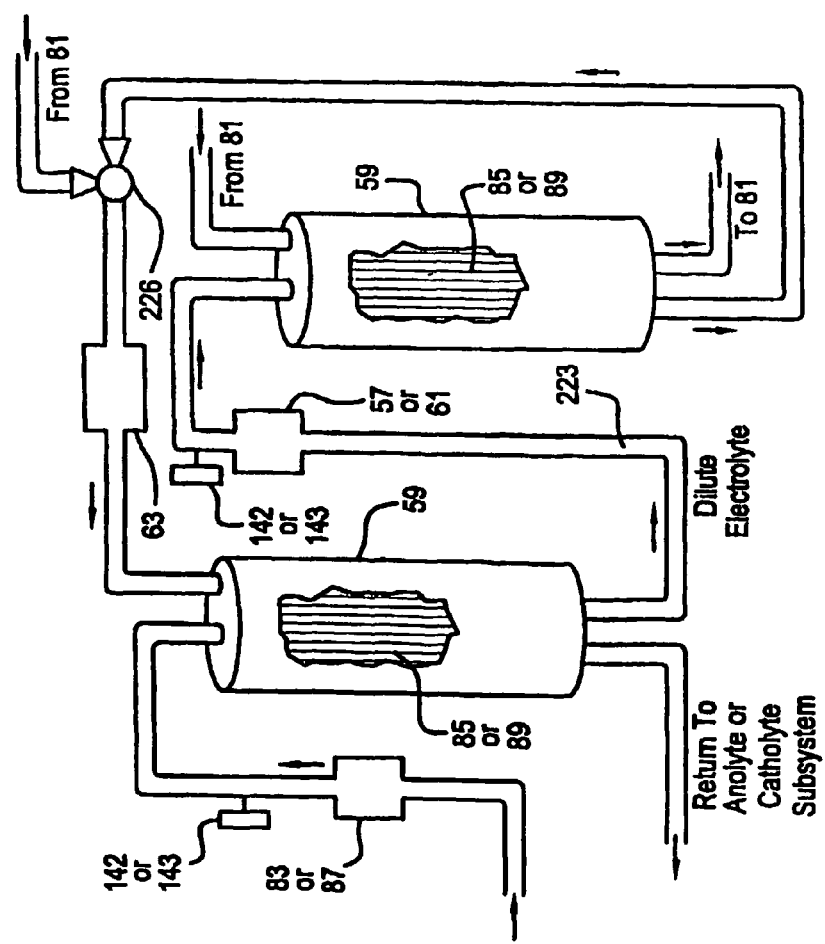
FIG. 8C Multi-Pass RO Unit 217 is a representation where a multi-stage RO unit is used to dewater either or both the anolyte and the catholyte.

FIG. 8C Multipass RO Unit 217 is an embodiment for a dewatering unit where the osmotic pressure head is so large that the pressure limit on the RO membranes 85 or 89 may be exceeded or the membrane partition factor may be insufficient to affect the required degree of separation in a single stage. The anolyte solution 203 or catholyte solution 207 is pumped by pumps 83 or 87 through the RO membrane 85 or 89. RO tubes made out of the RO membrane 85 or 89 fill the inside of the RO membrane housing 59. Rather than circulating water through the outside of the tubes (shell side), a dilute solution of the electrolyte 223 is used, thereby lowering the osmotic pressure between the two solutions. The RO pressure is sensed by either the anolyte sensor 142 or the catholyte sensor 143. The degree of dilution is chosen to be slightly less than that requiring the operational pressure limit. The dilute electrolyte solution is stored in the dilute electrolyte reservoir 63. This, now slightly more concentrated, shell side fluid is pumped by the second stage anolyte pump 57, or second stage catholyte pump 61, as the tube side liquid enters into RO membrane multipass housing 59a The osmotic pressure difference between it and the shell side pure water stream again allows operation below the pressure limit on the RO membrane 85 or 89. More RO stages may be applied if more difficult electrolytes are used. The pure water is stored in the water storage tank 81. Dilute electrolyte valve 226 is opened whenever additional water is needed in the dilute electrolyte 223.

FIG. 8D RO Unit Rejecting to Catholyte 219 is an embodiment where the anolyte solution 203 electrolyte and catholyte solution 207 electrolyte are similar in composition and the RO membranes 85 can tolerate the electrolytes. The excess water in the anolyte solution 203 is rejected into the catholyte solution 207 through the RO membrane 85. The RO approach would be to again use the anolyte solution 203 pumped by pump 83 as the tube side fluid in the RO membrane housing 59b. The catholyte solution 207 is pumped by pump 87 through the shell side. After the anolyte solution 203 and the catholyte solution 207 leave the housing 59b they return to the anolyte system 201 and the catholyte system 205, respectively. Since the compositions of the electrolytes are similar, this would again greatly reduce the osmotic pressure difference between the two solutions (i.e., due mainly to the dissolved mediator), allowing use of a normal RO unit. This would allow all further dewatering to be conducted only on the catholyte solution 207, which contains no dissolved mediator salts or materials, and may have to be dewatered anyway. The catholyte solution may be dewatered in a standard RO unit (FIG. 8D does not show the standard RO unit). The pure water is stored in the water storage tank 81.

Figure 8F:
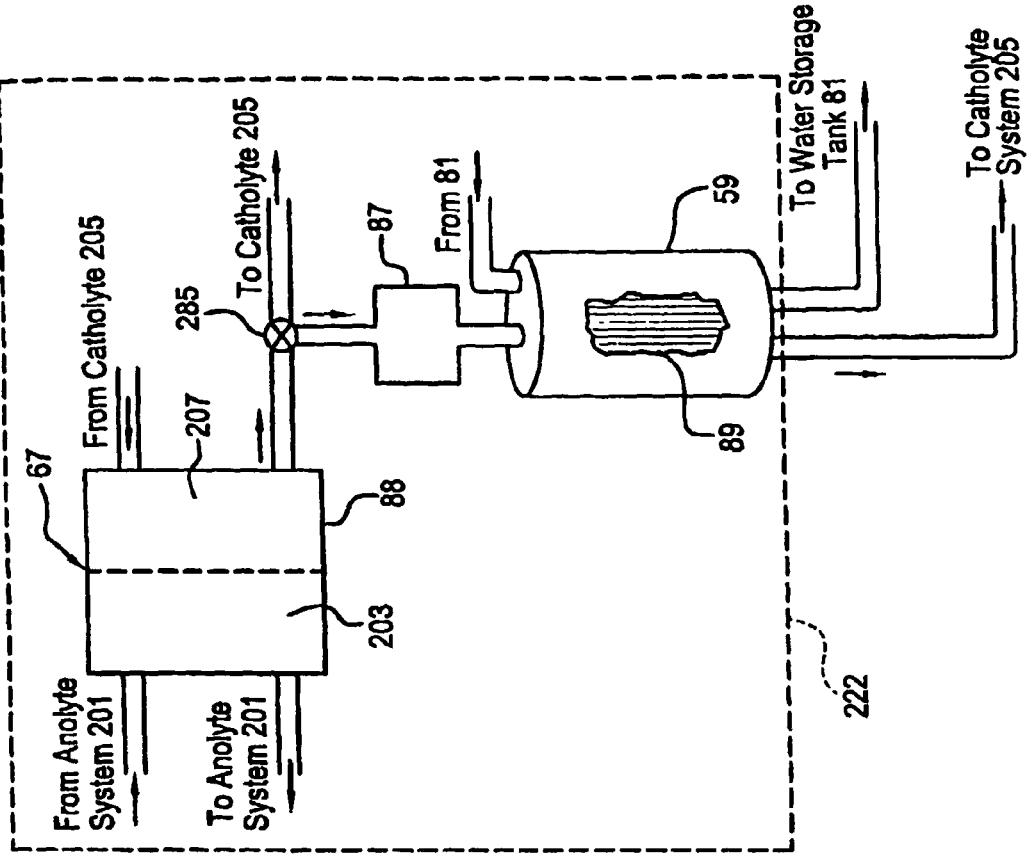
FIG. 8F Osmotic Cell 222 is a representation of a dewatering system where the osmotic pressure drives water from the anolyte to the catholyte across a semi-permeable membrane.
Figure 8E:
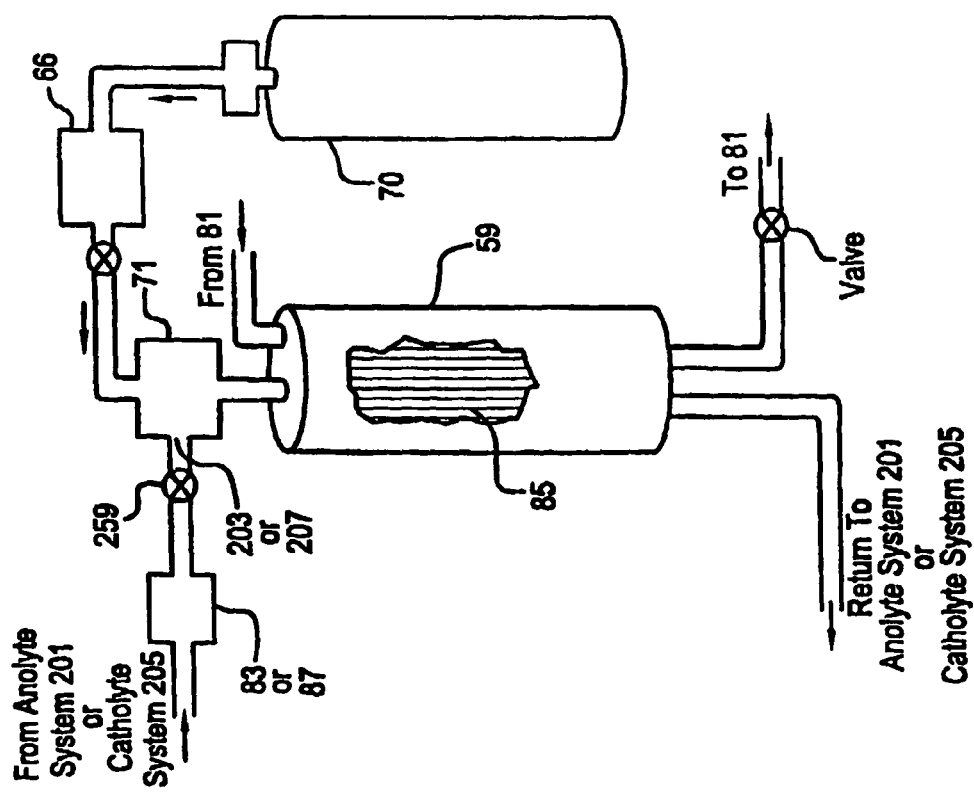
FIG. 8E Static RO Unit 220 is a representation of a dewatering unit where the anolyte or catholyte remains in the RO membrane under static pressure.

FIG. 8E, Static RO Unit 220, is an embodiment, where the volume of anolyte solution 203 is relatively small. When dealing with a small volume, the flow rate through the RO membrane 85 is low per unit area, thus requiring lots of area. A flow rate of 1-2 liters in 15-30 minutes requires a certain RO tube surface area. However, the total volume of the tubes required for this surface area exceeds the total anolyte volume. In this embodiment a non-flow configuration may be used. Valve 259 is opened to allow all the anolyte solution 203 to be transferred from anolyte system 201 through pump 83 into the RO system, tubes 85 in the RO membrane housing 59. The RO reservoir 71 and is pressurized to several thousand psi with air or nitrogen from the pressurized vessel 70 and let stand until the dewatering has reached the desired goal. The regulator 66 controls the pressure in the RO system, by releasing the air or nitrogen gas from the pressurized vessel 70 until the desired pressure has been reached in the RO system, and holds that pressure until the dewatering is complete. The pressurization may be accomplished by using a high pressure pump 83 in lieu of the pressurized gas. The regulator 71 holds the anolyte solution 203 under pressure in the RO membrane 85 in the housing 59. The catholyte solution 207 may be processed in a manner similar to the anolyte solution 203 by using the nitrogen pressure vessel 70 and by using the catholyte RO pump 87. The pure water is stored in the water storage tank 81. The anolyte solution 203 or the catholyte solution 207 is returned to the anolyte system 201 or the catholyte system 205, respectively.

Osmosis

FIG. 8F Osmotic Cell 222 is an embodiment where the anolyte solution 203 and catholyte solution 207 compositions are such that the osmotic pressure would drive water from the anolyte side to the catholyte side of the semi permeable membrane, osmotic membrane 67. A simple normal osmosis cell 88, possibly pressurized on the anolyte side to increase flow, would then be adequate to dewater the anolyte by driving the water from the anolyte solution 203 to the catholyte solution 207. The anolyte solution 203 enters the osmotic cell 88 from the anolyte system 201 and returns to the anolyte system 201. The catholyte solution 207 enters the osmotic cell 88 from the catholyte system 205 and returns to the catholyte system 205. The diluted catholyte solution 207 may be dewatered using an appropriate one of RO methodologies previously described for dewatering the anolyte solution 203. The valve 285 is switched to allow the catholyte RO pump 87 to feed the catholyte solution 207 into the catholyte RO membrane 89 located in the RO membrane housing 59. When the catholyte is not being dewatered valve 285 is switched to allow the catholyte solution to flow back to the catholyte system 205. Again the advantage herein is working with a mediator free liquid. The pure water is stored in the water storage tank 81 shown in FIG. 1.

Figure 8H:
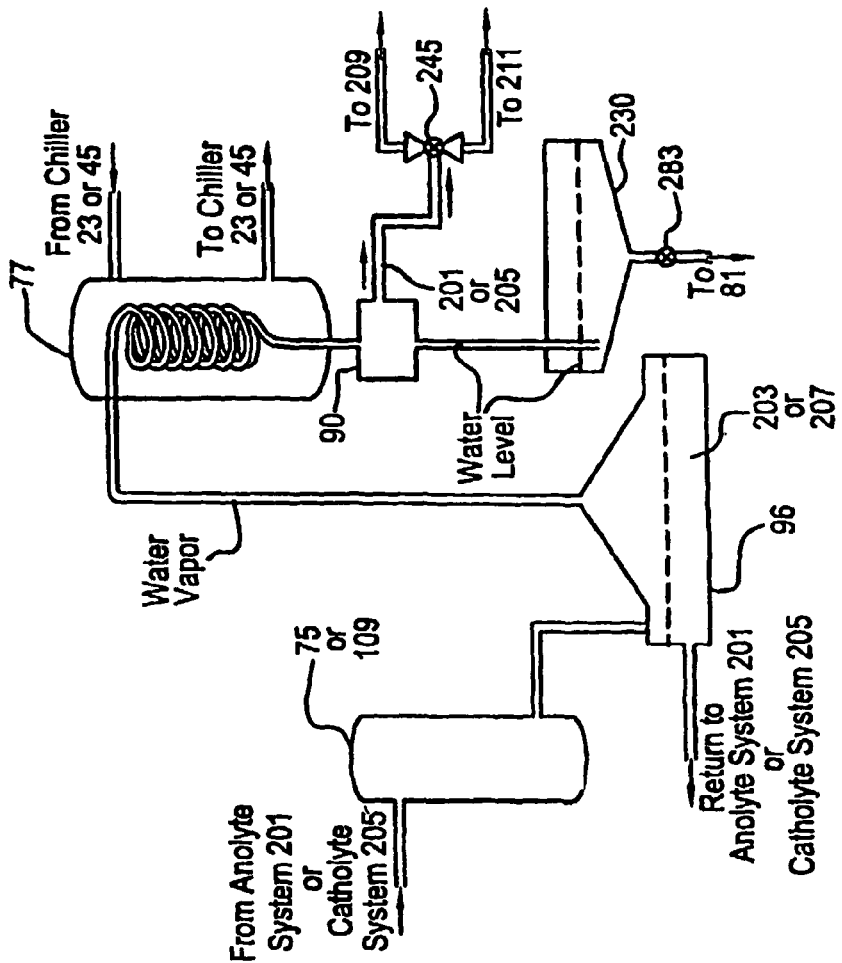
FIG. 8H Vacuum Evaporation 227 is a representation of a dewatering process that applies the vacuum evaporation technique to either or both the anolyte and the catholyte.
Figure 8G:
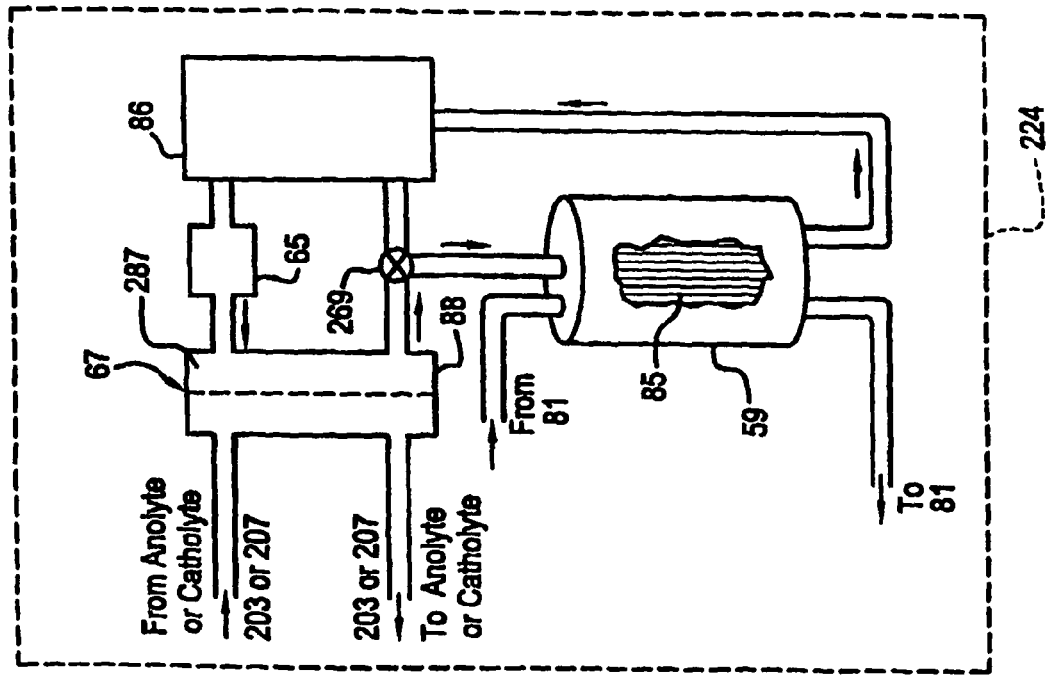
FIG. 8G Osmotic Cell with Selected Osmotic Fluid 224 is a representation of an osmotic cell where either or both the anolyte and the catholyte fluids lose water to a selected fluid designed to dewater these fluids.

FIG. 8G, Osmotic cell with Selected Osmotic Fluid 224, shows an embodiment where the catholyte solution 207 has too low an osmotic pressure difference and the water in the anolyte will not cross the osmotic membrane 67, in which case a second osmotic fluid with a higher osmotic pressure may be selected that will permit the water to pass through the membrane. A normal osmotic cell 88 is composed of two separate chambers where anolyte solution 203 or catholyte solution 207 flow along an osmotic membrane 67. The other side of the osmotic membrane 67 is in contact with an osmotic fluid 287 selected such that its osmotic pressure allows the water in the anolyte solution 203 or catholyte solution 207 to cross the osmotic membrane 67. The osmotic fluid 287 selected is stored in the osmotic reservoir 86. The osmotic fluid 287 is pumped by the osmotic pump 65 from the osmotic reservoir 86 through the osmotic cell 88 and back to the osmotic reservoir 86. When the anolyte solution 203 or the catholyte solutions 207 are to be dewatered the osmotic valve 269 is positioned to allow the solutions to flow into the RO membrane housing 59 which contains the RO membranes 85. The processed water passes through membrane 85 and is stored in the water storage tank 81, where it is available to be returned to either the anolyte or the catholyte or to be rejected from the MEO apparatus. The osmotic fluid 287 is returned from the RO membrane housing 59 to the osmotic reservoir 86.

Vacuum Evaporation

In FIG. 8H, Vacuum Evaporation Unit 227 is an embodiment that provides for water being removed from the anolyte solution 203 and/or catholyte solution 207 by vacuum evaporation. Anolyte solution 203 or catholyte solution 207 may exit the anolyte system 201 or the catholyte system 205 and pass through either a nanofilter 75 or an ultrafilter 109. These filters remove small particulate form the anolyte solution 203 or the catholyte solution 207. Nanofiltration 75 is used as a pretreatment for removal of all solids (i.e., dissolved and suspended particulates) and soluble organics from the anolyte feed stream to the evaporator 96. Therefore, this filtration provides for the elimination of the evaporator 96 as a potential source of air borne infectious release.

The filtered anolyte solution 203 or catholyte solution 207 flows into the evaporator 96. The anolyte solution 203 or the catholyte solution 207 flows from the evaporator 96 to the anolyte system 201 or the catholyte system 205. The anolyte solution 203 or the catholyte solution 207 continue to circulate through the vacuum evaporator unit 227 until the excess water in the solutions are reduced to the desired level.

The vacuum evaporation process begins by reducing the pressure in the evaporator 96 condenser 77 system to less than the vapor pressure of water in the anolyte solution 203 or catholyte solution 207 at their respective temperatures. The vacuum pump 90 reduces the pressure in the evaporator 96 condenser 77 system. Water evaporates from the anolyte solution 203 or the catholyte solution 207 and progresses into the condenser 77. The pressure in the evaporator 96 condenser 77 system is controlled by the vapor pressure of water at the condenser 77 temperature. A chilled solution from the anolyte chiller 23 or the catholyte chiller 45 flows through the condenser 77 jacket and returns to the anolyte chiller 23 or the catholyte chiller 45, respectively. The heat removal in the condenser 77 coils results in the water vapor condensing in the coils. Water flows from the condenser 77 through the condenser cold leg where it will be exhausted by the vacuum pump 90. Water is allowed to exit the water reservoir 230 through the water reservoir valve 283 when the water in the reservoir has reached a predetermined water level.

Any gas present in the anolyte solution 203 or the catholyte solution 207 may exit with the water vapor into the condenser 77 into the water reservoir 230. The gas may exit out the top of the water reservoir 230. The off-gas handling selection valve 245 allows the gas to exit either to the anolyte off-gas handling system 209 or to the catholyte off-gas handling system 211.

In some cases there may be some noncondensible gases present due to the initial evaporator 96 atmosphere, in-leakage, dissolved gases, etc. The intermittent use of this system will result in the evaporator 96 startup atmospheres being the chief source of noncondensibles. Evacuating the previously cleaned (or disinfected if required) evaporator 96 prior to introduction of the anolyte solution 203 may remove this source of noncondensibles. With proper design of the system (i.e., evaporator 96 volume, condenser heat transfer area, anolyte chiller 23 or catholyte chiller 45, temperature, etc.) the desired degree of dewatering may be accomplished before removal of noncondensibles becomes necessary. The gas volumes may be very small compared to the volume of anolyte reaction chamber 5 purge air. Dissolved gases may include $CO_2$ and volatile organics not completely oxidized to $CO_2$, may be present in the anolyte reaction chamber 5 purge gas too.

In another embodiment, if gases are present in the discharge from the vacuum pump 90 they may be diverted into the anolyte off-gas handling system 209 or the catholyte off-gas handling system 211 and filtered in these systems by incorporating an ion exchange or molecular sieve silica column in these systems thereby removing this potential source of air born release. Another embodiment may incorporate the use of a nanofilter 75 such as a nanofiltration (i.e., 0.001 to 0.05 μm) and/or ultrafiltration (i.e., 0.03 to 0.05 μm) to ensure that atmospheric releases are free from any infectious materials becoming entrained in the gas stream from the anolyte reaction chamber 5. The nanofilters 75 and the ultrafilters 109 are clean by flushing the filters with fresh anolyte solution 203 during the cleaning cycles.

In another embodiment, the liquid formed by condensation of evaporate from the evaporator 96 operation may be purified by a conventional RO unit prior to release. The concentration of electrolyte in this condensed liquid is sufficiently dilute to be comparable to that presently treated in materials stream acid recovery operations (ref Osmonics, Inc. nanofiltration publications #126—Acid Materials, #106 Oil/Water Separation and Acid Recovery Systems at "www.osmonics.com).

Controller System

Figure 9A:
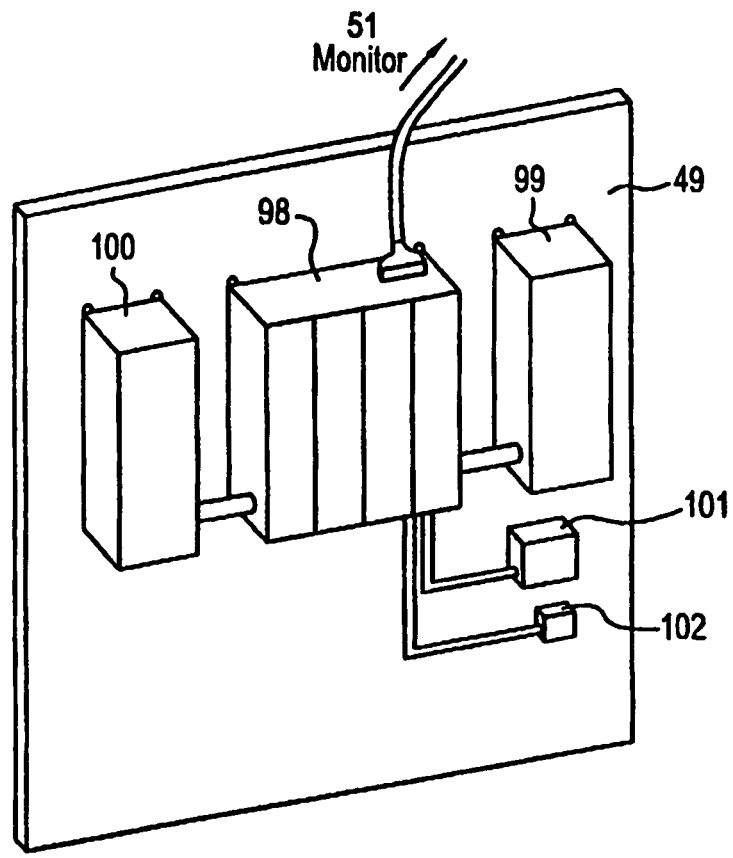
FIG. 9A Controller System 49 is a representation of the MEO apparatus system that controls the operation of the MEO process.
Figure 9B:
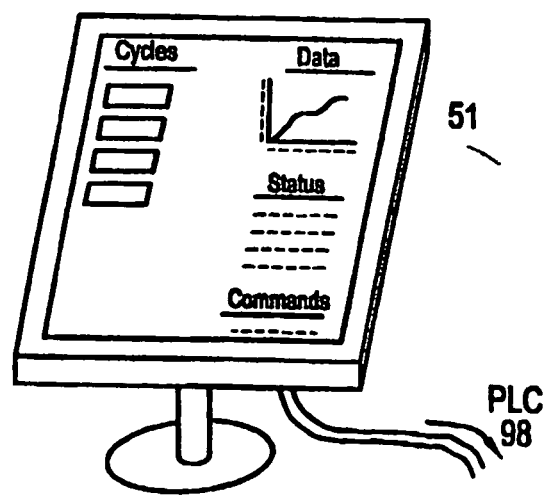
FIG. 9B Monitor is a representation of the MEO apparatus display monitor that is interface between the operator and the equipment providing the selection of options and status of the MEO apparatus.

FIG. 9A Controller System 49 is a representation of a typical controller system used for MEO apparatus 200. Some embodiments of the MEO apparatus 200 are designed with automated programmable logic controllers (PLCs) 98. The controller system 49 couples PLCs 98 with pneumatic controls and system sensors. The controller system 49 monitors the process being performed by the MEO apparatus 200 and displays these data and status information on a monitor 51 (as shown in FIG. 9B). The controller system 49 executes the operational cycles in the MEO process. The PLCs 98 provide the methodology to change the parameters in the MEO process through digital control over the system components such as a) flow control of anolyte and catholyte; b) electrochemical cell power; c) off-gas systems; d) ultraviolet and ultrasound systems. The PLC 98 contains the default values for typical parameters such as a) percent pump flow rate, b) anolyte and catholyte volume capacity, c) anolyte and catholyte temperatures, d) valve operation and sequencing, e) enabling and disabling of RO dewatering, f) water makeup in the anolyte and catholyte systems, g) ultrasonic and ultraviolet source operations, h) off-gas temperatures, and i) enabling and disabling the data logging. The MEO process has numerous mediator and electrolyte combinations and the controller system 49 provides the methodology to change the MEO apparatus 200 system parameters easily. The controller system 49 will maintain a record of the operation of the MEO apparatus 200 for a post operation analysis using the data recorded in the data logger 99.

The controller system 49 may contain a touch screen monitor 51 (as shown in FIG. 9B). The monitor 51 provides the operator of the MEO apparatus 200 with the options for running the equipment. Samples of those options available in the MEO apparatus 200 axe discussed in the section MEO System Operational Cycles discussed later in this patent. The monitor 51 may display the status of each component in the MEO apparatus 200 based on the information from the sensors and instrumentation (covered in detail in a following section) processed through the signal conditioner 100. The activity of the redox couples are measured using an oxidation reduction potential (ORP) sensor located throughout the MEO apparatus 200 (see Table 4). Using the ORPs and the sensors measuring the $CO_2$, an algorithm can be developed to calculate the state of the oxidation process in the MEO apparatus 200. The state of the oxidation process may be directly evaluated by displaying the data from the sensors on the monitor 51 where it is evaluated by the operator. FIG. 9B Monitor is a depiction of the monitor 51 displaying a screen.

The controller system 49 is internet enabled through connections such as Ethernet 101. One embodiment of the controller system 49 connects the MEO Apparatus 200 to a phone line 102, or a cell phone, or to a personal computer (PC) using the internet enabled connection such as 101. The controller system 49 is access through the internet, or PC and the status of the system are monitored on-line. The controller system 49 may be updated and faults corrected through the internet connectivity.

One embodiment of the controller system 49 has a data logging system 99 that records the sensor data used to assess performance and past use of the system. The data may be view remotely or on-site. The controller system 49 provides the information that may be used to diagnose any problem that may be occurring with the MEO apparatus 200.

Some embodiments of the MEO apparatus 200 have limited applications and do not need the flexibility discussed in the previous embodiments. In those cases the PLC 98 may be replaced with small microprocessors or multi-position cyclic timer switches (similar to those used in dishwashers and washing machines).

Off-Gas System

FIG. 10 Off-gas Processing System The anolyte reaction chambers 5(a,b,c,d,e) off-gas consists of $CO_2$ and CO from complete and incomplete combustion (i.e., oxidation) of the carbonaceous material in the biological and organic materials, and may include oxygen from oxidation of water molecules at the anode and possibly small amounts of low molecular weight hydrocarbons from incomplete combustion that are gases at the anolyte solution 203 operating temperature and pressure. The off-gas processing system may be monitored in real time with the $CO_2$ detector sensor 139. The off-gas is extracted by the air flow through the anolyte reaction chamber 5 and catholyte reservoir 31 by an exhaust fan 50. The exhaust fan 50 draws the room air into anolyte reaction chamber 5 through the anolyte air intake filter 84 and into catholyte reservoir 31 through the catholyte air intake filter 44. The flow of the off-gas is sensed by a sail switch 138. The off-gas handling system is composed of the anolyte off-gas handling system 209 and the catholyte off-gas handling system 211.

Anolyte Off-Gas Handling System

Reaction products resulting from the oxidation process occurring in the anolyte system 201 that are gaseous at the anolyte operating temperature and pressure are discharged through the anolyte off-gas exit tube 247 to the anolyte demister 55. The anolyte off-gas handling system 211 is depicted in FIG. 10. The anolyte demister 55 is cooled by the coolant from the anolyte chiller 23. The more easily condensed products of incomplete oxidation are separated in the anolyte demister 55 from the anolyte off-gas stream and are returned to the anolyte reaction chamber 5 or the anolyte reservoir 2 through the anolyte condensate return tube 249 for further oxidation. The anolyte reaction chamber 5 and the anolyte reservoir 2 are connected through the dump valve 92 which allows the anolyte solution 203 contents of the anolyte reaction chamber 5 to be stored in the anolyte reservoir 2. The non-condensable incomplete oxidation products (e.g., low molecular weight organics, carbon monoxide, etc.) are reduced to acceptable levels for atmospheric release by a gas cleaning system 16. The gas cleaning system 16 is not a necessary component of the MEO apparatus for the destruction of most types of materials.

If the gas cleaning system 16 is incorporated into the MEO apparatus 200, the anolyte off-gas is contacted in a counter current flow gas scrubbing system in the gas cleaning system 16; wherein, the noncondensibles from the anolyte demister 55 are introduced into the lower portion of the column through a flow distribution system of the gas cleaning system 16; and, a small side stream of freshly oxidized anolyte direct from the electrochemical cell 25, is introduced into the upper portion of the column. This results in the gas phase continuously reacting with the oxidizing mediator species as it rises up the column past the down flowing anolyte. This system is similar to the one shown in FIG. 4F. Under these conditions, the gas about to exit the top of the column may have the lowest concentration of oxidizable species; and, also may be in contact with the anolyte having the highest concentration of oxidizer species, thereby, promoting reduction of any air pollutants present down to levels acceptable for release to the atmosphere. Gas-liquid contact within the column may be promoted by a number of well established methods (e.g., packed column, pulsed flow, ultrasonic mixing, etc,) that do not result in any meaningful backpressure within the anolyte flow system. Anolyte exiting the bottom of the countercurrent scrubbing column is discharged into the anolyte system upstream of pump 19 and mixed with the remainder of the anolyte returning to the electrochemical cell 25. Unique materials compositions may result in the generation of unusual gaseous products that may be removed by more traditional air pollution technologies. Such methodologies may be used in series as a polishing process treating the gaseous discharge from the countercurrent column, or if advantageous, instead of it. The major products of the oxidation process are $CO_2$, and water (including minor amounts of CO and inorganic salts), where the $CO_2$ is vented through the off-gas vent 14 out of the system or absorbed by an ion exchange resin column. The carbon dioxide off-gas is measured by the $CO_2$ sensor 139.

Catholyte Off-Gas Handling System

The catholyte off-gas handling system 211 is depicted in FIG. 10. Room air is drawn through the catholyte reservoir 31 and passes through the catholyte off-gas exit tube 248 to the catholyte demister 82 by the exhaust fan 50. The water vapor in the air stream is condensed in the catholyte demister 82 by the coolant from the catholyte chiller 45. The condensate returns to the catholyte reservoir 31 through the catholyte condensate return tube 250.

Hydrogen gas is evolved at the cathode when certain catholyte solution 207 electrolyte is used. This case is discussed in more detail in a later section on the hydrogen gas system.

Sensors and Instrumentation

Some embodiments of the MEO apparatus 200 are designed to operate under the control of a program logic controller (PLC) 98. The PLCs 98 are programmed with several automated system operational cycles which will be discussed in the following section. The MEO apparatus 200 have numerous sensors and instruments that provide the PLC 98 with the status of the apparatus. The point has been made in previous sections that the MEO process is very flexible. The numbers of combinations of mediators provide the MEO apparatus 200 with the capability of handling numerous types of materials with out changing the hardware. The PLC 98 approach continues this flexibility by providing for easy modifications of the operation of the MEO apparatus 200 to accommodate changes in use of the system with significant hardware changes.

The sensors provide information on: the electrical components, fluid flow, valve positions and plumbing, off-gas handling and cleaning systems, electrochemistry, state of the MEO process, temperature, dewatering, performance, maintenance, and safety. Table 4 MEO Apparatus Sensors and Instrumentation lists the sensors for the system illustrated in this patent. The embodiment of the MEO apparatus shown in FIG. 1 has thirty-five (35) sensors incorporated into the design. Temperature is measured throughout the anolyte system 201 by sensors 120 through 124 and throughout the catholyte system 205 by sensors 125 through 128. The flow rates of the catholyte solution 207 and the anolyte solution 203 in their respective systems are measured by flow meters 129 through 131. The level of anolyte solution 203 and catholyte solution 207 in the anolyte reaction chamber 5, anolyte reservoir 2 and the catholyte reservoir 31 are measured by sensors 132 through 137.

The following abbreviations are used in Table 4; a) anolyte reaction chamber—ARC, b) anolyte reservoir—AR, and c) catholyte reservoir—CR, d) reverse osmosis—RO, electrochemical cell—EC, and f) oxidation reduction potential—ORP.

Some embodiments of the MEO apparatus 200 do not require the degree of flexibility that a PLC provides. In those embodiments apparatus use circuit boards, relays, multi-position timing switches, etc., which considerably simply the control system.

Nitrogen Gas System

Figure 11A:
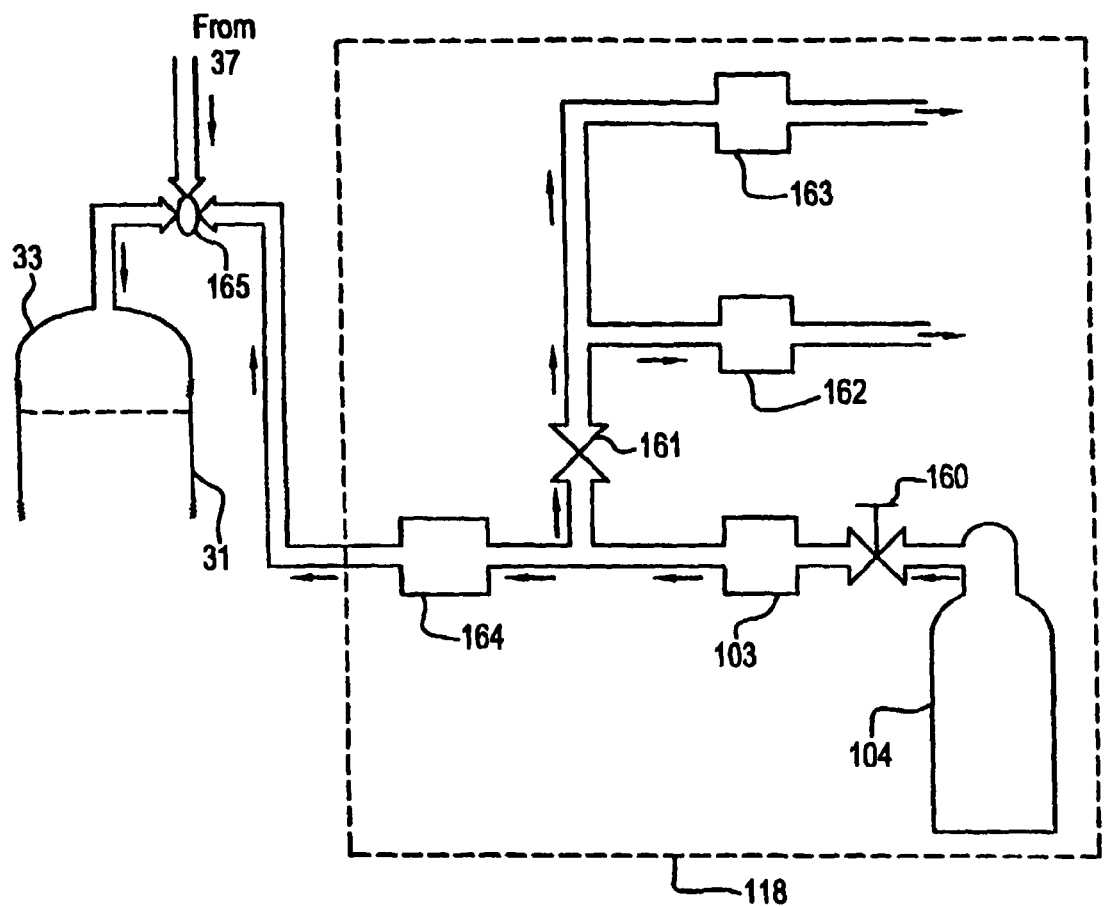
FIG. 11A Nitrogen Gas System 118 is a representation of the nitrogen gas system used to purge the catholyte reservoir in case the hydrogen gas exceeds a safe level and to provide gas pressure to power valves in the anolyte system and catholyte system.

The MEO apparatus 200 may contain a nitrogen gas system 118 that is used to perform two functions. The nitrogen gas system 118 is shown in FIG. 11A. The nitrogen gas bottle 104 has a manual gas valve 160 that opens and closes the nitrogen gas bottle 104. The manual gas value 160 is closed when the nitrogen gas bottle is being removed from the MEO apparatus 200. When the manual gas valve 160 is opened the nitrogen pressure regulator 103 controls the nitrogen gas pressure to the nitrogen gas system 118. The nitrogen gas pressure regulator 103 is controlled by commands from the PLC 98.

First the nitrogen gas system 118 is used to purge the catholyte reservoir 31 in case the hydrogen gas exceeds a two percent level in the off-gas handling system 211 (see FIG. 10). The catholyte reservoir purge regulator 164 is opened by a command from the PLC 98 allowing nitrogen gas to flow. The catholyte reservoir purge valve 165 is opened by a PLC 98 command allowing nitrogen gas to purge the catholyte reservoir 31. Catholyte reservoir purge valve 165 closes the catholyte air sparge 37 so that the nitrogen purges the catholyte reservoir 31.

The second function of the nitrogen gas system 118 is to provide gas pressure to power the valves in the anolyte system 201 and catholyte system 205. The nitrogen instruments enable valve 161 opens by command from the PLC 98 to provide nitrogen gas pressure to instruments and actuators in the MEO apparatus 200. The nitrogen gas pressure is regulated to the instruments by the instrument nitrogen pressure regulator 162 and to the actuators by the actuator nitrogen pressure regulator 163.

Hydrogen Gas System

The MEO process may produce hydrogen gas in the catholyte reservoir 31 when certain catholytes are used. Typical of these catholytes are the sulfuric acid and sulfate salts. The MEO apparatus may be configured to either collect the hydrogen for use as a fuel or dilute the hydrogen to safe levels for discharge into the atmosphere.

Figure 11B:
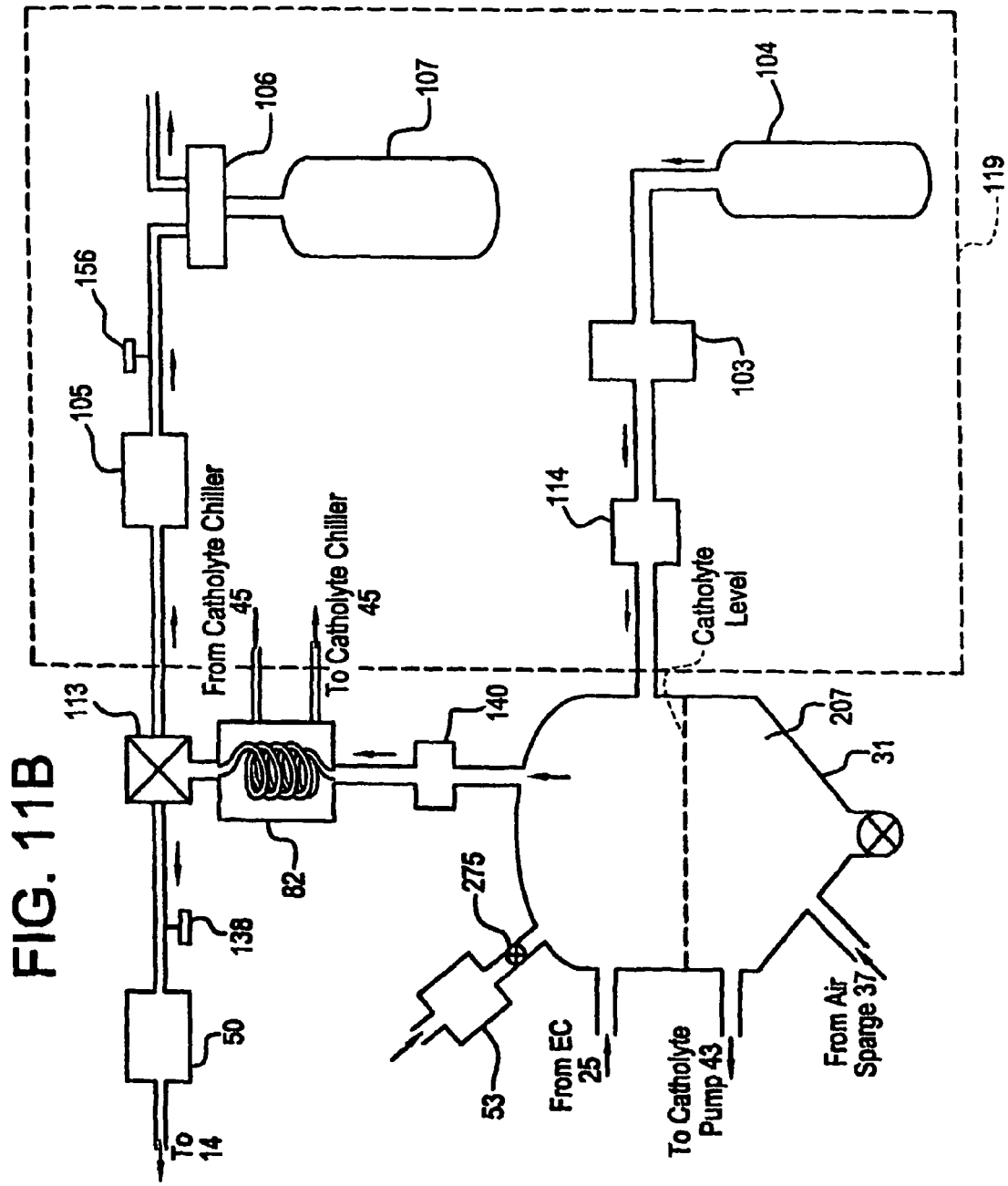
FIG. 11B Hydrogen Gas System 119 is a representation of the hydrogen system used to either capture the hydrogen generated at the cathode for future use (e.g., combustion or fuel cell, etc.) or to dilute it for release into the atmosphere. Captured hydrogen may be stored either as a compressed gas or as an interstitial solid state solution in a bulk (e.g., zirconium, Zircalloy, etc.).

FIG. 11B Hydrogen Gas System 119 is a representation of the hydrogen system used in the MEO apparatus. The catholyte solution 207 enters the catholyte reservoir 31 from the electrochemical cell 25 and returns from the catholyte reservoir 31 through the catholyte pump 43 to the catholyte system 205. Hydrogen exits the catholyte reservoir 31 and the amount of hydrogen is detected by a hydrogen gas detector 140. The hydrogen off gas passes through a catholyte demister 82. Chilled coolant flows from the catholyte chiller 45 to the catholyte demister 82 and returns to the catholyte chiller 45.

Two embodiments exist for the hydrogen generated in the catholyte reservoir 31 when selected catholytes are used. The PLC 98 controls through operator selection which of the two embodiments are to be used when the MEO apparatus 200 is operating. The air sparge 37 is used under the conditions described in the section on the catholyte system.

First, the hydrogen gas is not going to be collected for further use. In this case it is diluted by air entering the catholyte reservoir 31 through the catholyte air intake filter 53 when the catholyte air intake valve 275 is in the open position. The hydrogen selection valve 113 is positioned by commands from the PLC 98 to exhaust the diluted hydrogen through the exhaust fan 50 to the off-gas vent 14. The hydrogen gas detector 140 monitors the hydrogen to insure the percentage of hydrogen is at or below the regulated safe level. The sail switch 138 monitor the flow through the exhaust fan 50 to ensure the flow is adequate.

In the second embodiment the hydrogen gas is being collected for use by either a fuel cell system or a combustion system such as water heater. The catholyte air intake valve 275 is in the closed position. The hydrogen selection valve 113 is in the position to pass the hydrogen gas to hydrogen gas pump 105. The hydrogen gas pump 105 compresses the hydrogen which passes through a hydrogen gas regulator 106. The hydrogen sensor 156 measures the percentage of hydrogen gas flowing to the hydrogen gas regulator 106. The compressed hydrogen is stored in a pressurized hydrogen storage bottle 107. The hydrogen is released trough the hydrogen regulator 106 to the in use devises.

In both embodiments there is a nitrogen gas bottle 104 connected to the catholyte reservoir 31 through a nitrogen pressure regulator 103. The nitrogen is used to purge the hydrogen gas out of the catholyte reservoir and connecting components by opening the nitrogen purge valve 114.

In a third embodiment the hydrogen gas is captured by zirconium or Ziralloy getters. In this embodiment the hydrogen gas is absorbed by the getters for latter disposal.

MEO System Operational Cycles

The MEO apparatus 200 may be operated in either full automatic or manual modes. The manual mode is for maintenance and diagnostic purposes and is not for general use. The manual mode is pass word protected. The automated system mode renders the apparatus simple to operate and safe to use. The system and mechanical design is fail-safe for all operational cycles, to fully protect the operator, the equipment and the environment. A typical set of operational cycles for the MEO apparatus 200 could be: 1) the ADD WASTE/ Destruction Cycle which includes the Destruction or oxidation process; 2) the Solids Removal Cycle which is used to remove any solid residuals; 3) the ABORT Cycle which is used to stop the MEO process when necessary; 4) the Cleaning and Disinfection Cycle which is used to sterilize/disinfect objects and equipment; 5) the MANUAL Cycle which enables a full diagnostic and data analysis capability.

The control of the MEO apparatus 200 resides in the controller system 49 which is composed of a touch screen monitor 51, programmable logic controller (PLC) 98, signal conditioners 100, and a data logger 99. The status and progress of steps of a given operational cycle are tracked and displayed on the PLC Touch Screen monitor 51. All operating parameters; i.e., temperatures, positions, volumes, are available for display at all time.

The operator of the MEO apparatus 200 may select any of the cycles by means of the touch screen monitor 51. A full gamut of sensors discussed in this patent communicates the input and output conditions to the PLC 98, to automatically govern the operation of the apparatus and its components. The number of sensors may vary depending on the application of the apparatus.

The menu of operations on the monitor 51 may be expanded or modified without disturbing the basic architecture of the control unit. The PLC 98 contains numerical values for various parameters in the MEO apparatus 200 such as the temperature of the anolyte in the anolyte reaction chamber 25 as measured by the temperature sensor 120. The PLC 98 store values for these parameters as 'default' values which operate the MEO apparatus 200 normally without requiring them to be adjusted. Default parameters for the various operational cycles are easily reprogrammed in real-time, to suit short-term needs or changes.

The basic logic and sensor design for the ADD WASTE/ Destruction Cycle contains all of the operations of the MEO Apparatus 200, and will be described herewith as typical of all operational cycles, annotated above.

Full system control of the MEO Apparatus 200 is provided to an operator primarily from a touch screen monitor 51 interfaced to the PLC 98. Abort buttons 117 (not shown in figures), and the main power connection through the on/off buttons 74 (shown in FIGS. 13B and 13C), may be on the monitor 51 under the control of the PLC 98 or in another embodiment may be outside of the PLC 98.

When the power cord 78 is connected to the house electrical supply AC power is applied to the PLC 98. The PLC 98 controls the application of either AC or DC power throughout the MEO apparatus 200. The PLC 98 applies the power to the monitor 51 and displays the startup screen on the monitor 51.

The operator selects the appropriate operational cycle or sequence from a menu offered on the Home screen of the controller's touch screen monitor 51. Next, the operator is invited to confirm or re-set the default parameters, i.e., anolyte reaction chamber 5 and catholyte reservoir 31 volume capacities, various temperatures, pump speeds, operating delays, and any subsystems that need to be disabled as not required for the specific operation.

Upon confirmation of the selection, the PLC 98 initiates the operation by first testing the capacity of the Nitrogen gas system. The capacity necessary is determined so that there is sufficient reserve to operate all pressure operated actuators for the pending cycle, and to have sufficient reserve gas to properly diffuse any potential Hydrogen gas excursion.

After suitable nitrogen gas capacity is established, the nitrogen purge valve 114 is opened to pressurize the system. The chillers 23 and 45 are started and tested for proper operation. Coolant from the chillers 23 and 45 is directed to the demisters 55 and 82 to condense any water vapor that may be entrained in the exhaust air. When the temperature of the demisters 55 and 82 reach their operating level, the exhaust fans 50 is started to exhaust the anolyte reaction chamber 5 and catholyte reservoir 31 head space. Chassis fans (not shown in the figures) are also turned on at this time. When sufficient airflow is confirmed in the stack, by their sail switch 138, the anolyte reaction chamber 5 level sensors 132, 133, 134, and 135 are tested to determine if any liquid is resident in the anolyte reaction chamber 5. If the anolyte reaction chamber 5 is determined to be empty, the dump valve 92 is closed and the basic operating steps for the ADD WASTE/Destruction cycle are commenced. The locking latch 76 is unlocked to permit the lid 1 to be opened.

The volume of the fluids resident in the anolyte reservoir 2 determines the next steps in the operational cycle. If the resident volume of fluid exceeds the combined volume of liquids that can be accommodated in the anolyte reaction chamber 5, then it would be necessary to dewater the anolyte. The anolyte would be dewatered using the reverse osmosis system 83, 85, 86 thus reducing the volume in the anolyte system. When dewatering restores the anolyte fluid volume to its default level, the anolyte liquid is redirected through the electrochemical cell 25; destroying all organic waste materials. If the anolyte reservoir fluid volume is determined to be within the operating range, the destruction cycle is started directly. In both instances when the operating capacity of the apparatus is at or over limits, the door lid 1 remains locked precluding overloading the system with additional waste. In the third instance, if the fluid volume is measured to show that there is available capacity in the system, the door lid 1 interlocks will permit it to be opened to allow a measured addition of solid and liquid waste.

Next the water content on the catholyte fluid side is measured, and then adjusted in the same manner as the anolyte fluid. The only difference is the controller system 49 will alternatively connect the catholyte plumbing circuit to the dewatering system.

When the system signals there is available capacity, the door lid 1 interlocks release which enables the door lid 1 to be opened. The basket 3 that holds the solid waste opens and the operator may add additional waste into the anolyte reaction chamber 5. As liquid and/or solid waste is introduced into the anolyte reaction chamber 5, its volume is added to the volume of fluids already resident in the anolyte reservoir 2. The calculation of total waste always includes the volume of waste in both the anolyte reaction chamber 5 and the anolyte reservoir 2, because the total volume can not exceed the volume of the anolyte reaction chamber 5. When the total of all volumes reaches the operating capacity of the anolyte reaction chamber 5, an audible limit alarm is sounded. If the operator continues to add liquid waste that exceeds the upper limits of the operating range, a second warning alarm is sounded and the MEO apparatus 200 will be disabled until the situation can be corrected. The situation can be diagnosed and corrected by resorting to the Manual mode operation. The degree of management control or oversight to restore regular automated operation is established in the default setting operation, and can be easily programmed to reflect various levels of risk management philosophy since the manual mode is pass word protected.

When the door lid 1 is closed, it is locked down automatically which in turn triggers closure of the solid waste basket 3. The dump valve 92 opens releasing any liquid waste into the anolyte reservoir 2 where it mixes with the anolyte fluid. When the anolyte reaction chamber 5 registers that it is EMPTY, the dump valve 92 closes. If the anolyte reaction chamber 5 does not register EMPTY within 40 seconds, the fact will be displayed and the system switches to standby so the situation can be diagnosed and corrected.

After the dump valve 92 closes, a three-way valve is set to be at its anolyte reservoir 2 drain position. With the dump valve 92 set to drain the anolyte reservoir 2, the anolyte pump 19 and catholyte pump 43 are turned on, and their flow capacity determined. If flow capacity for either pump ever drops below 75% of their default setting for 40 seconds, the pumps will be turned off, and the fact displayed on the monitor 51. If during subsequent operations the pump flow is interrupted, the DC power to the electrochemical cell 25 will be turned off.

After the proper anolyte solution 203 and catholyte solution 207 flow is established, DC power 29 is sent to the electrochemical cell 25. Anolyte solution 203 flow and DC power 29 on the electrochemical cell 25 establishes the MEO oxidation or destruction process.

Whenever oxidation is occurring, the system tests itself for the production of hydrogen gas within the catholyte reservoir 31. The hydrogen gas may be collected for use in other system such as a fuel cell. When that is not the case, then the hydrogen gas is diluted before release to the atmosphere. In both cases the hydrogen gas level is measured in the head space of the catholyte reservoir 31. When hydrogen gas is being diluted, the level of hydrogen gas is measured to ensure that it does not exceed 2% of the volume of the exhaust stream gases. Should that occur, then the system will disable the oxidation process; turn off the electrochemical cell 25, maximize the cool down of the catholyte fluid, turn off the air supply to the catholyte reservoir 31, and deluge the catholyte reservoir 31 with nitrogen gas. The overall operation of the MEO apparatus 200 will be automatically aborted, sounding audible alarms and displaying that status on the PLC monitor 51.

As soon as the MEO oxidation process is initiated, the controller 98 will switch in the ultraviolet 11 and the ultrasonic 9 units, unless they have been disabled when defaults were set.

When the anolyte solution 203 operating level within the anolyte reaction chamber 5 is attained, a three way valve diverts and closes the anolyte reservoir 2 drain and opens the anolyte reaction chamber 5 drain, enabling the MEO oxidation process to take place within the anolyte reaction chamber 5 and electrochemical cell 25 plumbing circuit. At this time, the anolyte reaction chamber and catholyte reservoir heaters 24 and 46 are enabled. Thermal controls 21 and 22 help the controller system 49 maintain proper temperatures through the application of the anolyte chiller 23 and the anolyte heater 24; and the catholyte chiller 45 and heater 46. The controller system 49 determines power to the heaters and distribution of coolant fluid.

As the oxidation progresses, the $CO_2$ generated by the reaction is measured and recorded against a time reference. Concurrently, the oxidation reduction potential (ORP) is measured before and after the anolyte reaction chamber 5 and is measured along the same time continuum. The algorithm combines the rate of $CO_2$ generation and the ORP to determine the state of the oxidation of the waste. The ORP provides information on the concentration of oxidizers in the anolyte solution 203. The algorithm provides the indicator that there is no more material left to be destroyed. This process is self-regulating. If additional material is added to the anolyte reaction chamber 5 before the initial charge of material is consumed, $CO_2$ generation and the accompanying ORP level are reestablished accordingly. Other methods may be used to determine the rate of oxidation in the MEO apparatus.

When the algorithm signals that the destruction cycle has been completed, there are no more materials that may be oxidized. The controller system 49 turns off the electrochemical call 25, which in turn switches off the ultraviolet unit 11, the ultrasonic unit 9 and the heaters 24 and 46 for both the anolyte reaction chamber 5 and catholyte reservoir 31.

The next controller-ordered step in the process is to suppress any residual oxidizers that may be left in the anolyte solution 203. The controller system 49 actuates the valve that diverts the anolyte solution 203 through the Discharger 93 instead of the electrochemical cell 25, by means of the discharger input valve 281. The anolyte solution 203 is then pumped through the Discharger 93 until an ORP sensor, that measure oxidizer potential downstream of the discharger 93; signal that the oxidizer potential has been reduced to the appropriate default level (shown in FIG. 7A).

After the oxidizers have been mitigated, the controller system 49 returns the discharger input valve 281 to its original position, thereby pumping anolyte fluid back through the electrochemical cell circuit.

The oxidizer suppression action is directly followed by a series of steps to adjust the water levels in both the anolyte and catholyte sides of the MEO apparatus. In this embodiment, the reverse osmosis (RO) technology will be used and illustrated next in this operational cycle.

The fluid in the anolyte side of the system is adjusted first. After the anolyte solution 203 is fully transferred to the anolyte reservoir 2 by cycling of the dump valve 92, level sensors 132 through 137 measures its volume. If water is needed, the controller system 49 opens a valve to the water storage tank 81 until the requisite amount of fluid is transferred into the anolyte reservoir 2. On the other hand, if the volume in the anolyte reservoir 2 is deemed to be too great, indicating that there is a excess water residual from the oxidation process, the controller system 49 initiates the dewatering process, thereby removing and transferring the excess water into the storage tank 81. Next the water content on the catholyte fluid side is measured, and then adjusted in the same manner as the anolyte fluid. The only difference is the controller system 49 will alternatively connect the catholyte plumbing circuit to the dewatering system. If the water storage tank 81 becomes full, then the water may be expelled through the drain 12.

The controller system 49 will always complete the water adjustment process once it has been started. This will be the only time when the process cannot be interrupted to add new waste materials. As always, the status of the MEO process is displayed on the touch screen monitor 51.

After the water in the anolyte and catholyte fluid is adjusted to its default value, the ADD WASTE/Destruction cycle is completed and the fact displayed on the touch screen monitor 51. At that point in the process, an audible signal is periodically sounded to notify the operator of the completion of the process. After a default time has elapsed the MEO apparatus system begins it shutdown process.

Shutdown is accomplished by the controller system 49 by turning off the anolyte and catholyte pumps 19 and 43, opening the dump valve 92 to clear the anolyte reaction chamber 5, and resetting the three-way drain valve to the anolyte reservoir 2. The duct and chassis fans are turned off along with the chiller 24 and 45 and the DC power supply 29 disabled. The nitrogen system pressure is tested and repressurized if it is determined to be too low for subsequent operating cycle. After the $N_2$ pressure is assured, the controller system 49 switches off the signal voltage.

When the Main power is turned off manually by the on/off button 74, the PLC 98 goes into its dormant mode.

The operating cycle that was described is the basic destruction cycle as applied to the MEO apparatus represented by FIG. 1. This application has been constructed into a pre-production Unit and all of its programs and controls were successfully proofed and demonstrated. All of the other MEO applications cited within this document are determined by different arrangements of the various building blocks of the MEO apparatus; i.e., the anolyte and catholyte reservoirs 2 and 31, an electrochemical cell 25, an anolyte reaction chamber 5, anolyte and catholyte heater systems 24 and 46, cooling systems 23 and 45, pumps and plumbing 19, 43, 87, 92, de-watering capability, oxidizer suppression system 93 through 95, nitrogen purge system 103, 104, 114, automated and fail-safe controls 49, and mechanical interlocks for operator and environmental safety. The system and components design is completely scalable if some attention is given to power requirements and materials handling.

The MEO apparatus design is inherently capable of disinfecting and sterilizing itself during its regular oxidation process. This means it's capable of eradicating all living organisms including spores in all parts of its plumbing, reservoirs, and reaction chambers. During the dewatering cycles, or periodically as part of a sterilization and disinfection protocol, anolyte fluid with an appropriate but reduced level of oxidizers may be introduced into the dewatering system, which may not normally receive cleansing oxidizers. This capability would be routinely built into the MEO apparatus that utilizes reverse osmosis (RO) to dewater. The exact level of oxidizer that would be appropriate to a specific type and make of an RO unit may be easily established. The level of oxidizer strength that can adequately kill pathogens that may accompany the treated waste and bacterial colonies that sprout within the system may be selected. Care is taken to assure the oxidizer does not degrade the reverse osmosis (RO) unit's metal parts and membranes.

MEO Apparatus Safety

The MEO apparatus in this patent incorporates safety features to ensure its safe operation. The first safety issue with the MEO apparatus involves the materials handling and containment. The materials are introduced into the MEO apparatus where the MEO process begins to convert the materials to benign components as soon as the process begins.

The first procedures for safe handling of the materials before introduction into the MEO apparatus are established by Federal, state, and local statutes and regulations. After introduction into the MEO apparatus, the longer the process operates, the safer the materials become.

Figure 12:
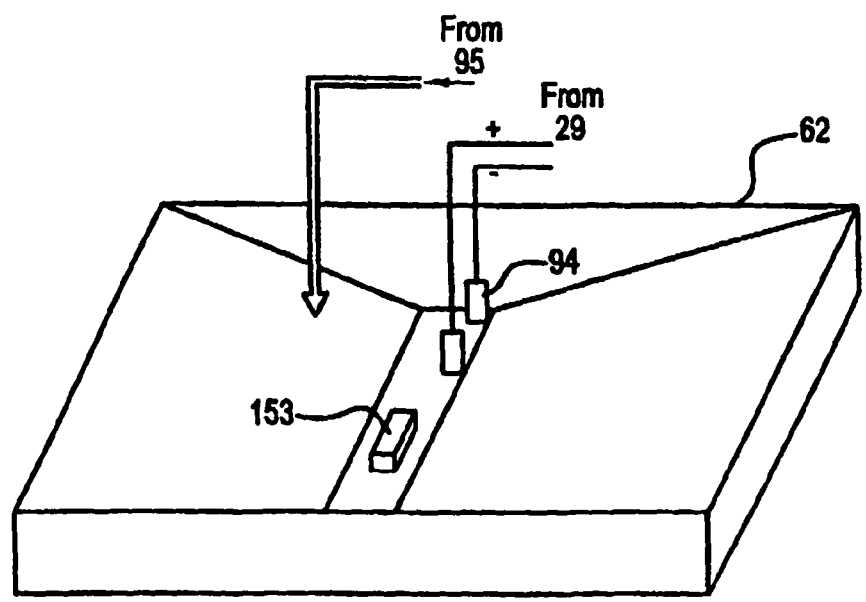
FIG. 12 MEO Apparatus Safety Containment Pan is a representation of a containment pan to hold spills or leaks in the MEO apparatus.

Secondly, an embodiment of the MEO apparatus has a containment pan 62 built into the MEO apparatus with the capacity to hold all the electrolytes (both anolyte and catholyte together) without spilling it outside the apparatus. The containment pan 62 may hold a neutralizing and absorbing agent to assist in the containment of the electrolytes. The electrolyte may be contained from either a leak or catastrophic failure from either the anolyte system and/or the catholyte system. FIG. 12 MEO Apparatus Safety Containment Pan is a representation of the containment pan 62. The containment pan 62 has a spill sensor 153 to detect the introduction of any electrolyte into the containment pan 62.

Thirdly, an embodiment of the MEO apparatus may automatically introduce a neutralizing and absorbing materials from the oxidizer suppress injection tank 95 injected into the containment pan 62 based on the sensor detecting electrolyte.

Fourthly, discharging plates 94 may be in the containment pan 62 to discharge the oxidizer in the electrolyte as soon as the sensor detects presences of electrolyte in the containment pan 62. The discharging plates 94 are powered by the DC power supply 29 or the AC power supply 30.

Fifthly, the MEO apparatus controller system 49, based on the sensors detecting malfunction of the MEO system such a flow rate change, leak detection, etc., may begin the abort cycle immediately.

Sixthly, the MEO apparatus controller monitors the MEO process to determine the state of completion of the disposal of the materials in the system. The controller system 49 reports the status of the materials disposal through the display monitor 51 and places the system in a standby mode when the disposal is complete.

Seventhly, the MEO apparatus may have a hydrogen detector 140 to measure the rate of hydrogen production in the catholyte reservoir 31 and a hydrogen detector 141 to detect hydrogen gas leaking into the chassis. In either case, the detectors will initiate a controlled safe shutdown the MEO apparatus should the hydrogen gas level exceed a safety limit. These sensors are shown in FIG. 1.

Applications of MEO Apparatus

The MEO process is a fully scalable technology. This feature is important in that it allows the MEO apparatus to be sized to the volume, throughput, and composition of the materials to be processed by the apparatus. The apparatus may be located as close to the source of the materials to be processed as practical, eliminating the need for additional handling, tracking systems, and transportation of these materials. The following MEO apparatus embodiments (depicted in FIGS. 13A through 13F) are typical of the diversity of design and applications of technology. FIGS. 13A through 13F depict exterior views of the MEO apparatus. Many of the foregoing figures depict the many possible interior configurations within these MEO apparatus. The components of these MEO apparatus that are viewable from the exterior are shown using the same numbers from Table 3 as viewed in the previous figures.

Figure 13A:
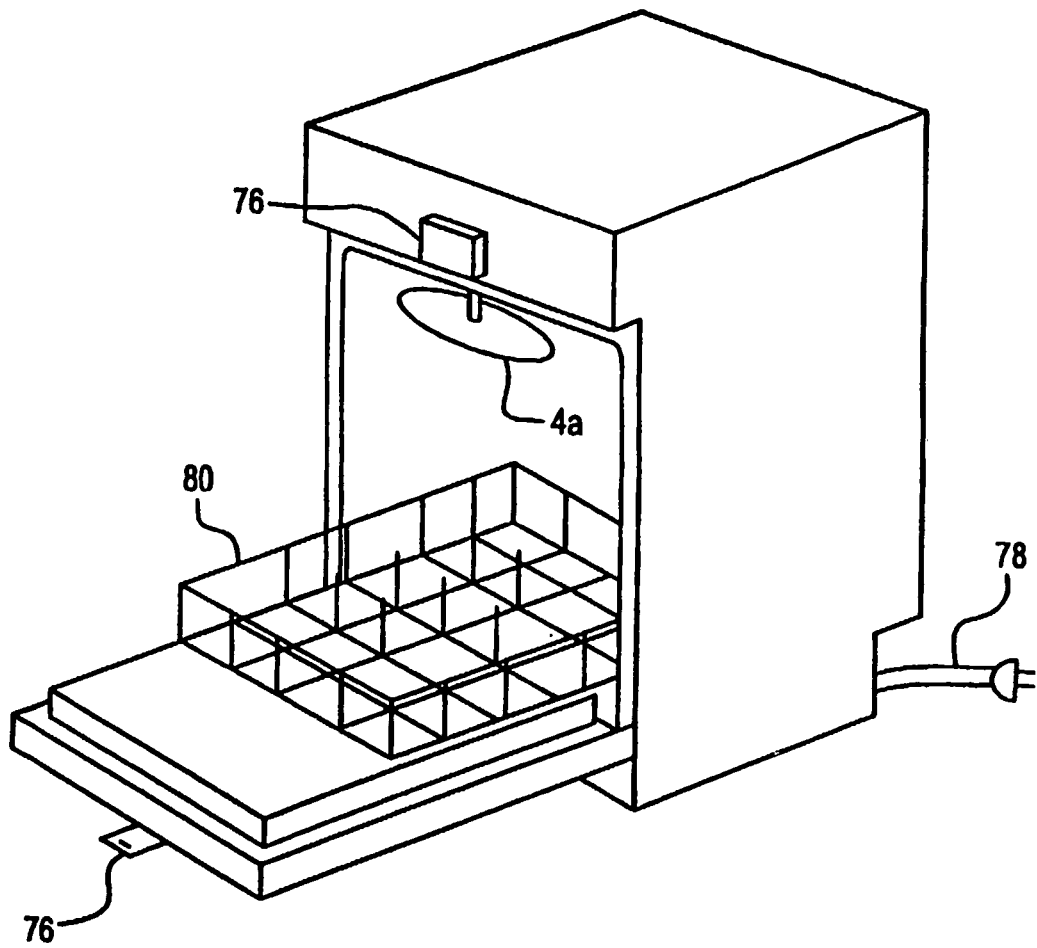
FIG. 13A Appliance Unit 289 is a schematic representation of a unit to sterilize/disinfection contaminated glassware and equipment.

FIG. 13A Appliance Unit 289. This MEO apparatus has the characteristics of laboratory, business or commercial size appliance. The apparatus handles a small volume of materials to be processed. Typically it is used to clean glassware, small equipment parts, instruments, etc. The apparatus may operate without a plumbing connection and with or without venting to the exterior. The appliance unit 289 may be used to decontaminate and sterilize contaminated items. An example of this appliance unit 289 is a waterless dishwasher or a laboratory glassware sterilizer.

The appliance unit 289 is powered by house power through the power cord 78. The utensils to be cleaned are placed in the utensil tray 80. The spray head 4a sprays fresh anolyte from the anolyte reaction chamber on the utensils. MEO apparatus unit 289 recovers some of the water from the anolyte after the cleaning cycle is complete and rinses the utensils with the spray head 4a. The locking latch 76 secures the door during the operating cycle.

Figure 13F:
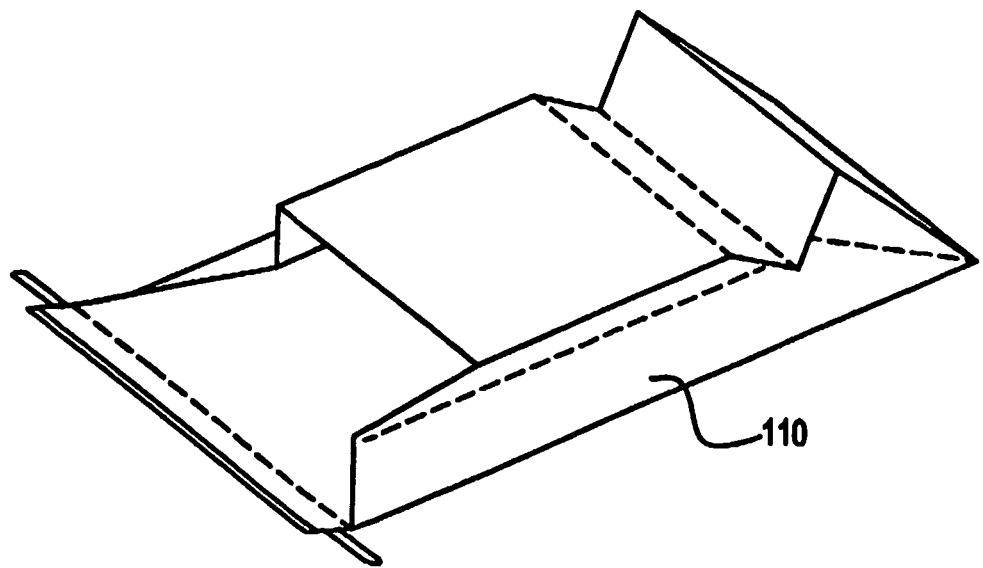
FIG. 13F Infectious Materials Container is a schematic representation of a disposable container for handling infectious waste prior to placement in the MEO apparatus.
Figure 13B:
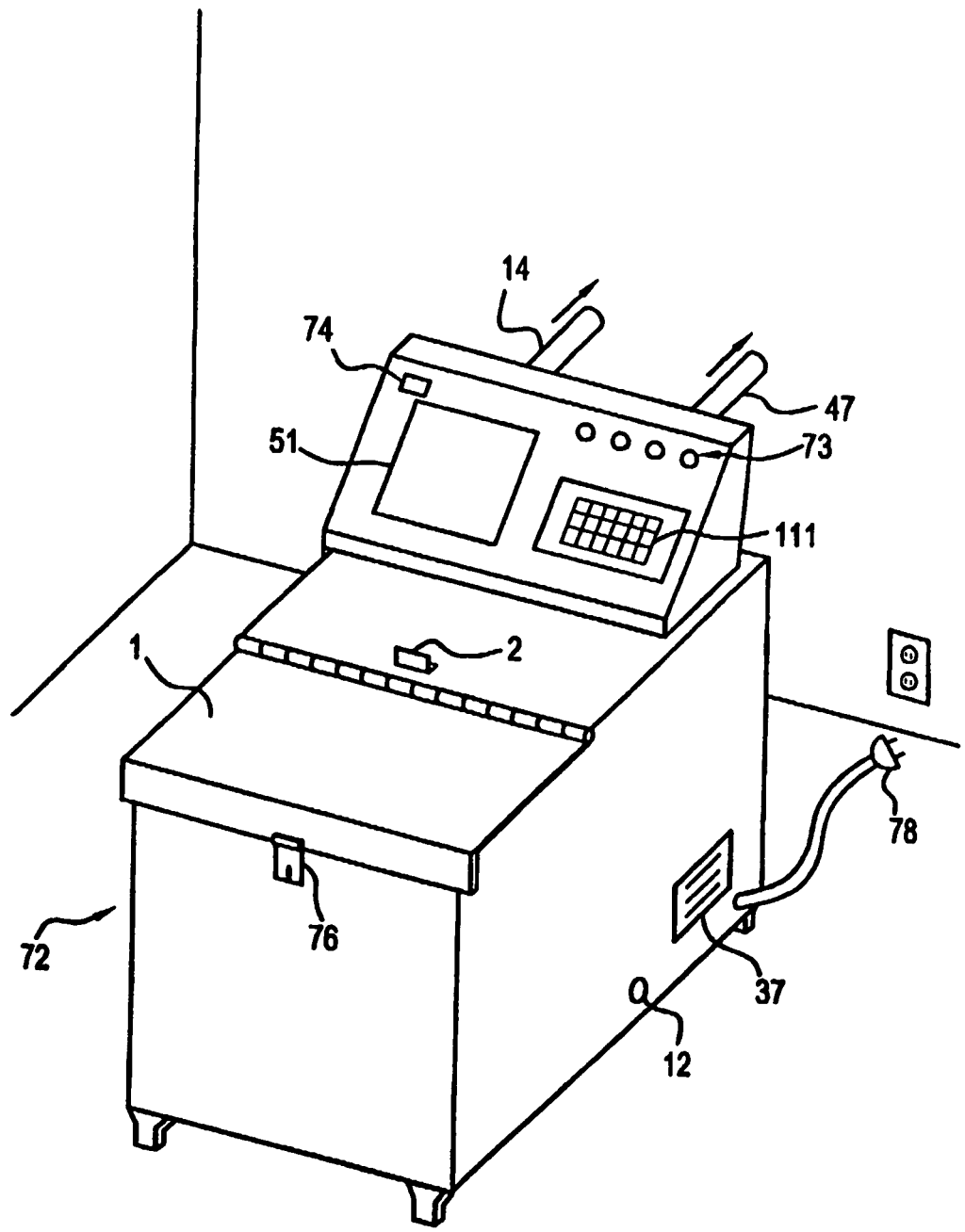
FIG. 13B Small Laboratory Office or Industrial Unit 291 is a schematic representation of a unit to process small amounts of liquids and/or solids.

FIG. 13B Small Laboratory Office or Industrial Unit 291. This embodiment has a small foot print (e.g., ten square feet or less) and may not require exterior venting and liquid discharge. The small laboratory, office, or industrial unit 291 handles small quantities in semi-continuous mode generally in the range from a few pound per day to a few pounds per hour. The materials are introduced into the small laboratory, office, or industrial unit 291 by opening the lock latch 76 and raising the lid 1. The small laboratory, office, or industrial unit 291 incorporates the controller system 49 internal to the MEO System Housing 72. The controller system 49 components (monitor 51, keyboard 111, status lights 73 and on/off button 74) are shown in the figure. Room air is drawn in through the air sparge 37. Any gas in the head room of the anolyte reaction chamber 5 and catholyte reservoir 31 that are internal to housing 72, may be vented to the atmosphere through the off-gas vent 14. The small laboratory, office, or industrial unit 291 is equipped with a drain 12 used to remove the anolyte and/or catholyte during maintenance. The small laboratory, office, or industrial unit 291 is powered by the house power through the power cord 78.

Figure 13C:
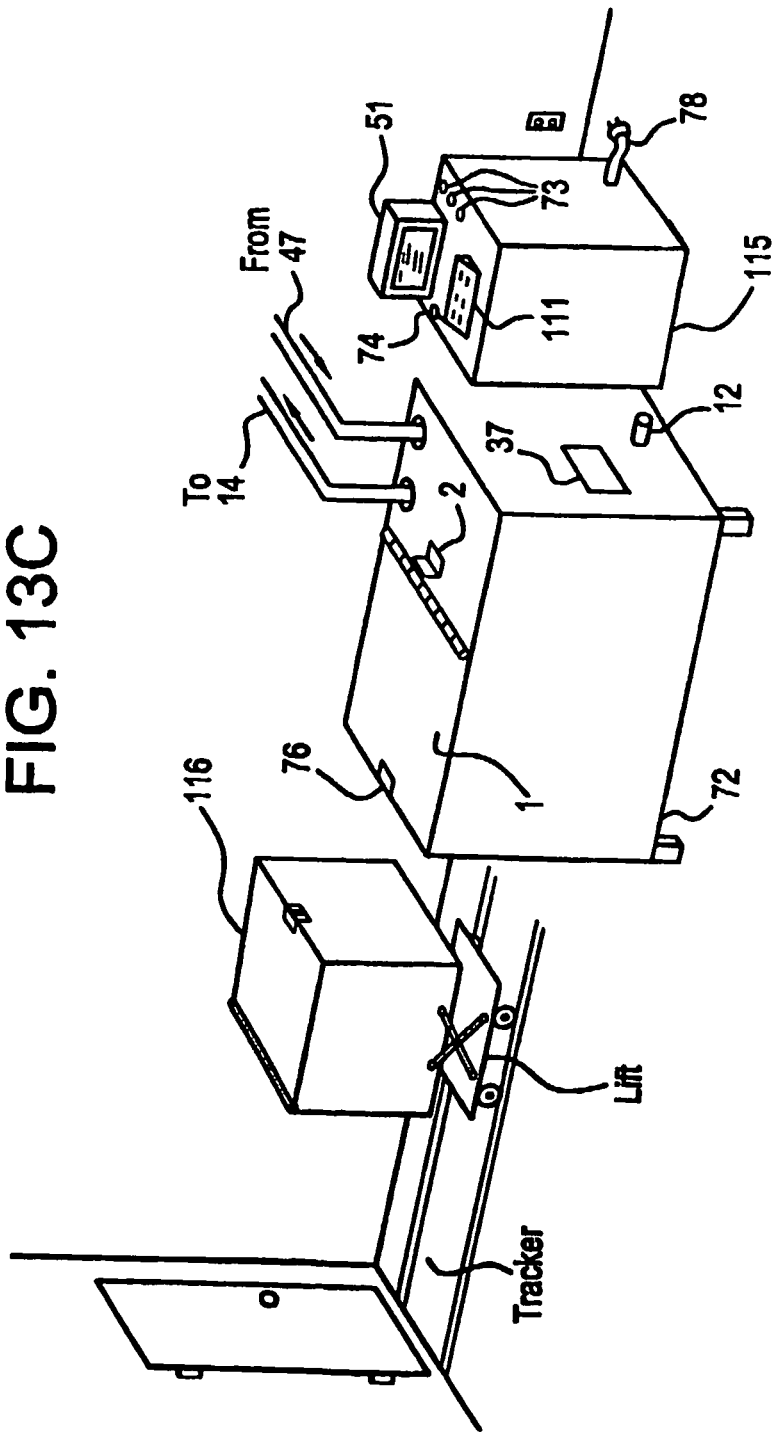
FIG. 13C Small to Mid-size Laboratory or Industrial Unit 293 is a schematic representation of a unit to process moderate amounts of liquids and/or solids.

FIG. 13C Small to Mid-size Laboratory, or Industrial Unit 293. This embodiment has a foot print of ten to thirty square feet. The small to mid-size laboratory or industrial unit 293 requires external venting and access to a clean water discharge connection. This small to mid-size laboratory or industrial unit 293 will handle a few pounds per hour to a hundred pounds per day. Typically this small to mid-size laboratory or industrial unit 293 will be used to process medical laboratory liquids, solids, and gases, or disposal of materials products from a small industrial process. FIG. 13C depicts a waste container 116 delivering waste to the small to mid-size laboratory, or industrial unit 293 on a lift to be introduced into the unit 293 by opening the lock latch 76 and raising lid 1. The two main sections of the small to mid-size laboratory, or industrial unit 293 are the MEO System Housing 72 and the MEO Controller Housing 115. The status lights 73, on/off buttons 74, keyboard 111, and monitor 51 are shown on the MEO Controller Housing 115. Any gas in the head room of the anolyte reaction chamber 5 and catholyte reservoir 31 that are internal to housing 72, may be vented to the atmosphere through the off-gas vent 14. The small to mid-size laboratory, or industrial unit 293 is equipped with a drain 12 used to remove the anolyte and/or catholyte during maintenance. The small to mid-size laboratory, or industrial unit 293 is connected to the house power system through power cord 78. Room air is drawn into the MEO apparatus through the air sparge 37.

Figure 13D:
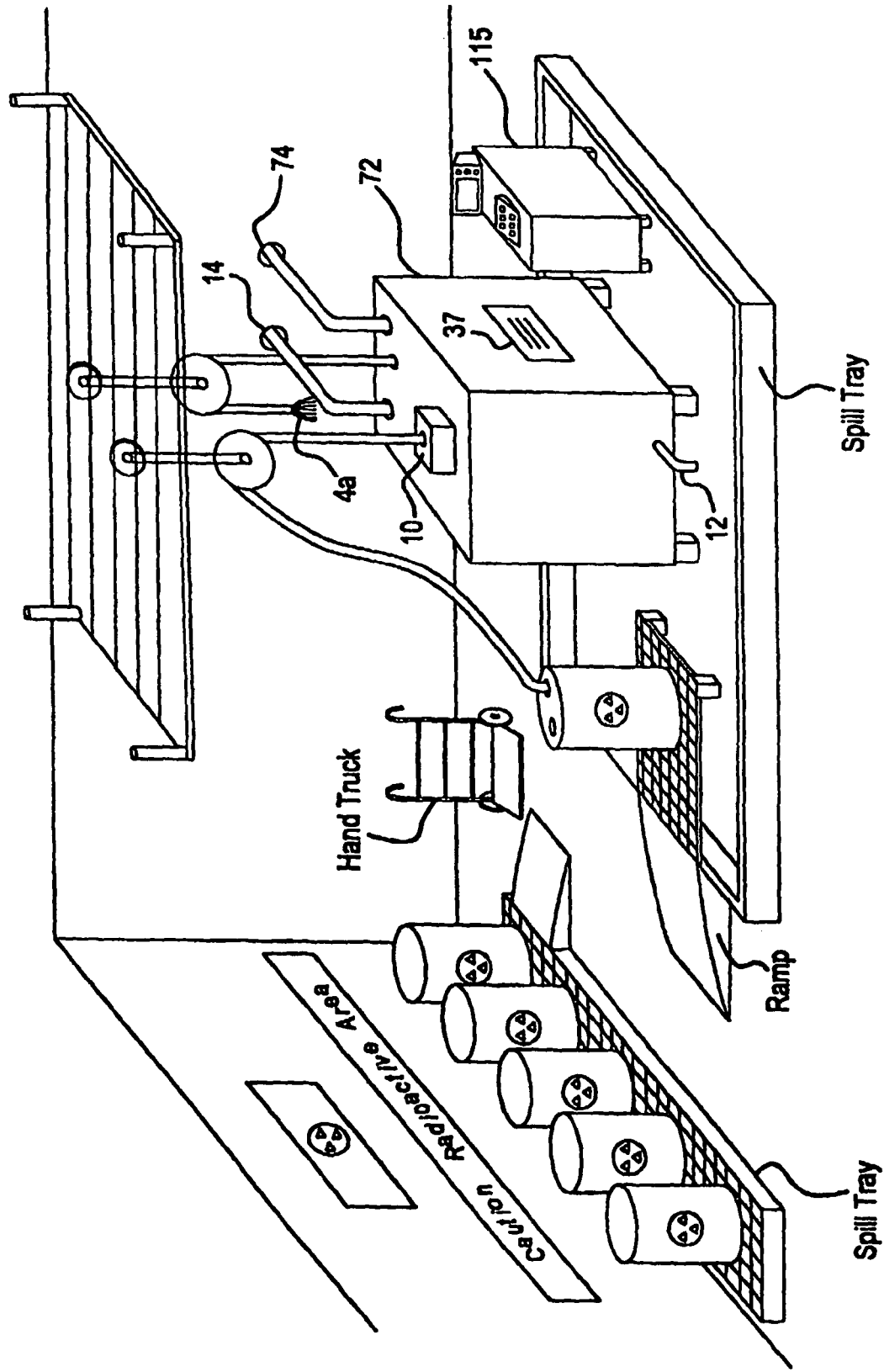
FIG. 13D Industrial Unit 295 is a schematic representation of an industrial unit that disposes of industrial materials products.

FIG. 13D Industrial Unit 295. This embodiment has a foot print of approximately one hundred to thousand square feet. The industrial unit 295 requires external venting and access to a clean water discharge connection. This industrial unit 295 will handle a hundred pounds per hour to a few thousand pounds per day. Typically this industrial unit 295 will be used to process animal or food materials liquids and solids or disposal of materials products from a manufacturing process (e.g., solvents in a metal fabrication shop). FIG. 13D depicts an industrial unit 295 that is disposing of halogenated hydrocarbons. The waste is pumped from the containers by input pump 10. The spray head 4a is shown in the figure. The spray head 4a is placed into the waste container to spray fresh anolyte from the anolyte reaction chamber 5 to clean the container after the waste has been processed in the industrial unit 295. The industrial unit 295 is composed of two sections the MEO system housing 72 and the MEO controller housing 115. Gases in the head room of the anolyte reaction chamber 5 and catholyte reservoir 31 that are internal to housing 72, may be vented to the atmosphere through the off-gas vent 14. Room air is drawn into the industrial unit 295 through the air sparge 37. The industrial unit 295 is equipped with a drain 12 used to remove the anolyte solution 203 and/or catholyte solution 207 during maintenance.

FIG. 13E Fuel Cell Unit 297. This embodiment is representative of a MEO apparatus that is producing hydrogen fuel for a fuel cell 288. The fuel cell unit 297 operates where there is a sufficient supply of materials to generate enough hydrogen to power the fuel cell 288. The waste material is pumped by input pump 10 from the waste tank 42 into the MEO system housing 72. The hoist 257 positions the waste input line 298 between the waste tank 42 and the MEO system housing 72. The housing 72 is secured during its operation by a locking latch 76. The fuel cell unit 297 incorporates the controller system 49 internal to the MEO System Housing 72. The hydrogen exits the catholyte reservoir 31 through the catholyte demister 82 that are internal to housing 72, and enters the fuel cell 288 through the hydrogen input tube 38 into the fuel cell 288. The fuel cell unit 297 has the capacity to generate oxygen to enrich the oxygen supply from the atmosphere. The oxygen mixed with the anolyte off-gases exits the anolyte reaction chamber 5 and passes through the off-gas condenser 13 and a carbon dioxide filter that are internal to the housing 72 and enters the fuel cell 288 through the oxygen input 40 Room air may be drawn into the fuel cell unit 297 through the air sparge 37. The fuel cell unit 297 is equipped with a drain 12 used to remove the anolyte and/or catholyte during maintenance. The fuel cell unit 297 is connected to the house power system through power cord 78. Other MEO apparatus embodiment can be designed to use the hydrogen as a combustion fuel for a burner (i.e., a hot water heater or boiler burner).

FIG. 13F Infectious Materials Container This embodiment is representative of a disposable container 110 used to handle infectious waste prior to placement in the MEO apparatus 200. The infectious materials container 110 is unique in that it is designed to protect the handler from contact with the material and it is composed of materials that are easily decomposed into carbon dioxide and water by the MEO apparatus 200. The infectious materials container holds solids and liquids and serves as a temporary storage container.

Each of the following patent(s)/co-pending applications are incorporated herein by reference in their entireties:

U.S. Pat. No. 6,402,932 issued Jun. 11, 2002.
U.S. application Ser. No. 10/263,810 filed Oct. 4, 2002.
U.S. application Ser. No. 10/127,604 filed Apr. 23, 2002.
U.S. Provisional Application Ser. No. 60/409,202 filed Sep. 10, 2002.
U.S. Provisional Application Ser. No. 60/398,808 filed Jul. 29, 2002.
PCT/US02/03249 filed Feb. 6, 2002.
PCT/US03/02151 based on U.S. Provisional Application Ser. No. 60/350,352 filed Jan. 24, 2002.
PCT/US03/02152 based on U.S. Provisional Application Ser. No. 60/350,377 filed Jan. 24, 2002.
PCT/US03/02153 based on U.S. Provisional Application Ser. No. 60/350,378 filed Jan. 24, 2002.
PCT/US03/13051 based on U.S. Provisional Application Ser. No. 60/375,430 filed Apr. 26, 2002.
PCT/US03/04065 filed Feb. 12, 2003.
PCT/US02/33732 based on U.S. Provisional Application Ser. No. 60/330,436 filed Oct. 22, 2001.
PCT/US02/32040 based on U.S. Provisional Application Ser. No. 60/327,306 filed Oct. 9, 2001.

Application of the MEO Apparatus and Process

The MEO apparatus and process have broad and far reaching applications to a number of different industries. The previous sections have shown a large variety of embodiments. It is necessary to identify the industries for which the MEO apparatus and process are applicable to understand this variety of embodiments. The embodiments of the various components of the MEO apparatus have specific applications in particular industries. It would be too lengthy to identify the various combinations of MEO apparatus (s), components, and MEO chemistries. The following list of industries is presented to identify the classes where the MEO apparatus and process may be applied.

Medical (including medical materials, infectious materials, sharps, pathological materials, sterilization and disinfection);

Veterinary Materials (including animal medical waste, whole research animals, etc.);

Pharmaceutical Materials (including out-of-date drugs, rejected drug production, illegal drugs, etc);

Animal Materials (including animal parts, animal excretions, beddings, etc.);

Animals (including laboratory research animals such as mice, rabbits, etc., and large animals such as swine, cows, etc.);

Food Materials (including food preparation, unconsumed and partially consumed, etc.);

Solid Residential Materials (including household trash, etc.);

Solid Commercial Materials (including paper, plastics, etc.);

Ship Materials (including government ships, commercial ships, and private ships and boats, etc.);

Municipal Sewage (including municipal sludge, etc.);

Mortuary Materials (including the disposal of body fluids, fluids used in embalming process, etc.);

Halogenated Hydrocarbons (includes most of the halogenated hydrocarbons except fluorinated hydrocarbons);

Military Materials (including both organic and inorganic products, etc.)

Transportation (including cleaning and disposing of materials carried in train tank cars, highway tank trucks, etc.);

Landfill (including hazardous runoff, hazardous materials, etc.);

Land Recover (including brown fields, soil remediation, etc.);

Energetics and Pyrotechnics (including explosive materials, etc.);

Herbicides and Pesticides (including disposal of herbicides and pesticides, cleaning contaminated equipment, etc.);

Mining (including gold and silver mine tailing, cyanides, and other process, etc.);

Carbon Compounds (including incinerator ash, etc.);

Metallurgical Industry (including metal plating, metal cleaning, etc.);

Transuranics/Actinides (including dissolution of transuranics/actinides, destroying mixed waste, etc.);

Chemical Intermediates (including decomposing organic compounds from a higher carbon content to molecules of lesser content to be used as intermediates in other chemical process, etc.);

Paper Industry (including the replacement of chlorine in the paper making and recycling process, etc.);

Ozone Generation at Low Voltage (including replacement for bleaching processes, disinfection, etc.)

Absorption of Volatile Organic Carbons (including the use of the MEO apparatus as a scrubber, etc.);

Chlorine Process Industry (including the replacement of chlorine as a bleach and/or as an oxidizer with an environmentally benign MEO process, etc.);

Chemical Fertilizers Industry (including the conversion of manures and municipal sludge to inorganic compounds to use as fertilizers, etc.);

Micro-processor Industry (including the replacement of hazardous solvents, cleaning and conditioning of printed circuit boards, etc.);

Halogenated Inorganic Industry (including all halogenated inorganic compounds except those containing fluorine); and Hydrogen Fuel Industry (including the generation of hydrogen for fuel cells, the generation of hydrogen for hydrogen burners for such items as water heaters and furnaces, etc.).

While the invention has been described with reference to specific embodiments, modifications and variations of the invention may be constructed without departing from the scope of the invention which is defined in the drawings and the following claims.

TABLE 1

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| I | A | None | | | |
|   | B | Copper (Cu) | +2 | $Cu^{-2}$ (cupric) | +2 Species/+3, +4 Species |
|   |   |   |   | $HCuO_2^-$ (bicuprite) | +3 Species/+4 Species |
|   |   |   |   | $CuO_2^{-2}$ (cuprite) | |
|   |   |   | +3 | $Cu^{+3}$ | |
|   |   |   |   | $CuO_2^-$ (cuprate) | |
|   |   |   |   | $Cu_2O_3$ (sesquioxide) | |
|   |   |   | +4 | $CuO_2$ (peroxide) | |
|   |   | Silver (Ag) | +1 | $Ag^+$ (argentous) | +1 Species/+2, +3 Species |
|   |   |   |   | $AgO^-$ (argentite) | +2 Species/+3 Species |
|   |   |   | +2 | $Ag^{-2}$ (argentic) | |
|   |   |   |   | $AgO$ (argentic oxide) | |
|   |   |   | +3 | $AgO^+$ (argentyl) | |
|   |   |   |   | $Ag_2O_3$ (sesquioxide) | |
|   |   | Gold (Au) | +1 | $Au^+$ (aurous) | +1 Species/+3, +4 Species |
|   |   |   | +3 | $Au^{+3}$ (auric) | +3 Species/+4 Species |
|   |   |   |   | $AuO^-$ (auryl) | |
|   |   |   |   | $H_3AuO_3^-$ (auric acid) | |
|   |   |   |   | $H_2AuO_3^-$ (monoauarate) | |
|   |   |   |   | $HAuO_3^{-2}$ (diaurate) | |
|   |   |   |   | $AuO_3^{-3}$ (triaurate) | |
|   |   |   |   | $Au_2O_3$ (auric oxide) | |
|   |   |   |   | $Au(OH)_3$ (auric hydroxide) | |
|   |   |   | +4 | $AuO_2$ (peroxide) | |
| II | A | Magnesium (Mg) | +2 | $Mg^{+2}$ (magnesic) | +2 Species/+4 Species |
|   |   |   | +4 | $MgO_2$ (peroxide) | |
|   |   | Calcium (Ca) | +2 | $Ca^{+2}$ | +2 Species/+4 Species |
|   |   |   | +4 | $CaO_2$ (peroxide) | |
|   |   | Strontium | +2 | $Sr^{+2}$ | +2 Species/+4 Species |
|   |   |   | +4 | $SrO_2$ (peroxide) | |
|   |   | Barium (Ba) | +2 | $Ba^{+2}$ | +2 Species/+4 Species |
|   |   |   | +4 | $BaO_2$ (peroxide) | |
| II | B | Zinc (Zn) | +2 | $Zn^{+2}$ (zincic) | +2 Species/+4 Species |
|   |   |   |   | $ZnOH^+$ (zincyl) | |
|   |   |   |   | $HZnO_2^-$ (bizincate) | |
|   |   |   |   | $ZnO_2^{-2}$ (zincate) | |
|   |   |   | +4 | $ZnO_2$ (peroxide) | |
|   |   | Mercury (Hg) | +2 | $Hg^{+2}$ (mercuric) | +2 Species/+4 Species |
|   |   |   |   | $Hg(OH)_2$ (mercuric hydroxide) | |
|   |   |   |   | $HHgO_2^-$ (mercurate) | |
|   |   |   | +4 | $HgO_2$ (peroxide) | |
| III | A | Boron | +3 | $H_3BO_3$ (orthoboric acid) | +3 Species/+4.5, +5 Species |
|   |   |   |   | $H_2BO_3^-, HBO_3^{-2}, BO_3^{-3}$ (orthoborates) | |
|   |   |   |   | $BO_2^-$ (metaborate) | |
|   |   |   |   | $H_2B_4O_7$ (tetraboric acid) | |
|   |   |   |   | $HB_4O_7^-/B_4O_7^{-2}$ (tetraborates) | |
|   |   |   |   | $B_2O_4^{-2}$ (diborate) | |
|   |   |   |   | $B_6O_{10}^{-2}$ (hexaborate) | |
|   |   |   | +4.5 | $B_2O_5^-$ (diborate) | |
|   |   |   | +5 | $BO_3^-/BO_2^-\cdot H_2O$ (perborate) | |
|   |   | Thallium (Tl) | +1 | $Tl^{+1}$ (thallous) | +1 Species/+3 or +3.33 Species |
|   |   |   | +3 | $Tl^{+3}$ (thallic) | +3 Species/+3.33 Species |
|   |   |   |   | $TlO^+, TlOH^{+2}, Tl(OH)_2^+$ (thallyl) | |
|   |   |   |   | $Tl_2O_3$ (sesquioxide) | |
|   |   |   |   | $Tl(OH)_3$ (hydroxide) | |
|   |   |   | +3.33 | $Tl_3O_5$ (peroxide) | |
|   | B | | | See Rare Earths and Actinides | |
| IV | A | Carbon (C) | +4 | $H_2CO_3$ (carbonic acid) | +4 Species/+5, +6 Species |
|   |   |   |   | $HCO_3^-$ (bicarbonate) | |
|   |   |   |   | $CO_3^{-2}$ (carbonate) | |
|   |   |   | +5 | $H_2C_2O_6$ (perdicarbonic acid) | |
|   |   |   | +6 | $H_2CO_4$ (permonocarbonic acid) | |

TABLE 1-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Germanium (Ge) | +4 | $H_2GeO_3$ (germanic acid)<br>$HGeO_3^-$ (bigermaniate)<br>$GeO_3^{-4}$ (germinate)<br>$Ge^{+4}$ (germanic)<br>$GeO_4^{-4}$<br>$H_2Ge_2O_5$ (digermanic acid)<br>$H_2Ge_4O_9$ (tetragermanic acid)<br>$H_2Ge_5O_{11}$ (pentagermanic acid)<br>$HGe_5O_{11}^-$ (bipentagermanate) | +4 Species/+6 Species |
| | | | +6 | $Ge_5O_{11}^{-2}$ (pentagermanate) | |
| | | Tin (Sn) | +4 | $Sn^{+4}$ (stannic)<br>$HSnO_3^-$ (bistannate)<br>$SnO_3^{-2}$ (stannate)<br>$SnO_2$ (stannic oxide)<br>$Sn(OH)_4$ (stannic hydroxide) | +4 Species/+7 Species |
| | | | +7 | $SnO_4^-$ (perstannate) | |
| | | Lead (Pb) | +2 | $Pb^{+2}$ (plumbous)<br>$HPbO_2^-$ (biplumbite)<br>$PbOH^+$<br>$PbO_2^{-2}$ (plumbite)<br>$PbO$ (plumbus oxide) | +2, +2.67, +3 Species/+4 Species |
| | | | +2.67 | $Pb_3O_4$ (plumbo-plumbic oxide) | |
| | | | +3 | $Pb_2O_3$ (sequioxide) | |
| IV | A | Lead (Pb) | +4 | $Pb^{+4}$ (plumbic)<br>$PbO_3^{-2}$ (metaplumbate)<br>$HPbO_3^-$ (acid metaplumbate)<br>$PbO_4^{-4}$ (orthoplumbate)<br>$PbO_2$ (dioxide) | +2, +2.67, +3 Species/+4 Species |
| | B | Titanium | +4 | $TiO^{+2}$ (pertitanyl)<br>$HTiO_4^-$ titanate)<br>$TiO_2$ (dioxide) | +4 Species/+6 Species |
| | | | +6 | $TiO_2^{+2}$ (pertitanyl)<br>$HTiO_4^-$ (acid pertitanate)<br>$TiO_4^{-2}$ (pertitanate)<br>$TiO_3$ (peroxide) | |
| | | Zirconium (Zr) | +4 | $Zr^{+4}$ (zirconic)<br>$ZrO^{+2}$ (zirconyl)<br>$HZrO_3^-$ (zirconate) | +4 Species/+5, +6, +7 Species |
| | | | +5 | $Zr_2O_5$ (pentoxide) | |
| | | | +6 | $ZrO_3$ (peroxide) | |
| | | | +7 | $Zr_2O_7$ (heptoxide) | |
| | | Hafnium (Hf) | +4 | $Hf^{+4}$ (hafnic)<br>$HfO^{+2}$ (hafnyl) | +4 Species/+6 Species |
| | | | +6 | $HfO_3$ (peroxide) | |
| V | A | Nitrogen | +5 | $HNO_3$ (nitric acid)<br>$NO_3^-$ (nitrate) | +5 species/+7 Species |
| | | | +7 | $HNO_4$ (pernitric acid) | |
| | | Phosphorus (P) | +5 | $H_3PO_4$ (orthophosphoric acid)<br>$H_2PO_4^-$ (monoorthophosphate)<br>$HPO_4^{-2}$ (diorthophosphate)<br>$PO_4^{-3}$ (triorthophosphate)<br>$HPO_3$ (metaphosphoric acid)<br>$H_4P_2O_7$ (pryophosphric acid)<br>$H_5P_3O_{10}$ (triphosphoric acid)<br>$H_6P_4O_{13}$ (tetraphosphoric acid) | +5 Species/+6, +7 species |
| | | Phosphorus (P) | +6 | $H_4P_2O_8$ (perphosphoric acid) | +5 Species/+6, +7 Species |
| | | | +7 | $H_3PO_5$ (monoperphosphoric acid) | |
| | | Arsenic (As) | +5 | $H_3AsO_4$ (ortho-arsenic acid)<br>$H_2AsO_4^-$ (mono ortho-arsenate)<br>$HAsO_4^{-2}$ (di-ortho-arsenate)<br>$AsO_4^{-3}$ (tri-ortho-arsenate)<br>$AsO_2^+$ (arsenyl) | +5 Species/+7 species |
| | | | +7 | $AsO_3^+$ (perarsenyl) | |
| | | Bismuth (Bi) | +3 | $Bi^{+3}$ (bismuthous)<br>$BiOH^{+2}$ (hydroxybismuthous)<br>$BiO^+$ (bismuthyl)<br>$BiO_2^-$ (metabismuthite) | +3 Species/+3.5, +4, +5 Species |
| | | | +3.5 | $Bi_4O_7$ (oxide) | |
| | | | +4 | $Bi_2O_4$ (tetroxide) | |
| | | | +5 | $BiO_3^-$ (metabismuthite)<br>$Bi_2O_5$ (pentoxide) | |

TABLE 1-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | B | Vanadium (V) (See also POM Complex Anion Mediators) | +5 | $VO_2^+$ (vanadic)<br>$H_3V_2O_7^-$ (pyrovanadate)<br>$H_2VO_4^-$ (orthovanadate)<br>$VO_3^-$ (metavanadate)<br>$HVO_4^{-2}$ (orthovanadate)<br>$VO_4^{-3}$ (orthovanadate)<br>$V_2O_5$ (pentoxide)<br>$H_4V_2O_7$ (pyrovanadic acid)<br>$HVO_3$ (metavanadic acid)<br>$H_4V_6O_{17}$ (hexavanudic acid) | +5 Species/+7, +9 Species |
| | | | +7 | $VO_4^-$ (pervanadate) | |
| | | | +9 | $VO_5^-$ (hypervanadate) | |
| VI | B | Chromium | +3 | $Cr^{+3}$ (chromic)<br>$CrOH^{+2}, Cr(OH)_2^+$ (chromyls)<br>$CrO_2^-, CrO_3^{-3}$ (chromites)<br>$Cr_2O_3$ (chromic oxide)<br>$Cr(OH)_3$ (chromic hydroxide) | +3 Species/+4, +6 Species<br>+4 Species/+6 Species |
| | | | +4 | $CrO_2$ (dioxide)<br>$Cr(OH)_4$ (hydroxide) | |
| | | | +6 | $H_2CrO_4$ (chromic acid)<br>$HCrO_4^-$ (acid chromate)<br>$CrO_4^{-2}$ (chromate)<br>$Cr_2O_7^{-2}$ (dichromate) | |
| | | Molybdenum (Mo) (See also POM Complex Anion Mediators) | +6 | $HMoO_4^-$ (bimolybhate)<br>$MoO_4^{-2}$ (molydbate)<br>$MoO_3$ (molybdic trioxide)<br>$H_2MoO_4$ (molybolic acid) | +6 Species/+7 Species |
| | | | +7 | $MoO_4^-$ (permolybdate) | |
| | | Tungsten (W) (See also POM Complex Anion Mediators) | +6 | $WO_4^{-2}$ tungstic)<br>$WO_3$ (trioxide)<br>$H_2WO_4$ (tungstic acid) | +6 Species/+8 Species |
| | | | +8 | $WO_5^{-2}$ (pertungstic)<br>$H_2WO_5$ (pertungstic acid) | |
| VII | A | Chlorine (Cl) | −1 | $Cl^-$ (chloride) | −1 Species/+1, +3, +5, +7 Species |
| | | | +1 | HClO (hypochlorous acid)<br>$ClO^-$ (hypochlorite) | +1 Species/+3, +5, +7 Species |
| | | | +3 | $HClO_2$ (chlorous acid)<br>$ClO_2^-$ (chlorite) | +3 Species/+5, +7 Species<br>+5 Species/+7 Species |
| | | | +5 | $HClO_3$ (chloric acid)<br>$ClO_3^-$ (chlorate) | |
| | | | +7 | $HClO_4$ (perchloric acid)<br>$ClO_4^-, HClO_5^{-2}, ClO_5^{-3}, Cl_2O_9^{-4}$ (perchlorates) | |
| V | B | Niobium (Nb) (See also POM Complex Anion Mediators) | +5 | $NbO_3^-$ (metaniobate)<br>$NbO_4^{-3}$ (orthoniobate)<br>$Nb_2O_5$ (pentoxide)<br>$HNbO_3$ (niobid acid) | +5 Species/+7 species |
| | | | +7 | $NbO_4^-$ (perniobate)<br>$Nb_2O_7$ (perniobic oxide)<br>$HNbO_4$ (perniobic acid) | |
| | | Tantalum (Ta) (See also POM Complex Anion Mediators) | +5 | $TaO_3^-$ (metatantalate)<br>$TaO_4^{-3}$ (orthotanatalate)<br>$Ta_2O_5$ (pentoxide)<br>$HTaO_3$ (tantalic acid) | +5 species/+7 species |
| | | | +7 | $TaO_4^-$ (pentantalate)<br>$Ta_2O_7$ (pertantalate)<br>$HTaO_4 \cdot H_2O$ (pertantalic acid) | |
| VI | A | Sulfur (S) | +6 | $H_2SO_4$ (sulfuric acid)<br>$HSO_4^-$ (bisulfate)<br>$SO_4^{-2}$ (sulfate) | +6 Species/+7, +8 Species |
| | | | +7 | $S_2O_8^{-2}$ (dipersulfate) | |
| | | | +8 | $H_2SO_5$ (momopersulfuric acid) | |
| | | Selenium (Se) | +6 | $H_2Se_2O_4$ (selenic acid)<br>$HSeO_4^-$ (biselenate)<br>$SeO_4^{-2}$ (selenate) | +6 species/+7 Species |
| | | | +7 | $H_2Se_2O_8$ (perdiselenic acid) | |
| | | Tellurium (Te) | +6 | $H_2TeO_4$ (telluric acid)<br>$HTeO_4^-$ (bitellurate)<br>$TeO_4^{-2}$ (tellurate) | +6 species/+7 species |
| | | | +7 | $H_2Te_2O_8$ (perditellenic acid) | |
| | | Polonium (Po) | +2 | $Po^{+2}$ (polonous) | +2, +4 species/+6 Species |
| | | | +4 | $PoO_3^{-2}$ (polonate) | |
| | | | +6 | $PoO_3$ (peroxide) | |

TABLE 1-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| VII | A | Bromine (Br) | −1 | $Br^-$ (bromide) | −1 Species/+1, +3, +5, +7 Species |
| | | | +1 | HBrO (hypobromous acid) | +1 Species/+3, +5, +7 Species |
| | | | | $BrO^-$ (hypobromitee) | +3 Species/+5, +7 Species |
| | | | +3 | $HBrO_2$ (bromous acid) | +5 Species/+7 Species |
| | | | | $BrO_2^-$ (bromite) | |
| | | | +5 | $HBrO_3$ (bromic acid) | |
| | | | | $BrO_3^-$ (bromate) | |
| | | | +7 | $HBrO_4$ (perbromic acid) | |
| | | | | $BrO_4^-, HBrO_5^{-2}, BrO_5^{-3}, Br_2O_9^{-4}$ | |
| | | | | (prebromates) | |
| | | Iodine | −1 | $I^-$ (iodide) | −1 Species/+1, +3, +5, +7 Species |
| | | | +1 | HIO (hypoiodus acid) | +1 Species/+3, +5, +7 Species |
| | | | | $IO^-$ (hypoiodite) | +3 Species/+5, +7 Species |
| | | | +3 | $HIO_2$ (iodous acid) | +5 Species/+7 Species |
| | | | | $IO_2^-$ (iodite) | |
| | | | +5 | $HIO_3$ (iodic acid) | |
| | | | | $IO_3^-$ (iodate) | |
| | | | +7 | $HIO_4$ (periodic acid) | |
| | | | | $IO_4^-, HIO_5^{-2}, IO_5^{-3}, I_2O_9^{-4}$ | |
| | | | | (periodates) | |
| | B | Manganese (Mn) | +2 | $Mn^{+2}$ (manganeous) | +2 Species/+3, +4, +6, +7 Species |
| | | | | $HMnO_2^-$ (dimanganite) | +3 Species/+4, +6, +7 Species |
| | | | +3 | $Mn^{+3}$ (manganic) | +4 Species/+6, +7 Species |
| | | | +4 | $MnO_2$ (dioxide) | +6 Species/+7 Species |
| | | | +6 | $MnO_4^{-2}$ (manganate) | |
| | | | +7 | $MnO_4^-$ (permanganate) | |
| VIII | Period 4 | Iron (Fe) | +2 | $Fe^{+2}$ (ferrous) | +2 Species/+3, +4, +5, +6 Species |
| | | | | $HFeO_2^-$ (dihypoferrite) | +3 Species/+4, +5, +6 Species |
| | | | +3 | $Fe^{+3}, FeOH^{+2}, Fe(OH)_2^+$ (ferric) | +4 Species/+5, +6 Species |
| | | | | $FeO_2^-$ (ferrite) | +5 Species/+6 Species |
| | | | +4 | $FeO^{+2}$ (ferryl) | |
| | | | | $FeO_2^{-2}$ (perferrite) | |
| | | | +5 | $FeO_2^+$ (perferryl) | |
| | | | +6 | $FeO_4^{-2}$ (ferrate) | |
| | | Cobalt (Co) | +2 | $Co^{+2}$ (cobalous) | +2 Species/+3, +4 Species |
| | | | | $HCoO_2^-$ (dicobaltite) | +3 Species/+4 Species |
| | | | +3 | $Co^{+3}$ (cobaltic) | |
| | | | | $Co_2O_3$ (cobaltic oxide) | |
| | | | +4 | $CoO_2$ (peroxide) | |
| | | | | $H_2CoO_3$ (cobaltic acid) | |
| | | Nickel (Ni) | +2 | $Ni^{+2}$ (nickelous) | +2 Species/+3, +4, +6 Species |
| | | | | $NiOH^+$ | +3 Species/+4, +6 Species |
| | | | | $HNiO_2^-$ (dinickelite) | +4 Species/+6 Species |
| | | | | $NiO_2^{-2}$ (nickelite) | |
| | | | +3 | $Ni^{+3}$ (nickelic) | |
| | | | | $Ni_2O_3$ (nickelic oxide) | |
| | | | +4 | $NiO_2$ (peroxide) | |
| | | | +6 | $NiO_4^{-2}$ (nickelate) | |
| VIII | Period 5 | Ruthenium (Ru) | +2 | $Ru^{+2}$ | +2 Species/+3, +4, +5, +6, +7, +8 Species |
| | | | +3 | $Ru^{+3}$ | +3 Species/+4, +5, +6, +7, +8 Species |
| | | | | $Ru_2O_3$ (sesquioxide) | +4 Species/+5, +6, +7, +8 Species |
| | | | | $Ru(OH)_3$ (hydroxide) | +5 Species/+6, +7, +8 Species |
| | | | +4 | $Ru^{+4}$ (ruthenic) | +6 Species/+7, +8 Species |
| | | | | $RuO_2$ (ruthenic dioxide) | +7 Species/+8 Species |
| | | | | $Ru(OH)_4$ (ruthenic hydroxide) | |
| | | | +5 | $Ru_2O_5$ (pentoxide) | |
| | | | +6 | $RuO_4^{-2}$ (ruthenate) | |
| | | | | $RuO_2^{+2}$ (ruthenyl) | |
| | | | | $RuO_3$ (trioxide) | |
| | | | +7 | $RuO_4^-$ (perruthenate) | |
| | | | +8 | $H_2RuO_4$ (hyperuthenic acid) | |
| | | | | $HRuO_5^-$ (diperruthenate) | |
| | | | | $RuO_4$ (ruthenium tetroxide) | |
| | | Rhodium (Rh) | +1 | $Rh^+$ (hyporhodous) | +1 Species/+2, +3, +4, +6 Species |
| | | | +2 | $Rh^{+2}$ (rhodous) | +2 Species/+3, +4, +6 Species |
| | | | +3 | $Rh^{+3}$ (rhodic) | +3 Species/+4, +6 Species |
| | | | | $Rb_2O_3$ (sesquioxide) | +4 Species/+6 Species |
| | | | +4 | $RhO_2$ (rhodic oxide) | |
| | | | | $Rh(OH)_4$ (hydroxide) | |
| | | | +6 | $RhO_4^{-2}$ (rhodate) | |
| | | | | $RhO_3$ (trioxide) | |

TABLE 1-continued

SIMPLE ANION REDOX COUPLES MEDIATORS

| GROUP | SUB GROUP | ELEMENT | VALENCE | SPECIES | SPECIFIC REDOX COUPLES |
|---|---|---|---|---|---|
| | | Palladium | +2 | $Pd^{+2}$ (palladous) | +2 Species/+3, +4, +6 Species |
| | | | | $PdO_2^{-2}$ (palladite) | +3 Species/+4, +6 Species |
| | | | +3 | $Pd_2O_3$ (sesquioxide) | +4 Species/+6 Species |
| | | | +4 | $PdO_3^{-2}$ (palladate) | |
| | | | | $PdO_2$ (dioxide) | |
| | | | | $Pd(OH)_4$ (hydroxide) | |
| | | | +6 | $PdO_3$ (peroxide) | |
| VIII | Period 6 | Iridium (Ir) | +3 | $Ir^{+3}$ (iridic) | +3 Species/+4, +6 Species |
| | | | | $Ir_2O_3$ (iridium sesquioxide) | +4 Species/+6 Species |
| | | | | $Ir(OH)_3$ (iridium hydroxide) | |
| | | | +4 | $IrO_2$ (iridic oxide) | |
| | | | | $Ir(OH)_4$ (iridic hydroxide) | |
| | | | +6 | $IrO_4^{-2}$ (iridate) | |
| | | | | $IrO_3$ (iridium peroxide) | |
| | | Platinum (Pt) | +2 | $Pt^{+2}$ (platinous) | +2, +3 Species/+4, +6 Species |
| | | | +3 | $Pt_2O_3$ (sesquioxide) | +4 Species/+6 Species |
| | | | +4 | $PtO_3^{-2}$ (palatinate) | |
| | | | | $PtO^{+2}$ (platinyl) | |
| | | | | $Pt(OH)^{+3}$ | |
| | | | | $PtO_2$ (platonic oxide) | |
| IIIB | Rare earths | Cerium (Ce) | +3 | $Ce^{+3}$ (cerous) | +3 Species/+4, +6 Species |
| | | | | $Ce_2O_3$ (cerous oxide) | +4 Species/+6 Species |
| | | | | $Ce(OH)_3$ (cerous hydroxide) | |
| | | | +4 | $Ce^{+4}$, $Ce(OH)^{+3}$, $Ce(OH)_2^{+2}$, | |
| | | | | $Ce(OH)_3^+$ (ceric) | |
| | | | | $CeO_2$ (ceric oxide) | |
| | | | +6 | $CeO_3$ (peroxide) | |
| | | Praseodymium (Pr) | +3 | $Pr^{+3}$ (praseodymous) | +3 species/+4 species |
| | | | | $Pr_2O_3$ (sesquioxide) | |
| | | | | $Pr(OH)_3$ (hydroxide) | |
| | | | +4 | $Pr^{+4}$ (praseodymic) | |
| | | | | $PrO_2$ (dioxide) | |
| | | Neodymium | +3 | $Nd^{+3}$ | +3 Species/+4 Species |
| | | | | $Nd_2O_3$ (sesquioxide) | |
| | | | +4 | $NdO_2$ (peroxide) | |
| | | Terbium (Tb) | +3 | $Tb^{+3}$ | +3 Species/+4 Species |
| | | | | $Tb_2O_3$ (sesquioxide) | |
| | | | +4 | $TbO_2$ (peroxide) | |
| IIIB | Actinides | Thorium (Th) | +4 | $Th^{+4}$ (thoric) | +4 Species/+6 Species |
| | | | | $ThO^{+2}$ (thoryl) | |
| | | | | $HThO_3^-$ (thorate) | |
| | | | +6 | $ThO_3$ (acid peroxide) | |
| | | Uranium (U) | +6 | $UO_2^{+2}$ (uranyl) | +6 Species/+8 Species |
| | | | | $UO_3$ (uranic oxide) | |
| | | | +8 | $HUO_5^-$, $UO_5^{-2}$ (peruranates) | |
| | | | | $UO_4$ (peroxide) | |
| | | Neptunium (Np) | +5 | $NpO_2^+$ (hyponeptunyl) | +5 Species/+6, +8 Species |
| | | | | $Np_2O_5$ (pentoxide) | +6 Species/+8 Species |
| | | | +6 | $NpO_2^{+2}$ (neptunyl) | |
| | | | | $NpO_3$ (trioxide) | |
| | | | +8 | $NpO_4$ (peroxide) | |
| | | Plutonium (Pu) | +3 | $Pu^{+3}$ (hypoplutonous) | +3 Species/+4, +5, +6 Species |
| | | | +4 | $Pu^{+4}$ (plutonous) | +4 Species/+5, +6 Species |
| | | | | $PuO_2$ (dioxide) | +5 Species/+6 Species |
| | | | +5 | $PuO_2^+$ (hypoplutonyl) | |
| | | | | $Pu_2O_5$ (pentoxide) | |
| | | | +6 | $PuO_2^{+2}$ (plutonyl) | |
| | | | | $PuO_3$ (peroxide) | |
| | | Americium (Am) | +3 | $Am^{+3}$ (hypoamericious) | |
| | | | +4 | $Am^{+4}$ (americous) | |
| | | | | $AmO_2$ (dioxide) | |
| | | | | $Am(OH)_4$ (hydroxide) | |
| | | | +5 | $AmO_2^+$ (hypoamericyl) | |
| | | | | $Am_2O_5$ (pentoxide) | |
| | | | +6 | $AmO_2^{+2}$ (americyl) | |
| | | | | $AmO_3$ (peroxide) | |

TABLE II

ELEMENTS PARTICIPATING AS HETEROATOMS IN HETEROPOLYANION COMPLEX ANION REDOX COUPLE MEDIATORS

| GROUP | SUB GROUP | ELEMENT |
|---|---|---|
| I | A | Lithium (Li), Sodium (Na), Potassium (K), and Cesium (Cs) |
|  | B | Copper (Cu), Silver (Ag), and Gold (Au) |
| II | A | Beryllium (Be), Magnesium (Mg), Calcium (Ca), Strontium (Sr), and Barium (Ba) |
|  | B | Zinc (Zn), Cadmium (Cd), and Mercury (Hg) |
| III | A | Boron (B), and Aluminum (Al) |
|  | B | Scandium (Sc), and Yttrium (Y) - (See Rare Earths) |
| IV | A | Carbon (C), Silicon (Si), Germanium (Ge), Tin (Sn) and Lead (Pb) |
|  | B | Titanium (Ti), Zirconium (Zr), and Hafnium (Hf) |
| V | A | Nitrogen (N), Phosphorous (P), Arsenic (As), Antimony (Sb), and Bismuth (Bi) |
|  | B | Vanadium (V), Niobium (Nb), and Tantalum (Ta) |
| VI | A | Sulfur (S), Selenium (Se), and Tellurium (Te) |
|  | B | Chromium (Cr), Molybdenum (Mo), and Tungsten (W) |
| VII | A | Fluorine (F), Chlorine (Cl), Bromine (Br), and Iodine (I) |
|  | B | Manganese (Mn), Technetium (Tc), and Rhenium (Re) |
| VIII | Period 4 | Iron (Fe), Cobalt (Co), and Nickel (Ni) |
|  | Period 5 | Ruthenium (Ru), Rhodium (Rh), and Palladium (Pd) |
|  | Period 6 | Osmium (Os), Iridium (Ir), and Platinum (Pt) |
| IIIB | Rare Earths | All |

TABLE 3

NUMBERED FIGURE COMPONENTS

| COMPONENT NUMBER | COMPONENT NAME |
|---|---|
| 1 | Hinged Lid |
| 2 | Anolyte Reservoir (AR) |
| 3 | Waste Basket |
| 3a | Waste Basket Top |
| 4a | Spray Head |
| 4b | Stream Head |
| 4c | Bubble Head |
| 4d | Spray Head |
| 4e | Stream Head |
| 5, 5a, 5b, 5c, 5d, 5e | Anolyte Reaction Chamber (ARC) |
| 6 | ARC Filter |
| 6a | ARC Filter |
| 6b | ARC Filter |
| 6c | ARC Filter |
| 7 | Mixer |
| 8 | AR Pump |
| 9 | Ultrasonic source |
| 10 | Input Pump ARC |
| 11 | Ultraviolet Source |
| 12 | Drain |
| 13 | Condenser (off-gas) |
| 14 | Off-gas Vent |
| 15 | Inorganic Removal System |
| 16 | Gas Cleaning System |
| 17 | Organic Compounds Removal System |
| 18 | Liquefier (not shown in Figures) |
| 19 | Anolyte Pump |
| 20 | Fluoropolymer/copolymer Membrane |
| 21 | Thermal Control (anolyte) |
| 22 | Thermal Control (anolyte) |
| 23 | Anolyte Chiller |
| 24 | Anolyte Heater |
| 25, 25a, 25b | Electrochemical Cell(s) |
| 26 | Anode |
| 27 | Membrane |
| 27a | Composite Membrane |
| 28 | Cathode |
| 29 | DC Power Supply |
| 30 | AC Power Supply |
| 31 | Catholyte Reservoir |
| 32 | Air Pump |
| 33 | Catholyte Reservoir Lid |
| 34 | Penetrator |
| 35 | Mixer Catholyte |
| 36 | Lid Lever |
| 37 | Air Sparge |
| 38 | Hydrogen Input |
| 40 | Oxygen Input |
| 41 | Anolyte Recovery System |
| 42 | Waste Tank |
| 43 | Catholyte Pump |
| 44 | Catholyte Air Intake Filter |
| 45 | Catholyte Chiller |
| 46 | Catholyte Heater |
| 47 | Catholyte Vent |
| 48 | Ultrasonic Source (Catholyte) |
| 49 | Controller System |
| 50 | Exhaust Fan |
| 51 | Monitor |
| 52 | Anode Bus |
| 53 | Filter/Flash Arrestor CR |
| 54 | Cathode Bus |
| 55 | Anolyte Demister |
| 56 | Electrode Slot |
| 57 | Second Stage Anolyte RO Pump |
| 58 | Membrane Frame |
| 59 | RO Membrane Housing |
| 59a | RO Membrane Multipass Housing |
| 59b | Ro Membrane Housing |
| 60 | Clamp Holes |
| 61 | Second Stage Catholyte RO Pump |
| 62 | Containment Pan |
| 63 | Dilute Electrolyte Reservoir |
| 64 | Baffle |
| 65 | Osmotic pump |
| 66 | Pressure Regulator |
| 67 | Osmotic Membrane |
| 68 | Gas Pump |
| 69 | Gaseous Waste Source |
| 70 | Pressure Vessel |
| 71 | Reverse Osmosis (RO) Reservoir |
| 72 | MEO System Housing |
| 73 | Status Lights |
| 74 | On/Off Button |
| 75 | Nanofilter |
| 76 | Locking Latch |
| 77 | Condenser |
| 78 | Power Cord |
| 79 | Clean Water Pumps |
| 80 | Utensil tray |
| 81 | Water Storage Tank |
| 82 | Catholyte Demister |
| 83 | Anolyte RO Pump |
| 84 | Anolyte Air Intake Filter |
| 85 | Anolyte RO Membrane |
| 86 | Osmotic Reservoir |
| 87 | Catholyte RO Pump |
| 88 | Osmotic Cell |
| 89 | Catholyte RO membrane |
| 90 | Vacuum Pump |
| 91 | Anolyte Make-up Tank (not shown in Figures) |
| 92 | Dump Valve |
| 93 | Discharger |
| 94 | Discharging Electrodes |
| 95 | Suppression Tank |
| 96 | Evaporator |
| 97 | Suppression Injector |
| 98 | Programmable Logic Controller (PLC) |
| 99 | Data Logger |
| 100 | Signal Conditioner |
| 101 | Ethernet Connection |
| 102 | Telephone Connection |

TABLE 3-continued

NUMBERED FIGURE COMPONENTS

| COMPONENT NUMBER | COMPONENT NAME |
|---|---|
| 103 | Nitrogen Pressure Regulator |
| 104 | Nitrogen Gas Bottle |
| 105 | Hydrogen Gas Pump |
| 106 | Hydrogen Regulator |
| 107 | Hydrogen Storage Bottle |
| 108 | Video Camera |
| 109 | Ultrafilter |
| 110 | Infectious Materials Container |
| 111 | Keyboard |
| 113 | Hydrogen Selection Valve |
| 114 | Nitrogen Purge Valve |
| 115 | MEO Controller Housing |
| 116 | Waste Container |
| 117 | Abort Button (not shown in Figures) |
| 118 | Nitrogen Gas System |
| 119 | Hydrogen Gas System |
| 160 | Manual Gas Valve |
| 161 | Nitrogen Instruments Enable Valve |
| 162 | Instrument Nitrogen Pressure Regulator |
| 163 | Actuator Nitrogen Pressure Regulator |
| 164 | Catholyte Reservoir Purge Regulator |
| 165 | Catholyte Reservoir Purge valve |
| 200 | MEO Apparatus |
| 201 | Anolyte System |
| 203 | Anolyte Solution |
| 205 | Catholyte System |
| 207 | Catholyte Solution |
| 209 | Anolyte Off-gas Handling System |
| 211 | Catholyte Off-gas Handling System |
| 213 | Fluoropolymer/copolymer Based RO Unit |
| 214 | Discharger Input Valve |
| 215 | RO Unit with Discharger |
| 216 | Discharger Output Valve |
| 217 | Multipass RO Unit |
| 219 | RO Unit Rejecting to Catholyte |
| 220 | Static RO Unit |
| 222 | Osmotic Cell |
| 223 | Dilute Electrolyte |
| 224 | Selected Osmotic Fluid Cell |
| 225 | Inlet Tube |
| 226 | Dilute Electrolyte Valve |
| 227 | Vacuum Evaporation Unit |
| 230 | Water Reservoir |
| 231 | Separate Housing |
| 232 | Basic MEO Housing |
| 233 | Anolyte Input Tube to ARC |
| 235 | Anolyte Exit Tube |
| 237 | Anolyte Off-gas Exit Tube |
| 239 | Return Gas Tube Outlet |

TABLE 3-continued

NUMBERED FIGURE COMPONENTS

| COMPONENT NUMBER | COMPONENT NAME |
|---|---|
| 241 | Tube to Anolyte Off-gas System |
| 242 | Air Intake Valve Catholyte |
| 243 | Tube to Anolyte Pump 19 |
| 244 | Air Sparge Valve |
| 245 | Off-gas Handling Selection Valve |
| 246 | Tube from Electrochemical Cell 25 |
| 247 | Anolyte Off-gas Discharge Line |
| 248 | Catholyte Off-gas Discharge Line |
| 249 | Anolyte Condensate Return Tube |
| 250 | Catholyte Condensate Return Tube |
| 251 | Housing External |
| 253 | Anolyte Conduits |
| 255 | Catholyte Conduits |
| 257 | Hoist |
| 259 | Valve |
| 261 | Catholyte Dewatering Tube |
| 263 | Dewater Reject Tube |
| 265 | Valve |
| 267 | Tube |
| 268 | Tube from EC to CR |
| 269 | Dewatered Osmotic Valve |
| 270 | Ceramic Box |
| 270a | Pier Box |
| 271 | Lid |
| 272 | Gasket |
| 273 | Tube from CR to Catholyte Pump |
| 274 | Anolyte Input Tube |
| 275 | Catholyte Air Intake Valve |
| 276 | Anolyte Output Tube |
| 277 | Ridges |
| 278 | Catholyte Input Tube |
| 279 | Grooves |
| 280 | Catholyte Output Tube |
| 281 | Discharger Input Valve |
| 282 | DC/AC Switch |
| 283 | Water Reservoir Valve |
| 284 | Lid |
| 285 | Valve |
| 286 | Injection Valve |
| 287 | Osmotic Fluid |
| 288 | Fuel Cell |
| 289 | Appliance Unit |
| 291 | Small Lab, Office, or Industrial Unit |
| 293 | Small to Mid-size lab, or Industrial Unit |
| 295 | Industrial Unit |
| 297 | Fuel Cell Unit |
| 298 | Waste Input Line |
| 299 | Gaseous Materials Supply System |

TABLE 4

MEO Apparatus Sensors and Instrumentation

| COMPONENT NUMBER | SENSOR FUNCTION | TYPE OF SENSOR | PURPOSE |
|---|---|---|---|
| 120 | Temperature | Type K T/C | Temperature of ARC |
| 121 | Temperature | Type K T/C | Temperature of ARC Heater |
| 122 | Temperature | Type K T/C | Temperature after Anolyte Chiller2 |
| 123 | Temperature | Type K T/C | Temperature in AR |
| 124 | Temperature | Type K T/C | Temperature of off-gas from ARC |
| 125 | Temperature | Type K T/C | Temperature in CR |
| 126 | Temperature | Type K T/C | Temperature of CR off-gas |
| 127 | Temperature | Type K T/C | Temperature of CR Heater |
| 128 | Temperature | Type K T/C | Temperature after Catholyte Chiller |
| 129 | Fluid flow | Flow meter | Anolyte flow rate |
| 130 | Fluid flow | Flow meter | Flow of reject fluid from anolyte or catholyte RO processing |
| 131 | Fluid flow | Flow meter | Catholyte flow rate |
| 132 | Fluid level | Ultrasonic | Fluid level ARC |

TABLE 4-continued

MEO Apparatus Sensors and Instrumentation

| COMPONENT NUMBER | SENSOR FUNCTION | TYPE OF SENSOR | PURPOSE |
|---|---|---|---|
| 133 | Fluid level | Level meter | ARC overfill |
| 134 | Fluid level | Ultrasonic | Fluid level in AR |
| 135 | Fluid level | Level meter | AR overfill |
| 136 | Fluid level | Ultrasonic | Fluid level in the CR |
| 137 | Fluid level | Level meter | CR overfill |
| 138 | Gas Flow | Sail switch | Off-gas flow in anolyte vent |
| 139 | Gas Flow | $CO_2$ detector | Detects $CO_2$ in anolyte vent |
| 140 | Gas Flow | $H_2$ detector | $H_2$ gas flow in catholyte vent detector |
| 141 | Gas Flow | $H_2$ detector | Detects $H_2$ gas in chassis |
| 142 | Pressure | Pressure gauge | Pressure in anolyte RO unit |
| 143 | Pressure | Pressure gauge | Pressure in catholyte RO unit |
| 144 | Redox Potential | ORP | ORP in Anolyte input to EC |
| 145 | Redox Potential | ORP | ORP in Anolyte output from EC |
| 146 | Redox Potential | ORP | ORP in ARC exit line |
| 147 | Redox Potential | ORP | ORP in AR exit line |
| 148 | Redox Potential | ORP | ORP in Catholyte input to EC |
| 149 | Redox Potential | ORP | ORP in Catholyte output from EC |
| 150 | Redox Potential | ORP | ORP into discharger tank |
| 151 | Redox Potential | ORP | ORP exit stream from discharger tank |
| 152 | Measure pH | pH meter | Measures pH in the catholyte fluid |
| 153 | Spill detection | Resistance meter | Detects spills collected in the containment pan |
| 154 | Ultraviolet | Detects ultraviolet | Detect ultraviolet light operating |
| 155 | Air Flow | Detects air flow | Air Sparge Sensor |
| 156 | Hydrogen Sensor | Percentage $H_2$ | Measures percentage of hydrogen in stored gas |

We claim:

1. Apparatus for treating and oxidizing materials comprising first and second electrochemical cells for various embodiments and other appropriate applications, wherein all surfaces in the first electrochemical cell that come into contact with the electrolyte are made of material selected from the group consisting of polyvinylidene fluoride (PVDF), polypropylene (PP), ethylene-chlorotrifluoroethylene, polytetrafluoroethylene (PTFE), and combinations thereof, further comprising cell materials selected from the group consisting of fiberglass, polypropylene, metals, composite metals, and combinations thereof, the second electrochemical cell comprising a box, a lid, and input and exit tubings through the lid to allow anolyte and/or catholyte to enter and exit respectively through the tubings to and from the second electrochemical cell, the box and lid being composed of metal(s) and/or metal composites and the surfaces of the second electrochemical cell in contact with the electrolytes are coated with a glass glaze or metallic oxides, wherein the second cell containing the anolyte is connected by anolyte conduits in the wall of the second electrochemical cell so that the anolyte solution flows through the entire second electrochemical cell and wherein the first cell containing the catholyte is connected by catholyte conduits in the wall of the first electrochemical cell, thereby enabling easy maintenance through ease of access to the interior of the box and to the membranes.

2. The apparatus of claim 1, further comprising a dewatering system, further comprising a dewatering system having reverse osmosis (RO) units comprising a fluoropolymer/copolymer RO Unit having a membrane of a fluoropolymer/copolymer, wherein the fluoropolymer/copolymer membrane is used for dewatering of the anolyte by an RO unit when the oxidizer being used in the MEO apparatus would damage a membrane made from typical RO membrane materials and wherein cleaning of oxidizable material from the fluoropolymer/copolymer membrane is accomplished by the action of the oxidizer in the anolyte solution as it passes through the RO unit, a multipass RO unit for a dewatering unit where the osmotic pressure head is so large that the pressure limit on the RO membranes may be exceeded or the membrane partition factor may be insufficient to affect the required degree of separation in a single stage, wherein the anolyte or catholyte is pumped by pumps through the RO membrane, RO tubes made out of the RO membrane fill insides of the RO membrane housing, and wherein a dilute solution of the electrolyte is used for lowering the osmotic pressure between the anolyte and catholyte, a dilute electrolyte reservoir for storing the dilute electrolyte which is pumped by a second stage anolyte pump or second stage catholyte pump as the tube side liquid enters into a RO membrane multipass housing, osmotic pressure difference between the tube side liquid and the shell side pure water stream allows operation below pressure limits on the RO membrane, static RO unit wherein volume of the anolyte is relatively small and the flow rate through the RO membrane is low per unit area thus requiring greater flow area such that the total volume of the tubes required for this surface area exceeds the total anolyte volume.

3. The apparatus of claim 1, further comprising a dewatering tube for controlling levels of the catholyte by dewatering when levels exceed a set level by flowing the catholyte back through a dewater reject tube, valve for controlling liquid flowing through the dewatering tube for the adding of returned catholyte or rejecting water makeup from a water storage tank, wherein after the discharging process is complete the discharger output valve opens to the RO pump and the discharged anolyte solution is processed through the RO membrane which is enclosed in the RO membrane housing, and wherein anolyte RO pressure is sensed by a pressure sensor, water storage tank for storing pure water and a valve controlling supply of the water as needed to the dilute electrolyte, RO unit rejecting to catholyte wherein the anolyte and the catholyte are similar in composition and the RO membranes tolerate the electrolytes, wherein excess water in the anolyte is rejected into the catholyte through the RO membrane, wherein the RO again uses the anolyte solution pumped by the pump as the tube side fluid in the RO membrane housing, and wherein the catholyte solution is pumped by the pump through the shell side, returning the anolyte and the catholyte leaving the housing to the anolyte and the catholyte chambers, respectively, a valve opened to allow all the anolyte solution to be transferred from anolyte system through pump into the RO system tubes in the RO membrane housing, high pressure pump for pressurization of the RO system, RO reservoir is pressurized to several thousand psi with air or nitrogen from the pressurized vessel and let stand until the dewatering has reached the desired goal, a regulator for controlling pressure in the RO system by releasing the air or nitrogen gas from the pressurized vessel until the desired pressure has been reached in the RO system and for holding that pressure until the dewatering is complete, a regulator for holding the anolyte under pressure in the RO membrane in the housing and/or a nitrogen pressure vessel for holding the catholyte under pressure with the catholyte RO pump, a regulator for controlling pressure in the RO system by releasing the air or nitrogen gas from the pressurized vessel until the desired pressure has been reached in the RO system and for holding that pressure until the dewatering is complete, storage tank for storing processed water passing through the membrane, wherein the stored water is available to be returned to either the anolyte or the catholyte or to be rejected from the MEO apparatus, a particulate filter for passing the anolyte and/or catholyte solution exiting the apparatus to remove particulate matter, clean water pump coupled to the cells for pumping clean water into the anolyte chamber and/or the catholyte chamber for restoring levels of the catholyte.

4. The apparatus of claim 1, further comprising an osmotic cell wherein the anolyte and the catholyte have properties such that osmotic pressure drives water from anolyte side to catholyte side of the semi-permeable membrane, wherein the osmotic cell is pressurized on the anolyte side to increase flow and to dewater the anolyte by driving water from the anolyte to the catholyte, an osmotic cell with selected osmotic fluid wherein the catholyte has too low an osmotic pressure difference and the water in the anolyte will not cross the osmotic membrane, and wherein a second osmotic fluid with a higher osmotic pressure is provided to permit water to pass through the membrane, osmotic cell comprises two separate chambers wherein the anolyte and/or the catholyte flow along one side of an osmotic membrane and wherein another side of the osmotic membrane is in contact with an osmotic fluid having an osmotic pressure that allows water in the anolyte or catholyte to cross the osmotic membrane, an osmotic reservoir for storing the osmotic fluid, a pump for pumping the osmotic fluid from the osmotic reservoir through the osmotic cell and back to the osmotic reservoir, and an osmotic valve for dewatering the anolyte or the catholyte by operating the valve to allow flow into the RO membrane housing containing the RO membranes.

5. The apparatus of claim 1, further comprising a vacuum evaporation unit for removing water from the anolyte and/or catholyte vacuum evaporation, nanofilters for pretreatment of the materials to remove solids and soluble substances from the anolyte feed stream to the evaporator avoiding air-borne infectious release, wherein filtered anolyte and/or catholyte flows into the evaporator, and from the evaporator returns to the anolyte and/or the catholyte chambers and continue to circulate through the vacuum evaporator unit until excess, water in the solutions are reduced to desired levels, vacuum pump for reducing pressure in the evaporator system to less than a vapor pressure of water in the anolyte and/or catholyte at their respective temperatures, and a condenser connected to the system wherein water evaporates and progresses into the condenser, wherein pressure in the evaporator condenser system is controlled by vapor pressure of water at the condenser temperature.

6. The apparatus of claim 1, further comprising a nitrogen gas system comprising a nitrogen gas bottle having a gas valve for opening and closing the nitrogen gas bottle, wherein the gas valve is closed when the nitrogen gas bottle is being removed from the MEO apparatus and when the gas valve is opened a nitrogen pressure regulator controls the nitrogen gas pressure to the nitrogen gas system, and wherein the nitrogen gas pressure regulator is controlled by commands from the PLC, nitrogen gas system is used to purge the catholyte reservoir if hydrogen gas exceeds a two percent level in the off-gas handling system, catholyte reservoir purge regulator which is opened by a command from the PLC allowing nitrogen gas to flow and/or to purge the catholyte reservoir and a catholyte reservoir purge valve closes the catholyte air sparge so that the nitrogen purges the catholyte reservoir.

7. The apparatus of claim 1, further comprising a hydrogen gas system wherein the catholyte solution enters the catholyte reservoir from the first and second electrochemical cells and returns from the catholyte reservoir through the catholyte pump to the catholyte system and hydrogen exits the catholyte reservoir and the amount of hydrogen is detected by a hydrogen gas detector, wherein the hydrogen off-gas passes through a catholyte demister, and chilled coolant flows from a catholyte chiller to the catholyte demister and returns to the catholyte chiller, wherein the hydrogen gas is not collected for further use and is diluted by air entering the catholyte reservoir through the catholyte air intake filter when the catholyte air intake valve is in the open position, wherein the hydrogen selection valve is positioned by commands from the PLC to exhaust the diluted hydrogen through the exhaust fan to the off-gas vent, wherein the hydrogen gas is collected for use by either a fuel cell system or a combustion system such as a water heater, wherein the catholyte air intake valve is in the closed position, the hydrogen selection valve is in the position to pass the hydrogen gas to hydrogen gas pump which compresses the hydrogen which passes through a hydrogen gas regulator, a hydrogen sensor measures the percentage of hydrogen gas flowing to the hydrogen gas regulator, compressed hydrogen is stored in a pressurized hydrogen storage bottle and hydrogen is released through the hydrogen regulator to devices in use.

8. The apparatus of claim 1, further comprising a discharger comprising two or more electrodes between which the anolyte flow is directed during the discharge process is introduced in the anolyte flow stream, a discharger input valve is opened to allow the anolyte to enter the discharger, and a discharger output valve is opened to permit the flow of the anolyte leaving the discharger to flow through the sensor back to the anolyte chamber, further comprising low voltage AC or DC electro potential applied between adjacent discharger electrodes selected so as to cathodically reduce the oxidizer species present in the anolyte without causing their production via anodic oxidation, wherein the low voltage discharges the oxidizers in the anolyte and the discharger provides electrons to the oxidizers when they are returned to their reduced form, an oxidation reduction potential (ORP) sensor senses the oxidized mediators in the anolyte being discharged which circulates through the discharger until the mediator oxidation potential reaches a pre-determined level.

9. The apparatus of claim 1, wherein the first and second electrochemical cells have a molded unibody construction and the lid is coupled to the box, slots in the box for holding frames, wherein the frames receive and hold the membranes in liquid-tight manner to keep the anolyte and catholyte separated, comprising porous electrodes so that electrolyte flows through the electrodes and contacts both sides of the electrodes, a gasket in the lid for creating a tight seal, interior walls in the box for separating the anolyte from the catholyte, electrodes including anodes and cathodes in slots in the ceramic walls and electrical connections to the electrodes passing through the lid to anode bus and cathode bus, walls of the box having ridges and grooves to promote turbulent flow thereby reducing adverse boundary layer related phenomena at the anodes, plurality of electrochemical cells coupled together and having a pier box and lid, nuts and bolts and clamp holes on the box and/or lid for coupling the lid to the box as well as providing easy access to interior of the electrochemical cell significantly improving the maintenance of the electrochemical cells, interior surfaces having PTFE coating to protect the surfaces from oxidizers in the anolyte and acids or alkaline in the catholyte, glazed inside surfaces of the box and the lid to protect the ceramic walls from the oxidizer in the anolyte solution and the acids or alkaline in the catholyte solution, comprising oxidation resistant ion selective membranes bonded over interior walls serving as ceramic membranes for supplementing performance of the ceramic membranes, wherein some of the interior walls are ion selective semi-permeable membranes.

10. The apparatus of claim 1, further comprising platinum wires and/or miniature ORP electrodes in each chamber of the anolyte and catholyte chambers positioned such that the electrical potential may be measured between the chambers to provide information of the concentration of oxidizer in the anolyte chamber and also as an indicator of any leakage in the membrane, concentration level may be controlled by varying the DC current in the first and second electrochemical cells, oxidizer level may be controlled by diverting some of the anolyte into the discharger and back to the cell.

11. Apparatus of claim 1 for treating and oxidizing materials comprising a fully scalable technology sizable to volume, throughput, and composition of materials to be processed, further comprising materials selected from the group consisting of:

medical (including medical materials, infectious materials, sharps, pathological materials, sterilization and disinfection); veterinary materials (including animal medical waste, whole research animals); pharmaceutical materials (including out-of-date drugs, rejected drug production, illegal drugs); animal materials (including animal parts, animal excretions, beddings); animals (including laboratory research animals such as mice, rabbits, and large animals such as swine, cows); food materials (including food preparation, unconsumed and partially consumed); solid residential materials (including household trash); solid commercial materials (including paper, plastics); ship materials (including government ships, commercial ships, and private ships and boats); municipal sewage (including municipal sludge); mortuary materials (including the disposal of body fluids, fluids used in embalming process); halogenated hydrocarbons (includes most of the halogenated hydrocarbons except fluorinated hydrocarbons); military materials (including both organic and inorganic products), transportation (including cleaning and disposing of materials carried in train tank cars, highway tank trucks); landfill materials(including hazardous runoff, hazardous materials); land recover (including brown fields, soil remediation); energetics and pyrotechnics (including explosive materials); herbicides and pesticides (including disposal of herbicides and pesticides, cleaning contaminated equipment); mining (including gold and silver mine tailing, cyanides, and other process); carbon compounds (including incinerator ash); metallurgical industry (including metal plating, metal cleaning); transuranics/actinides (including dissolution of transuranics/actinides, destroying mixed waste); chemical intermediates (including decomposing organic compounds from a higher carbon content to molecules of lesser content to be used as intermediates in other chemical process); paper industry (including the replacement of chlorine in the paper making and recycling process); ozone generation at low voltage (including replacement for bleaching processes, disinfection); absorption of volatile organic carbons (including the use of the MEO apparatus as a scrubber); chlorine process industry (including the replacement of chlorine as a bleach and/or as an oxidizer with an environmentally benign MEO process); chemical fertilizers industry (including the conversion of manures and municipal sludge to inorganic compounds to use as fertilizers); micro-processor industry (including the replacement of hazardous solvents, cleaning and conditioning of printed circuit boards); halogenated inorganic industry (including all halogenated inorganic compounds except those containing fluorine); and hydrogen fuel industry (including the generation of hydrogen for fuel cells, the generation of hydrogen for hydrogen burners for such items as water heaters and furnaces), and combinations thereof.

12. Apparatus comprising a mediated electrochemical oxygen system for treating and oxidizing materials further comprising an electrochemical cell, wherein the electrochemical cell has a molded unibody construction box and a lid is coupled to the box, interior walls in the box, plural membranes in the box, slots in the interior walls for holding membranes, wherein the slots receive and hold the membranes in liquid-tight manner, anolyte and catholyte in the box separated on opposite sides of the plural membranes, porous electrodes positioned in the box so that the anolyte and the catholyte flow through the electrodes and contact both sides of the electrodes, a gasket between the box and the lid for creating a tight seal, wherein the interior walls in the box are connected to the plural membranes for separating the anolyte from the catholyte, wherein the electrodes include anodes and cathodes extending from the slots in the walls and electrical connections connected to the DC power supply and to the electrodes and passing through the lid to an anode bus and a cathode bus on the lid.

13. The apparatus of claim 12, further comprising
  (1) an anolyte reservoir coupled to the anolyte chamber,
  (2) a dump valve for connecting the anolyte reservoir to the anolyte chamber,
  (3) dump valve connecting the anolyte chamber and the anolyte reservoir allowing for the anolyte and contents of the anolyte reaction chamber to be stored in the anolyte reservoir, wherein anytime the lid to the anolyte chamber is opened for access, the dump valve is opened prior to opening the lid such that the liquid contents of the anolyte chamber drops into the anolyte reservoir thereby avoiding potential contact of the anolyte with the user, a waste basket to hold solids in the anolyte chamber; input pump for introducing materials in continuous feed operations into the anolyte chamber and wherein the input pump is connected to a source of the materials to be destroyed, the materials are pumped into the chamber which contains the anolyte used to destroy these materials, and the apparatus continuously circulates the anolyte solution directly from the electrochemical cell through inlet tube into the anolyte chamber to maximize the concentration of oxidizing species contacting the materials includes
  (1) a filter located at the base of the anolyte chamber to limit the size of the solid particles flowing from anolyte chamber thereby preventing solid particles large enough to interfere with the flow in the electrochemical cell from exiting the anolyte chamber,
  (2) a lever connected to the anolyte chamber lid for lowering the basket into the anolyte when the lid and the waste basket are closed such that all of the basket's contents are held submerged in the anolyte throughout the MEO process,
  (3) a seal around the opening of the anolyte chamber lid,
  (4) gaseous material supply system connected to the anolyte chamber for supplying gaseous materials in continuous feed operations, wherein the gaseous materials to be processed are pumped from the gaseous material supply into a pressure vessel,
  (5) a regulator on the pressure vessel for controlling release of the materials into the anolyte chamber which contains the anolyte for destroying the gaseous materials, comprising bubble heads for introducing the gaseous materials into the anolyte chamber assuring that the gas entering the gas stream is in the form of small bubbles to create a large surface area on which the anolyte acts to oxidize the gaseous materials, the gaseous materials contact the anolyte in a counter current flow and wherein the gaseous materials are introduced into a lower portion of the anolyte chamber through the gaseous materials supply system, further wherein a stream of freshly oxidized anolyte solution directly from the electrochemical cell is introduced into the upper portion of the anolyte reaction chamber through an inlet tube enabling the gaseous materials to continuously react with oxidizing mediator species in the anolyte as the gas rises up in the anolyte chamber past the downward flowing anolyte and wherein the gaseous materials reaching a top of the anolyte chamber has the lowest concentration of oxidizable species and is also in contact with the anolyte having highest concentrations of oxidizer species,
  (6) comprising baffles in the anolyte chamber for regulating progress of the gaseous materials through the anolyte in the anolyte chamber,
  (7) liquefier for emulsifying the materials introduced into the anolyte chamber thereby greatly increasing the area of contact between the materials and oxidizers during the electrochemical process and increasing the materials destruction rate,
  (8) injector for injecting new anolyte into the anolyte chamber if and as required.

14. The apparatus of claim 12, further comprising a controller system comprising computing devices including automated programmable logic controllers (PLCs) coupled to pneumatic controls and system sensors for monitoring the process performed by the MEO apparatus, displaying data and status information on a monitor relative to the monitoring, executing operational cycles in the MEO apparatus, providing methodology to change parameters in the MEO process through digital control over system components including flow control of the anolyte and the catholyte, electrochemical cell power, off-gas systems, ultraviolet and ultrasound systems, further wherein the controller system comprises methodology to monitor and change the MEO parameters including numerous mediator and electrolyte combinations, and wherein the controller system maintains a record of operation of the MEO apparatus for post operation analysis using data recorded in the data logger, comprise storing on the PLC default values for typical parameters such as percent pump flow rate, anolyte and catholyte volume capacity, anolyte and catholyte temperatures, valve operation and sequencing, enabling and disabling of RO dewatering, water makeup in the anolyte and catholyte systems, ultrasonic and ultraviolet source operations, off-gas temperatures, and enabling and disabling the data logging, display includes a touch screen monitor for providing an operator of the MEO apparatus with options for running the apparatus, for displaying status of each component in the MEO apparatus based on the information received from the sensors including state of the oxidation process to directly evaluate the data from the sensors on the monitor, and instrumentation processed through a signal conditioner, for measuring activity of redox couples using an oxidation reduction potential (ORP) sensor located throughout the MEO apparatus, connections for connecting the controller to the internet and to other operators for real-time interactive sensing, analyzing, monitoring, viewing, and controlling all parameters and components of the MEO apparatus, connections are connections to the internet, phone line, cell phone, personal computer (PC), and other media devices, a data logging system for recording sensor data used to assess performance and past use of the system for viewing remotely or on-site, wherein the controller system provides information to diagnose problems associated with the MEO apparatus, comprising microprocessors or multi-position cyclic timer switches.

15. The apparatus of claim 12, further comprising an off-gas system for processing off-gas from the anolyte reaction chamber from complete and incomplete combustion of the material including carbon-dioxide, oxygen from oxidation of water molecules at the anode and possibly small amounts of low molecular weight hydrocarbons from incomplete combustion that are gases at the anolyte operating temperature and pressure, an exhaust for exhausting the off-gas extracted by air flow through the anolyte chamber and catholyte chamber, exhaust fan in the exhaust for drawing ambient air into the anolyte chamber through the anolyte air intake/filter and into the catholyte chamber through the catholyte air intake/filter, anolyte chiller, wherein the anolyte demister is cooled by the anolyte chiller, anolyte demister wherein reaction products resulting from the oxidation in the anolyte system are discharged through the anolyte off-gas exit tube to the anolyte demister, wherein easily condensed products of incomplete oxidation are separated in the anolyte demister from the anolyte off-gas stream and are returned to the anolyte chamber or the anolyte reservoir through an anolyte condensate return tube for further oxidation, a gas cleaning system for reducing non-condensable incomplete oxidation products to acceptable levels for atmospheric release after the anolyte off-gas is contacted in a counter current flow gas scrubbing system in the gas cleaning system, wherein the noncondensables from the anolyte demister are introduced into the lower portion of the column through a flow distribution system of the gas cleaning system and a small side stream of freshly oxidized anolyte direct from the electrochemical cell is introduced into the upper portion of the column resulting in the gas phase continuously reacting with the oxidizing mediator species as it rises up the column past the down flowing anolyte, catholyte off-gas handling system for drawing ambient air through the catholyte reservoir and through the catholyte off-gas exit tube to a catholyte demister by the exhaust fan, wherein water vapor in the air stream is condensed in the catholyte demister by the coolant from the catholyte chiller and the condensate returns to the catholyte reservoir through the catholyte condensate return tube.

16. The apparatus of claim 12, further comprising inherent safety features includes
(1) automated apparatus operations to assure all requisite operations and safe guards are synchronized with human activity,
(2) all operations of apparatus are interlocked with all others enabling safe and automated operations,
(3) fully instrumentation to signal alarms when any operating parameters (heater/chiller temperatures, anolyte/catholyte temperatures, ARC level, or anolyte/catholyte flow rate or pressure) are out of default range,
(4) full instrumentation to signal sensor failure and/or electrical interrupt,
(5) alarms that signal a problem and/or failure,
(6) instrumentation that put apparatus into safe mode when problems and/or failures occur,
(7) fail-safe protected when apparatus if operated manually,
(8) monitoring of pressures and temperatures are to protect apparatus equipment.

17. The apparatus of claim 12, further comprising inherent safety features includes
(1) containment vessel with a capacity to hold all the anolyte and catholyte in the apparatus,
(2) leak detectors that sense a leak and the controller automatically goes into shutdown mode,
(3) automatically introduce a neutralizing and absorbing materials from the oxidizer suppress injection tank injected into the containment pan based on the sensor detecting electrolyte,
(4) discharging plates may be in the containment pan to discharge the oxidizer in the electrolyte as soon as the sensor detects presences of electrolyte in the containment pan,
(5) controller reports the status of the materials disposal through the display monitor and places the system in a standby mode when the disposal is complete,
(6) hydrogen detectors will initiate a controlled safe shutdown of the MEO apparatus should the hydrogen gas level exceed a safety limit,
(7) apparatus is segmented by impervious bulkheads to separate auxiliary power systems, gas supply and controller systems from the anolyte and catholyte circulation.

18. The apparatus of claim 12, further comprising an internal power supply providing AC and DC power to the components of the apparatus, external power may be 110 volts AC or higher; internal power supply converts AC to DC and provides a variety of voltage levels throughout the apparatus; a NEMA box may be used to protect from igniting off gases from electrical arcs; electrical compartment may be slightly positive pressurized by air intake and air exhaust fans to not allow off gases to enter the compartment.

19. The apparatus of claim 12, wherein the interior walls of the box having ridges and grooves to promote turbulent flow, thereby reducing adverse boundary layer related phenomena at the electrodes.

20. The apparatus of claim 12, wherein the interior walls, the membranes and the electrodes form plurality of electrochemical cells coupled together and with the electrical connections and the buses and nuts and bolts and clamp holes on the box and the lid adapted for coupling the lid to the box as well as providing easy access to interior of the electrochemical cell.

21. The apparatus of claim 12, further comprising glazed inside surfaces of the box and the lid to protect the surfaces from an oxidizer in the anolyte and acids or alkaline in the catholyte solution.

22. The apparatus of claim 12, wherein the walls of the electrochemical cell are ceramic walls and further comprising oxidation resistant ion selective membranes bonded over interior walls serving as ceramic membranes, wherein oxidation resistant membranes supplement performance of the plural membranes.

23. The apparatus of claim 12, wherein the box and lid are a pier box and lid made from materials selected from the group consisting of fiberglass, polypropylene, metals and composite metals, and wherein interior surfaces of the pier box have a PTFE coating to protect the surfaces from oxidizer in the anolyte and from acids or alkaline in the catholyte.

24. The apparatus of claim 12, further comprising platinum wires or miniature oxidation reduction potential (ORP) electrodes inserted through the lid in each of the anolyte and catholyte and positioned such that electrical potential may be measured between the anolyte and the catholyte to provide information of the concentration of oxidizer in the anolyte and also as an indicator of any leakage in the plural membranes.

25. Apparatus of claim 12, further comprising an oxidation reduction potential (ORP) sensor incorporated in the cell to sense level of oxidizer in the anolyte, an ORP sensor detects the level of oxidizer being produced by the electrochemical cell in an anolyte exit stream from the electrochemical cell, a processor and a signal conditioner connected to the ORP and to the processor, an algorithm in the processor adapted to calculate desired oxidizer concentration in the anolyte solution, and a regulation output from the processor adapted to issue commands that regulate the DC power from the DC power supply, wherein the DC power supply provides the DC potential across the anodes and cathodes in the electrochemical cell, wherein when selected oxidizer concentration level in the anolyte sensed by the ORP is reached, the DC power to the electrochemical cell is reduced or interrupted until the oxidizer level drops to or below the selected oxidizer level, at which point the DC current from the DC power supply are restored in the cell.

26. The apparatus of claim 12, further comprising a discharger connected to the electrochemical cell and a pump connected to the electrochemical cell and to the discharger, for providing controlling anolyte flow between the discharger and the electrochemical cell.

27. The apparatus of claim 12, further comprising a dewatering system connected to the electrochemical cell, the dewatering system having reverse osmosis (RO) units comprising a fluoropolymer/copolymer RO unit having a membrane of a fluoropolymer/copolymer, wherein the fluoropolymer/copolymer membrane used for dewatering of the anolyte by the RO unit when oxidizer in the anolyte in the MEO apparatus would damage a membrane made from typical RO membrane materials and wherein cleaning of oxidizable material from the fluoropolymer/copolymer membrane is accomplished by the action of the oxidizer in the anolyte solution as it passes through the RO unit, a multipass RO unit for a dewatering unit where the osmotic pressure head is so large that the pressure limit on the RO membranes may be exceeded or the membrane partition factor may be insufficient to affect the required degree of separation in a single stage, wherein the anolyte or catholyte is pumped by pumps through the RO membrane, RO tubes made out of the RO membrane fill insides of the RO membrane housing, and wherein a dilute solution of the electrolyte is used for lowering the osmotic pressure between the anolyte and catholyte, a dilute electrolyte reservoir for storing the dilute electrolyte which is pumped by a second stage anolyte pump or second stage catholyte pump as the tube side liquid enters into a RO membrane multipass housing, osmotic pressure difference between the tube side liquid and the shell side pure water stream allows operation below pressure limits on the RO membrane, static RO unit wherein volume of the anolyte is relatively small and the flow rate through the RO membrane is low per unit area thus requiring greater flow area such that the total volume of the tubes required for this surface area exceeds the total anolyte volume.

28. The apparatus of claim 12, further comprising a dewatering tube for controlling levels of the catholyte by dewatering when levels exceed a set level by flowing the catholyte back through a dewater reject tube, valve for controlling liquid flowing through the dewatering tube for the adding of returned catholyte or rejecting water makeup from a water storage tank, wherein after the discharging process is complete the discharger output valve opens to the RO pump and the discharged anolyte solution is processed through the RO membrane which is enclosed in the RO membrane housing, and wherein anolyte RO pressure is sensed by a pressure sensor, water storage tank for storing pure water and a valve controlling supply of the water as needed to the dilute electrolyte, RO unit rejecting to catholyte wherein the anolyte and the catholyte are similar in composition and the RO membranes tolerate the electrolytes, wherein excess water in the anolyte is rejected into the catholyte through the RO membrane, wherein the RO again uses the anolyte solution pumped by the pump as the tube side fluid in the RO membrane housing, and wherein the catholyte solution is pumped by the pump through the shell side, returning the anolyte and the catholyte leaving the housing to the anolyte and the catholyte chambers, respectively, a valve opened to allow all the anolyte solution to be transferred from anolyte system through pump into the RO system tubes in the RO membrane housing, high pressure pump for pressurization of the RO system, RO reservoir is pressurized to several thousand psi with air or nitrogen from the pressurized vessel and let stand until the dewatering has reached the desired goal, a regulator for controlling pressure in the RO system by releasing the air or nitrogen gas from the pressurized vessel until the desired pressure has been reached in the RO system and for holding that pressure until the dewatering is complete, a regulator for holding the anolyte under pressure in the RO membrane in the housing and/or a nitrogen pressure vessel for holding the catholyte under pressure with the catholyte RO pump, a regulator for controlling pressure in the RO system by releasing the air or nitrogen gas from the pressurized vessel until the desired pressure has been reached in the RO system and for holding that pressure until the dewatering is complete, storage tank for storing processed water passing through the membrane, wherein the stored water is available to be returned to either the anolyte or the catholyte or to be rejected from the MEO apparatus, a particulate filter for passing the anolyte and/or catholyte solution exiting the apparatus to remove particulate matter, clean water pump coupled to the cell for pumping clean water into the anolyte chamber and/or the catholyte chamber for restoring levels of the catholyte.

29. The apparatus of claim 12, further comprising an osmotic cell wherein the anolyte and the catholyte have properties such that osmotic pressure drives water from anolyte side to catholyte side of the semi-permeable osmotic membrane, wherein the osmosis cell is pressurized on the anolyte side to increase flow and to dewater the anolyte by driving water from the anolyte to the catholyte, an osmotic cell with selected osmotic fluid wherein the catholyte has too low an osmotic pressure difference and the water in the anolyte will not cross the osmotic membrane, and wherein a second osmotic fluid with a higher osmotic pressure is provided to permit water to pass through the membrane, osmotic cell comprises two separate chambers wherein the anolyte and/or the catholyte flow along one side of an osmotic membrane and wherein another side of the osmotic membrane is in contact with an osmotic fluid having an osmotic pressure that allows water in the anolyte or catholyte to cross the osmotic membrane, an osmotic reservoir for storing the osmotic fluid, a pump for pumping the osmotic fluid from the osmotic reservoir through the osmotic cell and back to the osmotic reservoir, osmotic valve for dewatering the anolyte or the catholyte by operating the valve to allow flow into the RO membrane housing containing the RO membranes.

30. The apparatus of claim 12, further comprising a vacuum evaporation unit for removing water from the anolyte and/or catholyte vacuum evaporation, nanofilters for pretreatment of the materials to remove solids and soluble substances from the anolyte feed stream to the evaporator avoiding airborne infectious release, wherein filtered anolyte and/or catholyte flows into the evaporator, and from the evaporator returns to the anolyte and/or the catholyte chambers and continue to circulate through the vacuum evaporator unit until excess, water in the solutions are reduced to desired levels, vacuum pump for reducing pressure in the evaporator system to less than a vapor pressure of water in the anolyte and/or catholyte at their respective temperatures, and a condenser connected to the system wherein water evaporates and progresses into the condenser, wherein pressure in the evaporator condenser system is controlled by vapor pressure of water at the condenser temperature.

31. The apparatus of claim 12, further comprising a discharger that suppresses electrochemically oxidizers in the anolyte solution when they are not needed or not wanted, wherein a discharge comprises two or more electrodes between which the anolyte flows during discharge, the anolyte, an input valve, a low voltage electrical potential source connected to the electrodes, a switch controlling connection of the source to the discharger, a return through which the anolyte flows out of the discharger and returns to the anolyte reaction chamber.

32. The apparatus of claim 12, further comprising an oxidizer suppression injection systems, wherein oxidizers in the anolyte are suppressed by benign material, wherein the benign material is stored in a suppressor tank.

33. The apparatus of claim 12, further comprising a nitrogen gas system having a nitrogen gas bottle and a manual gas valve that opens and closes the nitrogen gas bottle, when the manual gas valve is opened the nitrogen pressure regulator controls the nitrogen gas pressure to the nitrogen gas system, the nitrogen gas pressure regulator is controlled by commands from a processor and the nitrogen gas system is used to purge the catholyte reservoir in case the hydrogen gas exceeds a two percent level in the off-gas handling system, the catholyte reservoir purge regulator is opened by a command from the PLC allowing nitrogen gas to flow, the catholyte reservoir purge valve is opened by a PLC command allowing nitrogen gas to purge the catholyte reservoir, catholyte reservoir purge valve closes the catholyte air sparge so that the nitrogen purges the catholyte reservoir, wherein the second embodiment of the nitrogen gas system is to provide gas pressure to power the valves in the anolyte system and catholyte system, the nitrogen instruments enable valve opens by command from the PLC to provide nitrogen gas pressure to instruments and actuators, the nitrogen gas pressure is regulated to the instruments by the instrument nitrogen pressure regulator, and to the actuators by the actuator nitrogen pressure regulator.

34. The apparatus of claim 12, further comprising a hydrogen gas system for the catholyte reservoir when selected catholytes are used, a processor controls through operator selection which of the two embodiments are to be used when the MEO apparatus is operating, wherein when the first hydrogen gas is not going to be collected for further use, hydrogen is diluted by air entering the catholyte reservoir through the catholyte air intake filter when the catholyte air intake valve is in the open position, the hydrogen selection valve is positioned by commands from the PLC to exhaust the diluted hydrogen through the exhaust fan to the off-gas vent, the hydrogen gas detector monitors the hydrogen to insure the percentage of hydrogen is at or below the regulated safe level, the sail switch monitors the flow through the exhaust fan to ensure the flow is adequate, the catholyte solution enters the catholyte reservoir from the electrochemical cell and returns from the catholyte reservoir through the catholyte pump to the catholyte system, the hydrogen exits the catholyte reservoir and a hydrogen gas detector detects the amount of hydrogen, the hydrogen off gas passes through a catholyte demister, a chilled coolant flows from the catholyte chiller to the catholyte demister and returns to the catholyte chiller.

35. The apparatus of claim 12, further comprising a hydrogen gas system for the catholyte reservoir selected catholytes are used, a processor controls through operator selection which of the two embodiments are to be used when the MEO apparatus is operating, wherein when the hydrogen gas is being collected for use by either a fuel cell system or a combustion system such as water heater, the catholyte air intake valve is in the closed position, the hydrogen selection valve is in the position to pass the hydrogen gas to hydrogen gas pump, the hydrogen gas pump compresses the hydrogen, which passes through a hydrogen gas regulator, the hydrogen sensor measures the percentage of hydrogen gas flowing to the hydrogen gas regulator, the compressed hydrogen is stored in a pressurized hydrogen storage bottle, the hydrogen is released through the hydrogen regulator to the in use devises, in both embodiments there is a nitrogen gas bottle connected to the catholyte reservoir through a nitrogen pressure regulator, the nitrogen is used to purge the hydrogen gas out of the catholyte reservoir and connecting components by opening the nitrogen purge valve, wherein a third embodiment the hydrogen gas is captured by zirconium or Ziralloy getters, the getters for latter disposal absorb the hydrogen gas.

36. The apparatus of claim 12, further comprising safety systems apparatus safety containment pan built into the MEO apparatus with the capacity to hold all the electrolytes (both anolyte and catholyte together) without spilling it outside the apparatus, the containment pan may hold a neutralizing and absorbing agent to assist in the containment of the electrolytes, the electrolyte may be contained from either a leak or catastrophic failure from either the anolyte system and/or the catholyte system, the containment pan has a spill sensor to detect the introduction of any electrolyte into the containment pan, wherein a second embodiment of the MEO apparatus may automatically introduce a neutralizing and absorbing materials from the oxidizer suppression injection tank injected into the containment pan based on the sensor-detecting electrolyte.

* * * * *